(12) United States Patent
Lee et al.

(10) Patent No.: US 8,104,470 B2
(45) Date of Patent: *Jan. 31, 2012

(54) COORDINATED USE OF RESPIRATORY AND CARDIAC THERAPIES FOR SLEEP DISORDERED BREATHING

(75) Inventors: Kent Lee, Shoreview, MN (US); Jesse W. Hartley, White Bear Lake, MN (US); Jeffrey E. Stahmann, Ramsey, MN (US); Quan Ni, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 236 days.

This patent is subject to a terminal disclaimer.

(21) Appl. No.: 12/545,670

(22) Filed: Aug. 21, 2009

(65) Prior Publication Data

US 2009/0308395 A1    Dec. 17, 2009

Related U.S. Application Data

(63) Continuation of application No. 10/930,979, filed on Aug. 31, 2004, now Pat. No. 7,591,265.

(60) Provisional application No. 60/504,561, filed on Sep. 18, 2003.

(51) Int. Cl.
*A61N 1/18* (2006.01)

(52) U.S. Cl. ............. 128/204.18; 128/204.23; 607/42

(58) Field of Classification Search ............ 128/204.18, 128/204.23, 204.21, 204.22, 200.24, 204.28, 128/912; 607/3, 9, 42; 600/529, 26, 27
See application file for complete search history.

(56) References Cited

U.S. PATENT DOCUMENTS

| | | |
|---|---|---|
| 4,365,636 A | 12/1982 | Barker |
| 4,562,841 A | 1/1986 | Brockway et al. |
| 4,702,253 A | 10/1987 | Nappholz et al. |
| 4,813,427 A | 3/1989 | Schlaefke et al. |
| 4,827,935 A | 5/1989 | Geddes et al. |
| 4,830,008 A | 5/1989 | Meer |
| 4,836,219 A | 6/1989 | Hobson et al. |
| 4,856,524 A | 8/1989 | Baker, Jr. |
| 4,928,688 A | 5/1990 | Mower |
| 5,024,222 A | 6/1991 | Thacker |
| 5,036,849 A | 8/1991 | Hauck et al. |
| 5,105,354 A | 4/1992 | Nishimura |
| 5,123,425 A | 6/1992 | Shannon, Jr. et al. |
| 5,146,918 A | 9/1992 | Kallok et al. |

(Continued)

FOREIGN PATENT DOCUMENTS

EP    0750920    1/1997

(Continued)

OTHER PUBLICATIONS

Aircraft Noise and Sleep Disturbance: Final Report', prepared by the Civil Aviation Authority London on behalf of the Department of Trade, Aug. 1980 (CAA Report).

(Continued)

*Primary Examiner* — Steven Douglas
(74) *Attorney, Agent, or Firm* — Hollingsworth & Funk, LLC

(57) ABSTRACT

Methods and systems involve coordinating therapies used for treating disordered breathing. Disordered breathing therapies may include cardiac electrical stimulation therapy and external respiratory therapy as well as other therapies for treating disordered breathing in a patient. The therapies delivered to the patient may be coordinated to enhance effectiveness of the therapy, to reduce therapy interactions, to improve patient sleep, or to achieve other therapeutic goals.

20 Claims, 27 Drawing Sheets

U.S. PATENT DOCUMENTS

| | | |
|---|---|---|
| 5,178,156 A | 1/1993 | Takishima et al. |
| 5,187,657 A | 2/1993 | Forbes |
| 5,203,348 A | 4/1993 | Dahl et al. |
| 5,211,173 A | 5/1993 | Kallok et al. |
| 5,215,082 A | 6/1993 | Kallok et al. |
| 5,230,337 A | 7/1993 | Dahl et al. |
| 5,233,983 A | 8/1993 | Markowitz |
| 5,245,995 A | 9/1993 | Sullivan et al. |
| 5,280,791 A | 1/1994 | Lavie |
| 5,284,136 A | 2/1994 | Hauck et al. |
| 5,299,118 A | 3/1994 | Martens et al. |
| 5,301,677 A | 4/1994 | Hsung |
| 5,313,953 A | 5/1994 | Yomtov et al. |
| 5,334,222 A | 8/1994 | Salo et al. |
| 5,335,657 A | 8/1994 | Terry, Jr. et al. |
| 5,353,788 A | 10/1994 | Miles |
| 5,360,442 A | 11/1994 | Dahl et al. |
| 5,366,496 A | 11/1994 | Dahl et al. |
| 5,376,476 A | 12/1994 | Eylon |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,411,031 A | 5/1995 | Yomtov |
| 5,466,245 A | 11/1995 | Spinelli et al. |
| 5,483,969 A | 1/1996 | Testerman et al. |
| 5,485,851 A | 1/1996 | Erickson |
| 5,517,983 A | 5/1996 | Deighan et al. |
| 5,520,176 A | 5/1996 | Cohen |
| 5,522,862 A | 6/1996 | Testerman et al. |
| 5,540,727 A | 7/1996 | Tockman et al. |
| 5,545,186 A | 8/1996 | Olson et al. |
| 5,545,202 A | 8/1996 | Dahl et al. |
| 5,549,655 A | 8/1996 | Erickson |
| 5,593,431 A | 1/1997 | Sheldon |
| 5,603,732 A | 2/1997 | Dahl et al. |
| 5,632,281 A | 5/1997 | Rayburn |
| 5,645,570 A | 7/1997 | Corbucci |
| 5,704,345 A | 1/1998 | Berthon-Jones |
| 5,713,933 A | 2/1998 | Condie et al. |
| 5,715,812 A | 2/1998 | Deighan et al. |
| 5,720,771 A | 2/1998 | Snell |
| 5,738,102 A | 4/1998 | Lemelson |
| 5,792,188 A | 8/1998 | Starkweather et al. |
| 5,802,188 A | 9/1998 | McDonough |
| 5,814,087 A | 9/1998 | Renirie |
| 5,836,987 A | 11/1998 | Baumann et al. |
| 5,844,680 A | 12/1998 | Sperling |
| 5,855,593 A | 1/1999 | Olson et al. |
| 5,861,011 A | 1/1999 | Stoop |
| 5,891,023 A | 4/1999 | Lynn |
| 5,902,250 A | 5/1999 | Verrier et al. |
| 5,911,218 A | 6/1999 | DiMarco |
| 5,916,243 A | 6/1999 | KenKnight et al. |
| 5,944,680 A | 8/1999 | Christopherson et al. |
| 5,957,861 A | 9/1999 | Combs et al. |
| 5,964,778 A | 10/1999 | Fugoso et al. |
| 5,970,975 A | 10/1999 | Estes et al. |
| 5,974,340 A | 10/1999 | Kadhiresan |
| 5,974,349 A | 10/1999 | Levine |
| 6,026,320 A | 2/2000 | Carlson et al. |
| 6,044,297 A | 3/2000 | Sheldon et al. |
| 6,044,298 A | 3/2000 | Salo et al. |
| 6,055,454 A | 4/2000 | Heemels |
| 6,059,725 A | 5/2000 | Steinschneider |
| 6,064,910 A | 5/2000 | Andersson et al. |
| 6,076,015 A | 6/2000 | Hartley et al. |
| 6,091,973 A | 7/2000 | Colla et al. |
| 6,091,986 A | 7/2000 | Keimel |
| 6,099,479 A | 8/2000 | Christopherson et al. |
| 6,120,441 A | 9/2000 | Griebel |
| 6,126,611 A | 10/2000 | Bourgeois et al. |
| 6,128,534 A | 10/2000 | Park et al. |
| 6,132,384 A | 10/2000 | Christopherson et al. |
| 6,141,581 A | 10/2000 | Olson et al. |
| 6,141,590 A | 10/2000 | Renirie et al. |
| 6,148,814 A | 11/2000 | Clemmer et al. |
| 6,168,568 B1 | 1/2001 | Gavriely |
| 6,190,326 B1 | 2/2001 | McKinnon et al. |
| 6,200,265 B1 | 3/2001 | Walsh et al. |
| 6,212,435 B1 | 4/2001 | Lattner et al. |
| 6,221,011 B1 | 4/2001 | Bardy |
| 6,240,316 B1 | 5/2001 | Richmond et al. |
| 6,251,126 B1 | 6/2001 | Ottenhoff et al. |
| 6,258,039 B1 | 7/2001 | Okamoto et al. |
| 6,259,947 B1 | 7/2001 | Olson et al. |
| 6,269,269 B1 | 7/2001 | Ottenhoff et al. |
| 6,270,457 B1 | 8/2001 | Bardy |
| 6,272,377 B1 | 8/2001 | Sweeney et al. |
| 6,275,727 B1 | 8/2001 | Hopper et al. |
| 6,277,072 B1 | 8/2001 | Bardy |
| 6,280,380 B1 | 8/2001 | Bardy |
| 6,285,907 B1 | 9/2001 | Kramer et al. |
| 6,286,508 B1 | 9/2001 | Remmers et al. |
| 6,312,378 B1 | 11/2001 | Bardy |
| 6,331,536 B1 | 12/2001 | Radulovacki et al. |
| 6,336,903 B1 | 1/2002 | Bardy |
| 6,351,669 B1 | 2/2002 | Hartley et al. |
| 6,351,670 B1 | 2/2002 | Kroll |
| 6,353,759 B1 | 3/2002 | Hartley et al. |
| 6,358,203 B2 | 3/2002 | Bardy |
| 6,361,494 B1 | 3/2002 | Lindenthaler |
| 6,361,522 B1 | 3/2002 | Scheiner et al. |
| 6,363,270 B1 | 3/2002 | Colla et al. |
| 6,366,813 B1 | 4/2002 | DiLorenzo |
| 6,368,284 B1 | 4/2002 | Bardy |
| 6,368,287 B1 | 4/2002 | Hadas |
| 6,371,922 B1 | 4/2002 | Baumann et al. |
| 6,375,621 B1 | 4/2002 | Sullivan |
| 6,387,907 B1 | 5/2002 | Hendricks et al. |
| 6,398,728 B1 | 6/2002 | Bardy |
| 6,409,675 B1 | 6/2002 | Turcott |
| 6,411,848 B2 | 6/2002 | Kramer et al. |
| 6,414,183 B1 | 7/2002 | Sakamoto et al. |
| 6,415,183 B1 | 7/2002 | Scheiner et al. |
| 6,424,865 B1 | 7/2002 | Ding |
| 6,438,407 B1 | 8/2002 | Ousdigian et al. |
| 6,438,410 B2 | 8/2002 | Hsu et al. |
| 6,440,066 B1 | 8/2002 | Bardy |
| 6,449,503 B1 | 9/2002 | Hsu |
| 6,454,719 B1 | 9/2002 | Greenhut |
| 6,459,929 B1 | 10/2002 | Hopper et al. |
| 6,467,333 B2 | 10/2002 | Lewis et al. |
| 6,480,733 B1 | 11/2002 | Turcott |
| 6,487,443 B2 | 11/2002 | Olson et al. |
| 6,527,729 B1 | 3/2003 | Turcott |
| 6,542,775 B2 | 4/2003 | Ding et al. |
| 6,572,543 B1 | 6/2003 | Christopherson et al. |
| 6,574,507 B1 | 6/2003 | Bonnet |
| 6,580,944 B1 | 6/2003 | Katz et al. |
| 6,589,188 B1 | 7/2003 | Street et al. |
| 6,595,928 B2 | 7/2003 | Mansy et al. |
| 6,597,951 B2 | 7/2003 | Kramer et al. |
| 6,600,949 B1 | 7/2003 | Turcott |
| 6,641,542 B2 | 11/2003 | Cho et al. |
| 6,658,292 B2 | 12/2003 | Kroll et al. |
| 6,662,032 B1 | 12/2003 | Gavish et al. |
| 6,694,186 B2 | 2/2004 | Bardy |
| 6,723,055 B2 | 4/2004 | Hoffman |
| 6,731,984 B2 | 5/2004 | Cho et al. |
| 6,741,885 B1 | 5/2004 | Park et al. |
| 6,748,252 B2 | 6/2004 | Lynn et al. |
| 6,752,765 B1 | 6/2004 | Jensen et al. |
| 6,752,766 B2 | 6/2004 | Kowallik et al. |
| 6,773,404 B2 | 8/2004 | Poezevera et al. |
| 6,810,287 B2 | 10/2004 | Zhu et al. |
| 6,881,192 B1 | 4/2005 | Park |
| 6,904,320 B2 | 6/2005 | Park et al. |
| 6,910,481 B2 | 6/2005 | Kimmel et al. |
| 6,928,324 B2 | 8/2005 | Park et al. |
| 6,964,641 B2 | 11/2005 | Cho et al. |
| 6,988,498 B2 | 1/2006 | Berthon-Jones et al. |
| 7,025,730 B2 | 4/2006 | Cho et al. |
| 7,062,308 B1 | 6/2006 | Jackson |
| 7,092,755 B2 | 8/2006 | Florio |
| 7,130,687 B2 | 10/2006 | Cho et al. |
| 7,155,278 B2 | 12/2006 | King et al. |
| 7,189,204 B2 | 3/2007 | Ni et al. |

| | | |
|---|---|---|
| 7,207,945 B2 | 4/2007 | Bardy |
| 7,225,013 B2 | 5/2007 | Geva et al. |
| 7,225,809 B1 | 6/2007 | Bowen et al. |
| 7,252,640 B2 | 8/2007 | Ni et al. |
| 2001/0000346 A1 | 4/2001 | Ruton et al. |
| 2001/0018547 A1 | 8/2001 | Mechlenburg et al. |
| 2001/0031930 A1 | 10/2001 | Roizen et al. |
| 2002/0147476 A1 | 10/2002 | Daum |
| 2002/0169384 A1 | 11/2002 | Kowallik et al. |
| 2002/0193685 A1 | 12/2002 | Mate et al. |
| 2002/0193697 A1 | 12/2002 | Cho et al. |
| 2002/0193839 A1 | 12/2002 | Cho et al. |
| 2003/0023184 A1 | 1/2003 | Pitts-Crick et al. |
| 2003/0055461 A1 | 3/2003 | Girouard et al. |
| 2003/0073919 A1 | 4/2003 | Hampton et al. |
| 2003/0088027 A1 | 5/2003 | Chin et al. |
| 2003/0100925 A1 | 5/2003 | Pape et al. |
| 2003/0105497 A1 | 6/2003 | Zhu et al. |
| 2003/0153953 A1 | 8/2003 | Park et al. |
| 2003/0153954 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0171687 A1 | 9/2003 | Irie et al. |
| 2003/0187336 A1 | 10/2003 | Odagiri et al. |
| 2003/0195571 A1 | 10/2003 | Burnes et al. |
| 2003/0199945 A1 | 10/2003 | Ciulla |
| 2003/0204213 A1 | 10/2003 | Jensen et al. |
| 2003/0216789 A1 | 11/2003 | Deem et al. |
| 2004/0002742 A1 | 1/2004 | Florio |
| 2004/0030362 A1 | 2/2004 | Hill et al. |
| 2004/0059240 A1 | 3/2004 | Cho et al. |
| 2004/0073093 A1 | 4/2004 | Hatlestad |
| 2004/0088027 A1 | 5/2004 | Burnes et al. |
| 2004/0102814 A1 | 5/2004 | Sorensen et al. |
| 2004/0111040 A1 | 6/2004 | Ni et al. |
| 2004/0116981 A1 | 6/2004 | Mazar |
| 2004/0122488 A1 | 6/2004 | Mazar et al. |
| 2004/0128161 A1 | 7/2004 | Mazar et al. |
| 2004/0133079 A1 | 7/2004 | Mazar et al. |
| 2004/0138719 A1 | 7/2004 | Cho et al. |
| 2004/0163648 A1 | 8/2004 | Burton |
| 2004/0176809 A1 | 9/2004 | Cho et al. |
| 2004/0210154 A1 | 10/2004 | Kline |
| 2004/0210155 A1 | 10/2004 | Takemura et al. |
| 2005/0039745 A1 | 2/2005 | Stahmann et al. |
| 2005/0042589 A1 | 2/2005 | Hatlestad et al. |
| 2005/0043644 A1 | 2/2005 | Stahmann et al. |
| 2005/0043652 A1 | 2/2005 | Lovett et al. |
| 2005/0043772 A1 | 2/2005 | Stahmann et al. |
| 2005/0061315 A1 | 3/2005 | Lee et al. |
| 2005/0119711 A1 | 6/2005 | Cho et al. |
| 2005/0142070 A1 | 6/2005 | Hartley et al. |
| 2005/0145246 A1 | 7/2005 | Hartley et al. |
| 2007/0161873 A1 | 7/2007 | Ni et al. |
| 2007/0282215 A1 | 12/2007 | Ni et al. |

FOREIGN PATENT DOCUMENTS

| | | |
|---|---|---|
| EP | 0770407 | 5/1997 |
| EP | 0940155 | 9/1999 |
| EP | 1151718 | 11/2001 |
| EP | 1162125 | 12/2001 |
| EP | 1172125 | 1/2002 |
| EP | 1317943 | 6/2003 |
| WO | WO8402080 | 7/1984 |
| WO | WO9203983 | 3/1992 |
| WO | WO9904841 | 4/1999 |
| WO | WO0001438 | 1/2000 |
| WO | WO0017615 | 3/2000 |
| WO | WO0240096 | 5/2002 |
| WO | WO02087696 | 11/2002 |
| WO | WO03075744 | 9/2003 |
| WO | WO2004062485 | 7/2004 |
| WO | WO2005028029 | 3/2005 |

OTHER PUBLICATIONS

Altshule et al., The Effect of Position on Periodic Breathing in Chronic Cardiac Decomposition, New Eng. Journal of Med., vol. 259, No. 22, pp. 1064-1066, Nov. 27, 1958.

Balaban et al., Feasibility of Screening for Sleep Apnea Using Pacemaker Impedance Sensor, NASPE (2001).

Bradley et al., Pathophysiologic and Therapeutic Implications of Sleep Apnea in Congestive Heart Failure, 3 J. Cardiac Failure 223-240 (1996). Abstract only.

Bradley et al., Sleep Apnea and Heart Failure, Park I: Obstructive Sleep Apnea, 107 Circulation 1671-1678 (2003).

Dark et al., Breathing Pattern Abnormalities and Arterial Oxygen Desaturation During Sleep in the Congestive Heart Failure Syndrome, Chest, Jun. 1987, 6:833-6.

Garrigue et al., Night Atrial Overdrive with DDD Pacing Results in a Significant Reduction of Sleep Apnea Episodes and QOL Improvement in Heart Failure Patients, NASPE (2001).

Garrigue et al., Benefit of Atrial Pacing in Sleep Apnea Syndrome, 346 N. Engl. J. Med. 404-412 (2002). Abstract only.

Hilton et al., Evaluation of Frequency and Time-frequency Spectral Analysis of Heart Rate Variability as a Diagnostic Marker of the Sleep Apnea Syndrome, 37 Med. Biol. Eng. Comput. 760-769 (1999).

Hoffman et al., Cheyne-Stokes Respiration in Patients Recovering from Acute Cardiogenic Pulmonary Edema, Chest 1990, 97:410-12.

Jais et al., Night Atrial Overdrive with DDD Pacing: a New Therapy for Sleep Apnea Syndrome, NASPE (2000).

Javaheri et al., Sleep Apnea in 81 Ambulatory Male Patients with Stable Heart Failure: Types and Their Prevalences, Consequences, and Presentations, 97 Circulation 2154-2159 (1998).

Junyu et al., Posture Detection Algorithm Using Multi Axis DC-Accelerometer, Pace vol. 22, Apr. 1999.

Mansfield, D. et al., Effects of Continuous Positive Airway Pressure on Lung Function in Patients with Chronic Obstructive Pulmonary Disease and Sleep Disordered Breathing, Respirology 365-70, 1999. Abstract only.

Aljilore et al., Nightcap: Laboratory and home-based evaluation of a portable sleep monitor, 32 Psychophysiology, 32-98 (1995). Abstract only.

Reddel et al., Analysis of Adherence to Peak Flow Monitoring When Recording of Data is Electronic, BMJ 146-147, 2002.

Rees et al., Paroxysmal Nocturnal Dyspnoea and Periodic Respiration, The Lancet, Dec. 22-29, 1979, pp. 1315-1317. Abstract only.

Tkacova et al., Left Ventricular Volume in Patients with Heart Failure and Cheyne-Strokes Respiration during Sleep, Am. Journal, Respir. Crit. Care Med., vol. 156, pp. 1549-1555, 1997.

Verrier et al., Sleep, dreams, and sudden death: the case for sleep as an autonomic stress test for the heart, 31 Cardiovascular Research 181-211 (1996).

Verrier et al., Sleep Related Cardiovascular Risk: New Home-Based Monitoring Technology for Improved Diagnosis and Therapy, 2 A.N.E. 158-175 (1997).

Roche et al., Screening of Obstructive Sleep Apnea Syndrome by Heart Rate Variability Analysis, 100 Circulation 1411-1455 (1999).

Shahrokh, A Mechanism of Central Sleep Apnea in Patients With Heart Failure,341 N. Engl. J. Med. 949-954 (1999).

Vanninen et al., Cardiac Sympathovagal Balance During Sleep Apnea Episodes, 16 Clin. Physiol. 209-216 (1996).

Waldemark et al., Detection of Apnea using Short Window FFT Technique and Artificial Neural Network, 3390 SPIE International Society for Optical Engineering 122-133 (1998).

Young et al., The Occurrence of Sleep-Disordered Breathing Among Middle Aged Adults, N. Engl. J. Med. 1230-1235 (1993).

Office Action dated Jun. 12, 2007 from priority U.S. Appl. No. 10/930,979.

Office Action dated Mar. 31, 2008 from priority U.S. Appl. No. 10/930,979.

Office Action dated Jun. 29, 2007 from U.S. Appl. No. 10/643,016.

File History for EP Application No. 08075738.8 as retrieved from European Patent Office Electronic File System on Jan. 21, 2011, 28 pages.

Notice of Allowance dated Apr. 27, 2009 from U.S. Appl. No. 10/930,979, 4 pages.

Office Action Response dated Jun. 30, 2008 from U.S. Appl. No. 10/930,979, 9 pages.

Office Action dated Mar. 31, 2008 from U.S. Appl. No. 10/930,979, 10 pages.
Office Action Response dated Nov. 13, 2007 from U.S. Appl. No. 10/930,979, 17 pages.
Office Action dated Jun. 12, 2007 from U.S. Appl. No. 10/930,979, 12 pages.
International Search Report dated Dec. 22, 2004 from PCT Application No. PCT/US2004/030787, 8 pages.
Office Action dated May 9, 2007 from European Application No. 04784602.7, 3 pages.
Office Action dated Jan. 10, 2008 from European Application No. 04784602.7, 3 pages.
Office Action Response dated Apr. 17, 2008 from European Application No. 04784602.7, 10 pages.
Office Action dated Dec. 21, 2008 from European Application No. 04784602.7, 6 pages.

COORDINATED USE OF RESPIRATORY AND CARDIAC THERAPIES FOR SLEEP DISORDERED BREATHING

RELATED PATENT DOCUMENTS

This application is a continuation of Ser. No. 10/930,979 filed Aug. 31, 2004, now U.S. Pat. No. 7,591,265, which claims the benefit of Provisional Patent Application Ser. No. 60/504,561, filed on Sep. 18, 2003, to which priority is claimed pursuant to 35 U.S.C. §120 and 35 U.S.C. §119(e), respectively, and which are hereby incorporated herein by reference in their entireties.

FIELD OF THE INVENTION

The present invention relates generally to providing therapy for sleep disordered breathing.

BACKGROUND OF THE INVENTION

The human body functions through a number of interdependent physiological systems controlled through various mechanical, electrical, and chemical processes. The metabolic state of the body is constantly changing. For example, as exercise level increases, the body consumes more oxygen and gives off more carbon dioxide. The cardiac and pulmonary systems maintain appropriate blood gas levels by making adjustments that bring more oxygen into the system and dispel more carbon dioxide. The cardiovascular system transports blood gases to and from the body tissues. The respiration system, through the breathing mechanism, performs the function of exchanging these gases with the external environment. Together, the cardiac and respiration systems form a larger anatomical and functional unit denoted the cardiopulmonary system.

Various disorders may affect the cardiovascular, respiratory, and other physiological systems. For example, heart failure (HF) is a clinical syndrome that impacts a number of physiological processes. Heart failure is an abnormality of cardiac function that causes cardiac output to fall below a level adequate to meet the metabolic demand of peripheral tissues. Heart failure is usually referred to as congestive heart failure (CHF) due to the accompanying venous and pulmonary congestion. Congestive heart failure may have a variety of underlying causes, including ischemic heart disease (coronary artery disease), hypertension (high blood pressure), and diabetes, among others.

Disordered breathing is a respiratory system condition that affects a significant percentage of patients between 30 and 60 years. Disordered breathing, including apnea and hypopnea, may be caused, for example, by an obstructed airway, or by derangement of the signals from the brain controlling respiration. Sleep disordered breathing is associated with excessive daytime sleepiness, systemic hypertension, increased risk of stroke, angina and myocardial infarction. Disordered breathing is related to congestive heart failure and can be particularly serious for patients concurrently suffering from cardiovascular deficiencies.

Various types of disordered breathing have been identified, including, apnea (interrupted breathing), hypopnea (shallow breathing), tachypnea (rapid breathing), hyperpnea (heavy breathing), and dyspnea (labored breathing). Combinations of the respiratory cycles described above may be observed, including, for example, periodic breathing and Cheyne-Stokes respiration (CSR). Cheyne-Stokes respiration is particularly prevalent among heart failure patients, and may contribute to the progression of heart failure.

Effective approaches to treating sleep disordered breathing are needed. The present invention fulfills these and other needs, and addresses other deficiencies of prior art implementations and techniques.

SUMMARY OF THE INVENTION

Various embodiments of present invention involve methods and systems for coordinating sleep disordered breathing therapies. In accordance with one embodiment, a method for treating disordered breathing includes controlling an patient-external respiratory therapy delivered to a patient and controlling a cardiac therapy delivered to the patient. The patient-external respiratory therapy and the cardiac therapy are coordinated to treat the disordered breathing.

In accordance with another embodiment of the invention, a medical system includes a respiratory therapy controller configured to control an external respiratory therapy delivered to a patient and a cardiac therapy controller configured to deliver a cardiac therapy to the patient. The system also includes a processor, coupled to the respiratory therapy controller and the cardiac therapy controller. The processor is configured to coordinate delivery of the external respiratory therapy and the cardiac therapy to treat disordered breathing.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
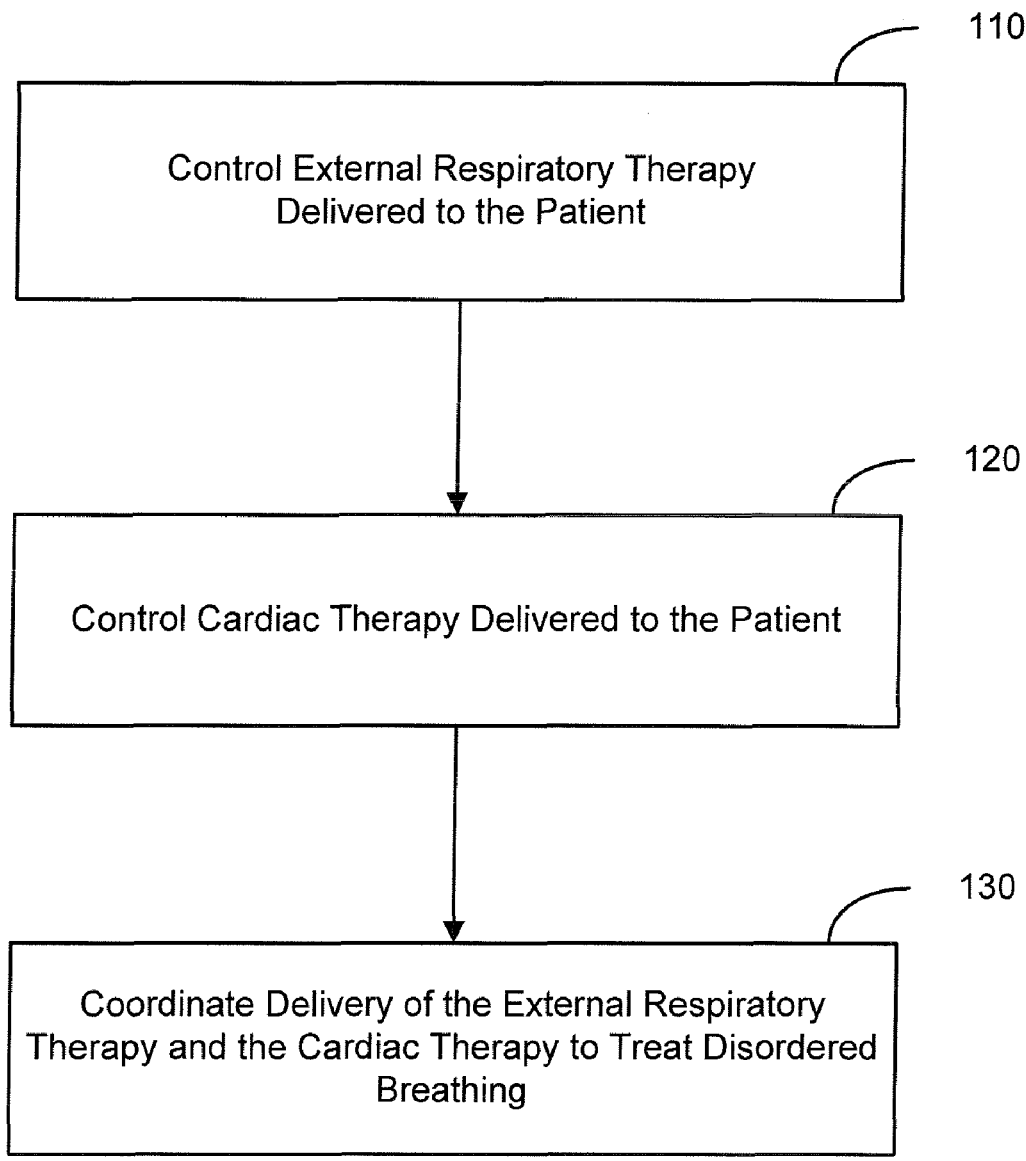
FIGS. 1A-B are flowcharts illustrating methods that involve controlling and coordinating cardiac therapy and respiratory therapy in order to coordinate sleep disordered breathing therapy in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown by way of illustration, various embodiments by which the invention may be practiced. It is to be understood that other embodiments may be utilized, and structural and functional changes may be made without departing from the scope of the present invention.

Sleep disordered breathing may be more effectively monitored and/or treated using a coordinated approach. Various embodiments of the invention are implemented using medical systems employing two or more patient-external and/or patient-internal medical devices. The medical devices may communicate or otherwise operate in concert to provide coordinated disordered breathing therapy.

Embodiments of the invention are directed to methods and systems utilizing a plurality of therapies to treat sleep disordered breathing. The therapies include, at least, an external respiratory therapy and cardiac electrical stimulation therapy. Other therapies may also be cooperatively utilized.

Delivery of the plurality of therapies may be coordinated to achieve various therapeutic goals, e.g., to enhance overall therapy efficacy, to reduce impact to the patient, to avoid therapy interactions, among others. According to one example, coordination of therapies may involve shifting the therapy burden from one type of therapy to another type of therapy in response to events or conditions. In one implementation, shifting the burden from one type of therapy to another type of therapy may involve initiating or increasing a first type of disordered breathing therapy and terminating or decreasing a second type of disordered breathing therapy. Another example of coordinating therapy may involve using one type of therapy to treat one type of disordered breathing, and using another type of therapy to treat another type of disordered breathing.

Various types of therapies have been used to treat sleep disordered breathing. Positive airway pressure devices, e.g., continuous positive airway pressure (CPAP) devices are among the most frequently used mechanical respiration therapy devices employed for treating sleep disordered breathing. Sleep disordered breathing has also been treated using muscle and/or nerve stimulation therapy. For example, a treatment for obstructive sleep apnea involves electrical activation of the tongue muscles. The hypoglossal (HG) nerve innervates the protrusor and retractor tongue muscles. In one approach, an appropriately applied electrical stimulation to the hypoglossal nerve, for example, may prevent backward movement of the tongue, thus preventing the tongue from obstructing the airway.

Central sleep apnea may also be treated by phrenic nerve pacing, also referred to as diaphragmatic pacing. Phrenic nerve pacing uses an electrode implanted in the chest to stimulate the phrenic nerve. The phrenic nerve is generally known as the motor nerve of the diaphragm. It runs through the thorax, along the heart, and then to the diaphragm. Diaphragmatic pacing involves the use of electronic stimulation of the phrenic nerve to control the patient's diaphragm and induce a respiratory cycle. Pacing the phrenic nerve may be accomplished by surgically placing a nerve cuff on the phrenic nerve, and then delivering an electric stimulus. The electric stimulus of the phrenic nerve then causes the diaphragm to induce a respiratory cycle.

Recently, cardiac pacing therapy has been used as a therapy for disordered breathing. Cardiac pacing therapy may be implemented using an implanted electrical pulse generator coupled to endocardiac leads inserted into one or more heart chambers. Cardiac pacing for sleep disordered breathing treatment may include pacing one or more heart chambers, and may involve pacing at a rate above a lower rate limit during sleep and/or during episodes of disordered breathing, for example. Other forms of cardiac pacing such as cardiac resynchronization therapy, biventricular pacing can be delivered to the patient to treat disordered breathing.

Another cardiac therapy that can be adapted to mitigate disordered breathing involves non-excitatory stimulation therapy. In one example, non-excitatory cardiac stimulation therapy involves electrical stimulation of one or more heart chambers, e.g., the left and/or right ventricles, or other cardiac sites, at an energy level below a capture threshold. In another example, non-excitatory cardiac stimulation therapy involves cardiac electrical stimulation delivered to one or more heart chambers during absolute refractory periods of the cardiac tissue. The non-excitatory stimulation may improve cardiac contractility. The non-excitatory cardiac stimulation therapy may be used alone or in combination with cardiac pacing therapy to provide a comprehensive therapy regimen for patients with CHF and disordered breathing such as Cheyne-Stokes respiration.

Cardiac therapy has also been used to mitigate disordered breathing using methods that involve overdrive cardiac pacing of one or more atria or one or more ventricles.

Drug therapy may also be used to treat disordered breathing. Drugs may be delivered to the patient through one or more automatically controllable drug delivery devices, e.g., a drug pump, a controllable nebulizer, or an electrically activated drug patch, for example.

As illustrated in the flowchart of FIG. 1A, embodiments of the invention are directed to an automated method for controlling disordered breathing therapy delivered to a patient. The method involves controlling 110 delivery of an external respiratory therapy and controlling delivery 120 of a cardiac therapy. The external respiratory therapy and the cardiac therapy are coordinated 130 to treat disordered breathing.

In various implementations, one or more conditions affecting the patient and associated with disordered breathing and/or disordered breathing therapy may be sensed. The sensed conditions may be used, for example, to detect and/or predict disordered breathing episodes, determine a severity of disordered breathing, detect sleep, assess sleep quality, evaluate an efficacy of the therapy, evaluate an impact of the therapy on the patient, determine therapy interactions, determine patient usage of the therapies, among other factors. Coordination of the therapies may be performed based on the sensed conditions. The therapies may be adjusted to enhance therapy effectiveness, to reduce an impact of the therapy, to avoid or reduce therapy interactions, and/or to accomplish other therapeutic goals.

According to embodiments presented herein, a coordinating processor unit is used to generate control signals used for controlling disordered breathing therapies delivered to the patient. In one embodiment, the coordinating unit may transmit control signals directly to an external respiratory therapy device and a cardiac therapy device. The control signals may be used by the respective therapy devices to automatically adjust the therapy delivered to the patient. In another embodiment, both the coordinating unit and the therapy devices may be communicatively coupled to a separate medical device, such as a device programmer or patient management system. The coordinating unit may transmit control information indirectly to the therapy devices through a device programmer or patient management system.

Advanced patient management (APM) systems involve a system of medical devices that are accessible through various communications technologies. Medical information may be transmitted to a remote patient management server from the various medical devices. The medical information may be analyzed and used to diagnose and/or monitor disease progression, to determine and control delivery of appropriate therapies for the patient, and/or for other medical purposes. Advanced patient management techniques, aspects of which may be utilized in systems and methods providing coordinated sleep disordered breathing therapy in accordance with embodiments of the invention, are further described in U.S. Pat. Nos. 6,336,903, 6,312,378, 6,270,457, and 6,398,728 which are incorporated herein by reference.

In one embodiment of the invention, a sensor system may sense one or more conditions related to disordered breathing. Disordered breathing events may be detected based on the sensed conditions. Characteristics of the disordered breathing events such as severity, frequency, and/or duration, may be determined. Determination of the one or more characteristics of the sleep disordered breathing events may involve calculation of one or more indices characterizing the disordered breathing events. The indices may include, for example, an apnea/hypopnea index (AHI) and/or a percent time in periodic breathing (% PB), among other indices. The external respiratory therapy and the cardiac therapy maybe coordinated based on the characteristics of the disordered breathing events.

Figure 1B:
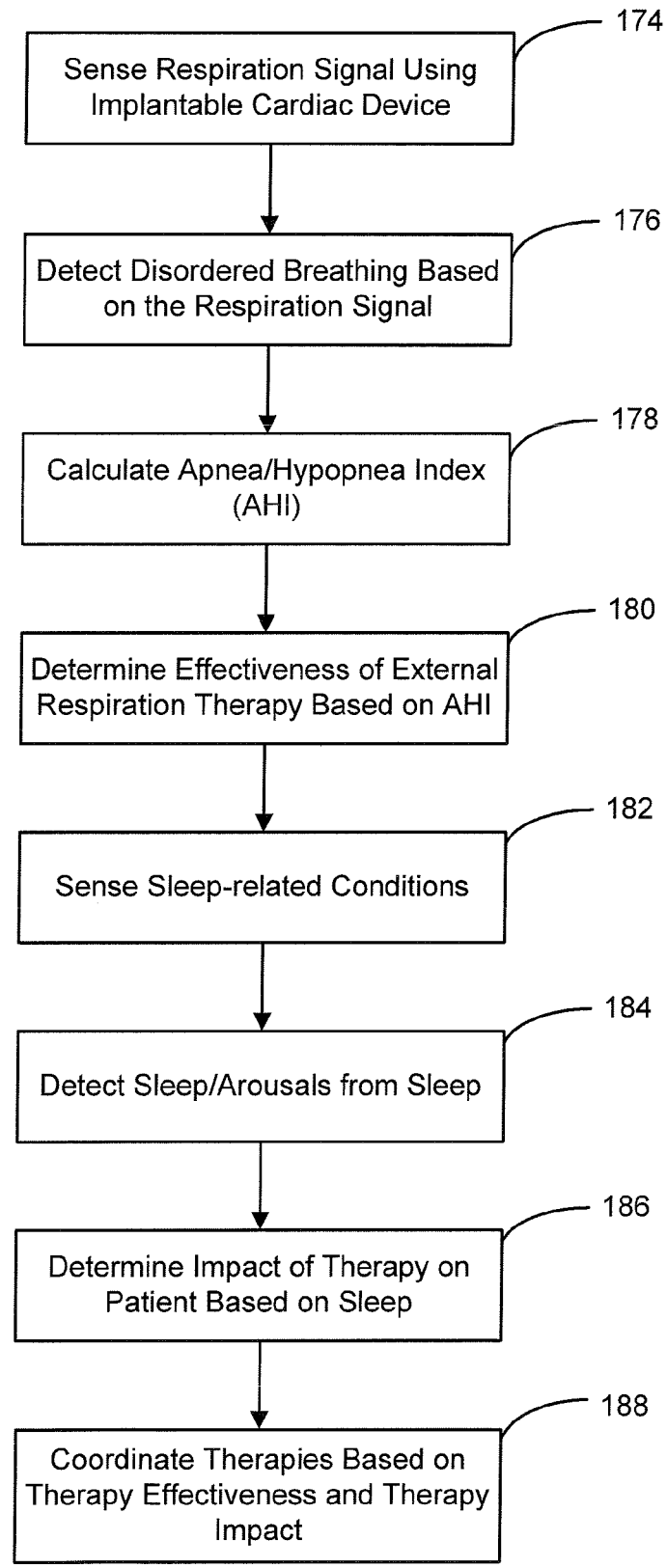

In accordance with an embodiment of the invention, illustrated in the flowchart of FIG. 1B, coordination of disordered breathing therapies, including an external respiratory therapy and a cardiac electrical stimulation therapy, may be implemented using circuitry disposed within the housing of an implantable cardiac rhythm management (CRM) device. The therapies delivered to the patient may be coordinated based on a variety of factors, including therapy effectiveness and/or impact of the therapy on the patient. In this embodiment, the external respiratory therapy is delivered by a continuous positive airway pressure (CPAP) device. The cardiac therapy comprises cardiac electrical stimulation therapy for treating disordered breathing delivered by the CRM device.

One or more sensors may be employed to sense conditions related to disordered breathing and/or disordered breathing therapy, including, for example, the effectiveness of the breathing therapy and/or the impact of the therapy on the patient. The sensors may be coupled to the CPAP device, the CRM device, or a first set of sensors may be coupled to the CPAP device and a second set coupled to the CRM device. The coordinating unit within the CRM device receives the signals from the sensors, determines therapy effectiveness and/or impact, and coordinates therapy delivered by the CPAP and CRM devices.

In one example, a condition modulated by patient respiration may be sensed 174 and a respiration waveform signal generated. Circuitry disposed within the housing of the CRM device may detect 176 disordered breathing episodes based on the respiration signal. The coordination unit may determine therapy effectiveness based on the severity, frequency and/or duration of sleep disordered breathing episodes experienced by the patient. In one implementation, coordination circuitry disposed within the CRM device may calculate 178 an apnea/hypopnea index (AHI) indicative of the frequency of disordered breathing episodes. The effectiveness of the sleep disordered breathing therapy may be determined 180 based on the sleep disordered breathing index. If the AHI is relatively low, the breathing therapy may be determined to be effective. If the AHI is relatively high, then the breathing therapy may be determined to be ineffective.

A CPAP device typically includes a respiratory mask, e.g., a nasal of facial mask, worn by the patient to facilitate delivery or air or other gas to the patient's airway. The respiratory mask may be inconvenient and/or uncomfortable for the patient to wear and may keep the patient awake. Further, delivery of positive airway pressure may inhibit sleep, or cause the patient to arouse frequently. Information about these side effects of the breathing therapy may be helpful in coordinating a therapy regimen for the patient.

Impact of the external breathing therapy and/or cardiac electrical stimulation therapy may be determined based on the patient's sleep quality. Sensors coupled to the coordination processor within the CRM device are configured to sense 182 one or more conditions related to sleep. The sleep related conditions are used to detect 184 sleep and/or arousals from sleep. The coordination processor within the CRM device determines 186 the impact of the therapies on the patient by monitoring the patient's sleep. For example, the coordination processing may monitor the total time the patient spends sleeping, the number of arousals experienced by the patient in one night, the number of arousals correlated to sleep disordered breathing events, the number of arousals correlated to therapy delivery, and/or the depth of the arousals. In various implementations the coordination processor may calculate various indices characterizing sleep and/or one or more composite indices based on indices related to sleep and indices related to sleep disordered breathing. In one example, the monitoring unit calculates the number of arousals experienced by the patient per hour (A/h).

Therapy coordination may be accomplished 188 based on the therapy effectiveness and impact information. Control signals may be transmitted from the coordinating processor unit to the therapy units of the CRM and CPAP devices. One or both of the therapies delivered by the CRM and CPAP devices may be adjusted to enhance therapy effectiveness and/or reduce side effects.

In various examples, coordinated disordered breathing therapy may involve adjusting the cardiac electrical stimulation therapy for disordered breathing, adjusting the neurostimulation therapy for disordered breathing and/or adjusting the external respiration therapy for disordered breathing. According to this scenario, a disordered breathing therapy coordination processor may distribute the burden of disordered breathing therapy between one or more therapy devices.

In one implementation, certain types of therapy may be used for predetermined periods of time. For example, a predetermined level of cardiac and/or nerve stimulation therapy may be used prior to the patient falling asleep. The therapy burden may be shifted to the external respiratory therapy device after sleep has been detected. In one implementation, the therapy burden may be distributed based on detected arousals. For example, if the delivery of one type of therapy causes the patient to arouse from sleep, the therapy burden may be shifted to other types of therapy to enhance the patient's sleep quality. Alternatively, rather than shifting to other types of therapy, therapy parameters of a particular therapy may be adjusted to provide more restful sleep. For example, an external respiratory therapy pressure may be adjusted downward to provide a disordered breathing therapy that is more comfortable to the patient and allows the patient to sleep better. In one implementation, the respiratory therapy pressure may be adjusted downward and the pacing rate may be adjusted upward to maintain effectiveness of the therapy while reducing an impact on the patient.

In another implementation, the therapy burden may be distributed based on therapy efficacy. In one scenario, the therapy controller may add therapies to the overall disordered breathing therapy regimen to improve therapy efficacy. For example, if the therapy coordination processor determines that disordered breathing is occurring despite the use of one type of therapy, additional one or more types of therapy may be added to the regimen in order to treat disordered breathing.

In one scenario, the disordered breathing therapy burden may be distributed based on device usage. For example, if the patient does not use the external respiratory therapy device, then the disordered breathing therapy coordination processor may signal a CRM device and/or an external respiratory therapy device to initiate or increase the level of therapy delivered by the CRM device, the external respiratory therapy device, and/or other therapy devices.

In one embodiment, the coordination processor may coordinate the disordered breathing therapy to enhance therapy efficacy while adjusting or avoiding a therapy impact. The coordination processor may acquire information related to the sensed conditions and may evaluate therapy efficacy and/or impact on the patient, i.e., side effects of the therapy, based on the sensed conditions. The coordination processor may modify the therapy delivered by one or more therapy devices to enhance therapy efficacy while reducing or avoiding side effects. The coordination processor may modify the therapy to reduce interactions between the disordered breathing therapy and other types of therapies delivered to the patient, e.g., neurostimulation for anti-hypertensive therapy and/or cardiac rhythm management. The coordination processor may modify the therapy to reduce interactions between different types of disordered breathing therapies, for example. The therapy controller may modify a therapy to increase the useable lifetime of an implantable device.

Figure 2:
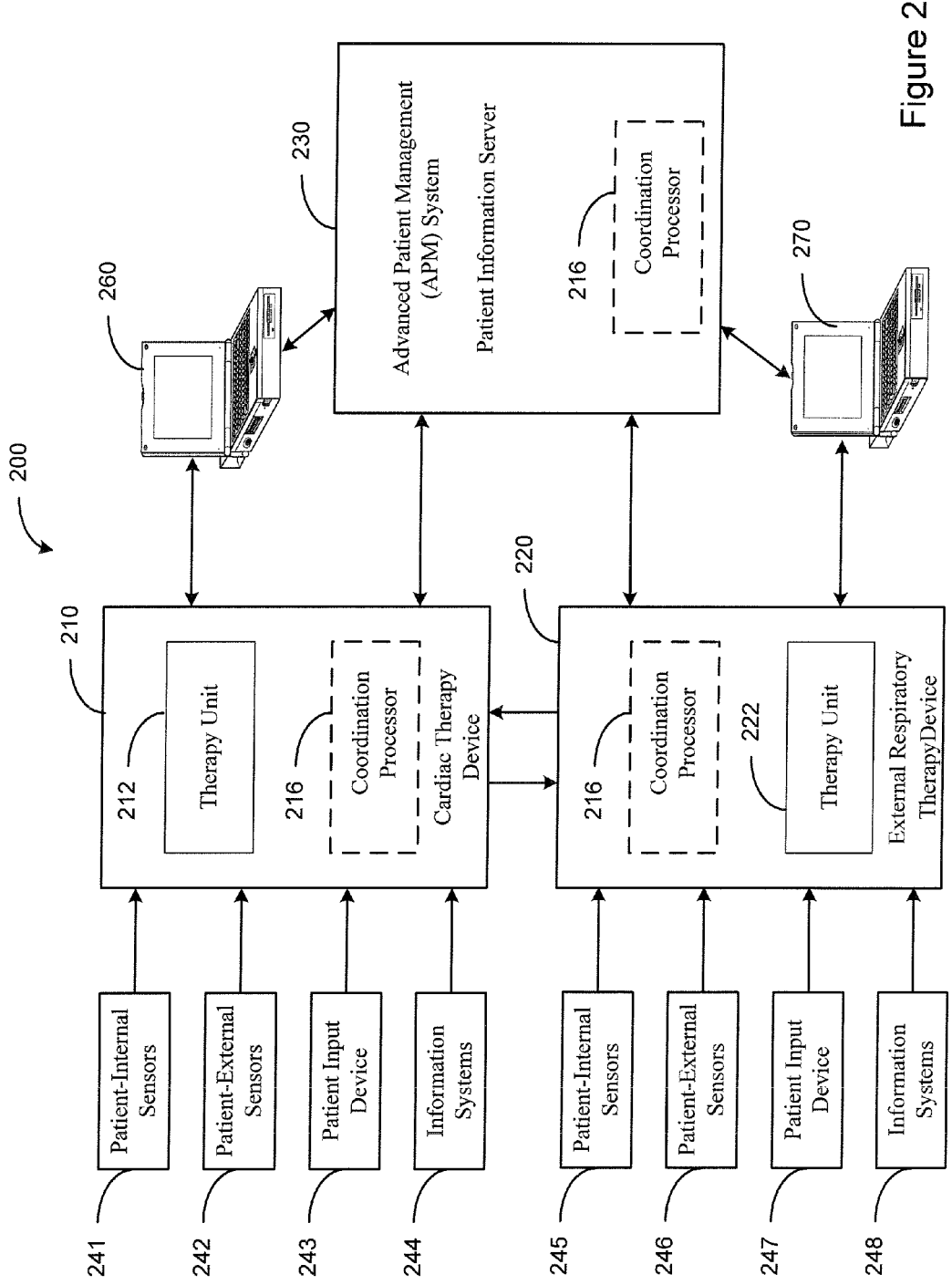
FIG. 2 is a block diagram of a medical system that may be used to implement coordinated disordered breathing therapy in accordance with embodiments of the invention.

FIG. 2 is a block diagram of a medical system 200 that may be used to implement coordinated disordered breathing therapy in accordance with embodiments of the invention. The medical system 200 may include, for example, a cardiac therapy device 210, an external respiratory therapy device 220 and an advanced patient management system 230.

The cardiac therapy device 210 may be a fully or partially implantable device including a therapy unit 212 coupled to one or more patient internal sensors 241, patient-external sensors 242, patient input device 243, and/or other information systems 244. The therapy unit 212 uses inputs from the patient internal sensors 241, patient-external sensors 242, patient input device 243, and/or other information systems 244 to monitor one or more patient conditions. In one embodiment, a therapy coordination processor 216 having circuitry disposed within the implantable housing of the cardiac therapy device 210 uses the sensed conditions to process and coordinate patient information that may be used to adjust the sleep disordered breathing therapy delivered to the patient by the external respiratory therapy device 220 and the cardiac therapy device 210. In another embodiment, the therapy coordination processor 216 is disposed within a separate device, such as a patient management server 230 of an APM system. In yet another embodiment, the therapy coordination processor 216 may be disposed within the external respiratory therapy device 220.

The external respiratory therapy device 220 may be positioned on the patient, near the patient, or in any location external to the patient. It is understood that a portion of a patient-external therapy device may be positioned within an orifice of the body, such as the nasal cavity or mouth, yet can be considered external to the patient (e.g., mouth pieces/appliances, tubes/appliances for nostrils, or temperature sensors positioned in the ear canal).

The external respiratory therapy device 220 and/or the APM device 230 may be coupled to one or more sensors 245, 246 and/or other information devices 247, 248. Information from the sensors 245, 246, e.g., flow sensors, pressure sensors, and/or other devices 247, 248 coupled to the external respiratory therapy device 220 and/or the APM device 230 may be combined with the information acquired by the cardiac therapy device 210 to develop and deliver a coordinated therapy.

In one implementation, the cardiac therapy device 210 is coupled to one or more patient-internal sensors 241 that are fully or partially implantable within the patient. The cardiac therapy device 210 may also be coupled to patient-external sensors 242 positioned on, near, or in a remote location with respect to the patient. The patient-internal 241 and patient-external 242 sensors may be used to sense various parameters, such as physiological or environmental parameters that may be used to develop coordinated disordered breathing therapies.

In some situations, the patient-internal sensors 241 may be coupled to the cardiac therapy device 210 through internal leads. In one example, an internal endocardial lead system may be used to couple cardiac electrodes to a cardiac therapy device 210 such as an implantable pacemaker or other cardiac device.

In some situations, one or more patient-internal sensors 241, patient external sensors 242, patient input devices 243, and/or other information systems 244 may be equipped with transceiver circuitry to support wireless communications with the cardiac therapy device 210. Similarly, one or more patient-internal sensors 245, patient external sensors 246, patient input devices 247, and/or other information systems 248 may be communicate wirelessly with the external respiratory therapy device 220.

The cardiac therapy device 210 and/or the external respiratory therapy device 220 may be coupled to patient-input devices 243, 247. The patient-input devices 243, 247 may be used to allow the patient to manually transfer information to the cardiac therapy device 210 and/or the external respiratory therapy device 220. The patient input devices 243, 247 may be particularly useful for inputting information concerning patient perceptions, such as how well the patient feels, and information such as patient smoking, drug use, or other activities that are not automatically sensed or detected by the medical sensors 241, 242, 245, 246 or information systems 244, 248.

The cardiac therapy device 210 and/or the external respiratory therapy device 220 may be connected to one or more information systems 244, 248, for example, a database system or server that acquires and/or stores information useful in connection with coordinating therapy functions of the cardiac therapy device 210 and the external respiratory therapy device 220. For example, the cardiac therapy device 210 or the external respiratory therapy device 220 may be coupled through a network to an information system server that provides information about environmental conditions affecting the patient, e.g., the pollution index for the patient's location.

In one embodiment, the cardiac therapy device 210 and the external respiratory therapy device 220 may be communicatively coupled through a wireless link. For example, the cardiac therapy device 210 and external respiratory therapy device 220 may be coupled through a short-range radio link, such as Bluetooth or a proprietary wireless link. The communications link may facilitate uni-directional or bi-directional communication between the cardiac therapy device 210 and the external respiratory therapy device 220. Data and/or control signals may be transmitted between the cardiac therapy device 210 and external respiratory therapy device 220 and can be used to modify disordered breathing therapy. For example, sensors of an external respiratory therapy device 220 may sense a set of patient conditions and the respiratory therapy device 220 may transmit the patient conditions to a coordination processor configured as a component of the cardiac therapy device 210. Alternatively, sensors of cardiac device 210 may sense a set of patient conditions and the cardiac therapy device 210 may transmit the patient conditions to a coordination processor configured as a component of the respiratory therapy device 220.

In an embodiment of the invention, the cardiac therapy and external respiratory therapy devices 210, 220 may be used within the structure of an advanced patient management (APM) system 230. As previously discussed, advanced patient management systems involve a system of medical devices that are accessible through various communications technologies. For example, patient data may be downloaded from one or more of the medical devices periodically or on command, and stored at a patient information server. The physician and/or the patient may communicate with the medical devices and the patient information server, for example, to acquire patient data or to initiate, terminate or modify therapy.

The APM patient information server 230 may be used to download and store data collected by the cardiac therapy device 210 and/or the external respiratory therapy device 220. In one implementation, the cardiac therapy device 210 and/or the external respiratory therapy device 220 may be communicatively coupled to device programmers 260, 270. The programmer 260 may provide indirect communication between the cardiac therapy device 210 and the patient information server 230. The programmer 270 may provide indirect communication between the external respiratory therapy device 220 and the patient information server 230. Information received by patient information server 230 can be processed in coordination processor 216 housed within one or more of the cardiac therapy device 210, the external respiratory therapy device 220 or patient information server 230 in order to develop coordinated disordered breathing therapy. Control signals generated by the coordination processor 216 can be sent to other therapy units 212, 222 within medical system 200. The control signals developed by coordination processor 216 direct the delivery of coordinated disordered breathing therapy.

In one implementation, the cardiac therapy and external respiratory therapy devices 210, 220 may not communicate directly, but may communicate indirectly through the APM system 230. In this embodiment, the APM system 230 may operate as an intermediary between two or more of the medical devices 210, 220.

Figure 3:
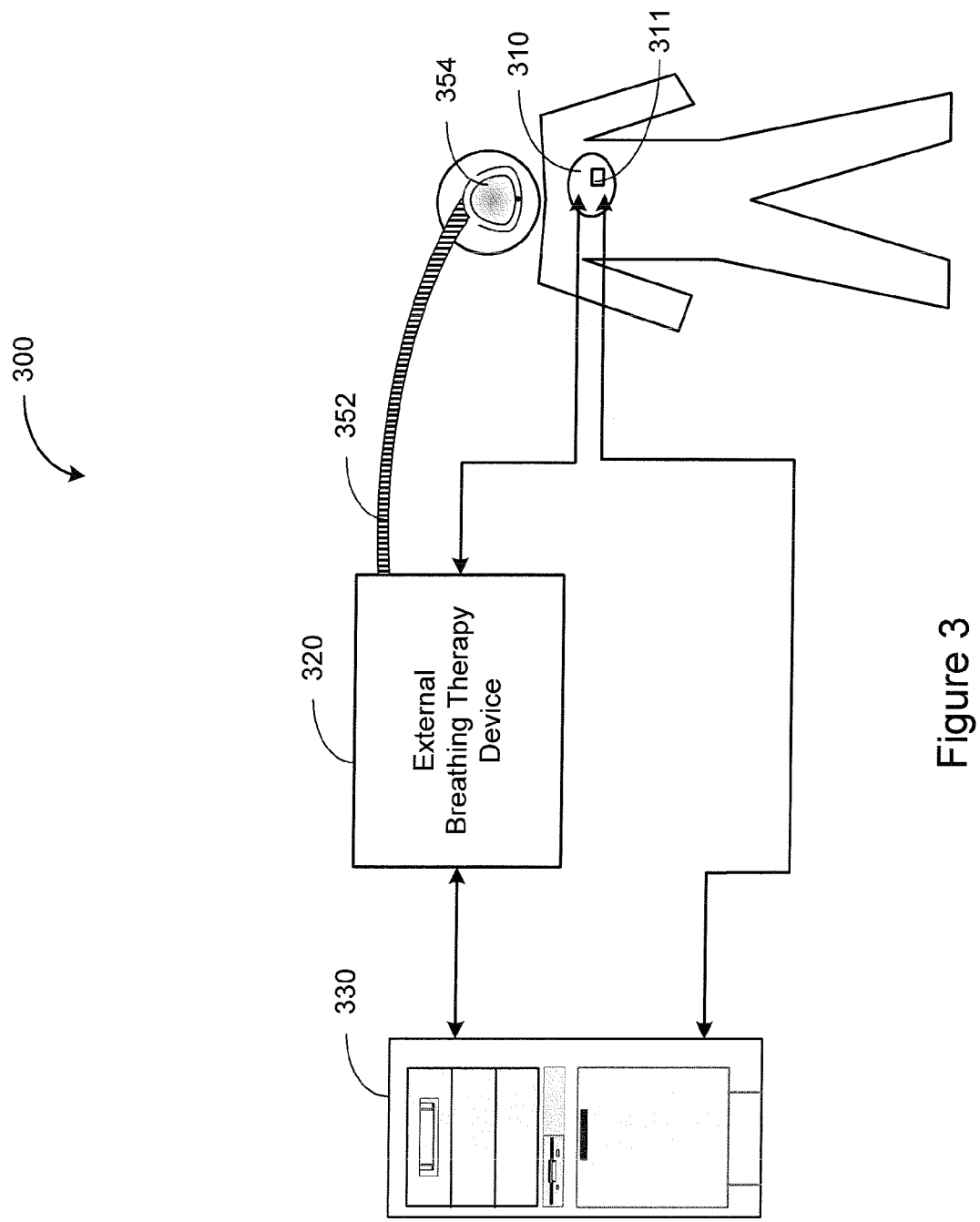
FIG. 3 illustrates a block diagram of a medical system that may be used to provide coordinated therapies for controlling sleep disordered breathing in accordance with embodiments of the invention.

FIG. 3 illustrates a block diagram of medical system 300 that may be used to provide coordinated therapies for controlling sleep disordered breathing in accordance with an embodiment of the invention. In this example, the medical system 300 includes a coordination processor 311 disposed within the housing of an implantable cardiac rhythm management (CRM) device 310. The coordination processor 311 utilizes information related to one or more patient conditions to coordinate disordered breathing therapies delivered by the external respiration therapy device 320 and the CRM device 310. The CRM device 310 may provide additional monitoring, diagnostic, and/or therapeutic functions to the patient, including, for example, cardiac pacing and/or defibrillation. The respiration therapy device 320 may provide additional monitoring, diagnostic and/or therapeutic functions beyond disordered breathing therapy to the patient.

The CRM device 310 may be electrically coupled to the patient's heart through electrodes placed in, on, or about the heart. The cardiac electrodes may sense cardiac signals produced by the heart and/or provide therapy to one or more heart chambers. For example, the cardiac electrodes may deliver electrical stimulation to one or more heart chambers, and/or to one or multiple sites within the heart chambers. The CRM 310 may directly control delivery of one or more cardiac therapies, such as cardiac pacing, defibrillation, cardioversion, cardiac resynchronization, and/or other cardiac therapies, for example.

The coordination processor 311 disposed within the CRM housing may be coupled to one or more patient internal sensors, patient external sensors, patient input devices, and/or information systems as described in connection with FIG. 2. A sensing system may sense various patient conditions associated with the patient's cardiovascular system, respiratory system, cardiopulmonary system, nervous system, muscle system, and/or other physiological systems. These conditions may be used to develop a coordinated disordered breathing therapy. The coordination processor 311 may also utilize various environmental or contextual conditions affecting the patient in order to develop a coordinated disordered breathing therapy.

In the example illustrated in FIG. 3, a medical system 300 comprises a positive airway pressure device 320 used to delivery disordered breathing therapy to a patient. Positive airway pressure devices may be used to provide a variety of respiration therapies, including, for example, continuous positive airway pressure (CPAP), bi-level positive airway pressure (bi-level PAP), proportional positive airway pressure (PPAP), auto-titrating positive airway pressure, ventilation, gas or oxygen therapies. All types of pressure devices are referred to generically herein as xPAP devices.

The xPAP device 320 develops a positive air pressure that is delivered to the patient's airway through tubing 352 and mask 354 connected to the xPAP device 320. Positive airway pressure devices are often used to treat disordered breathing, including central and/or obstructive disordered breathing types. In one configuration, for example, the positive airway pressure provided by the xPAP device 320 acts as a pneumatic splint keeping the patient's airway open and reducing the severity and/or number of occurrences of disordered breathing due to airway obstruction.

The coordination processor 311 may utilize one or more patient conditions sensed using sensors and/or input devices as described in connection with FIG. 2 to coordinate therapy delivered by the xPAP device with CRM therapies. Communication circuitry, e.g., communication circuitry disposed within the CRM device 310, may be used to transmit the coordinated disordered breathing therapy information directly to the xPAP device 320 through a wireless communications link, for example. Alternatively, the coordination processor 311 may transfer therapy coordination information to the xPAP 320 device indirectly through an APM system 330, as described above.

Methodologies involving the use of an implantable medical device to develop coordinated therapy for sleep disordered breathing are described in connection with FIG. 3. Although FIG. 3 depicts a coordination processor disposed within a CRM device, other configurations of coordination processors and/or therapy devices may alternatively or additionally be used. For example, other types of external respiration therapy devices, such as a nebulizer, respirator, ventilator or gas therapy device, may be used to treat sleep disordered breathing. Sleep disordered breathing therapy devices other than external respiratory therapy devices may alternatively or additionally be used. For example, the sleep disordered breathing therapy may involve a nerve stimulation therapy delivered by a nerve stimulation device, a muscle stimulation therapy delivered by a muscle stimulation device, a drug therapy delivered by a drug pump or other drug delivery device, a cardiac stimulation therapy delivered by a cardiac device, and/or other types of sleep disordered breathing therapy. Further, the coordination processor need not be disposed within the housing of a CRM device 310, and may comprise a stand alone coordination processor. Alternatively, the coordination processor 311 may be disposed within the housing of therapy devices other than a CRM device 310.

Figure 4A:
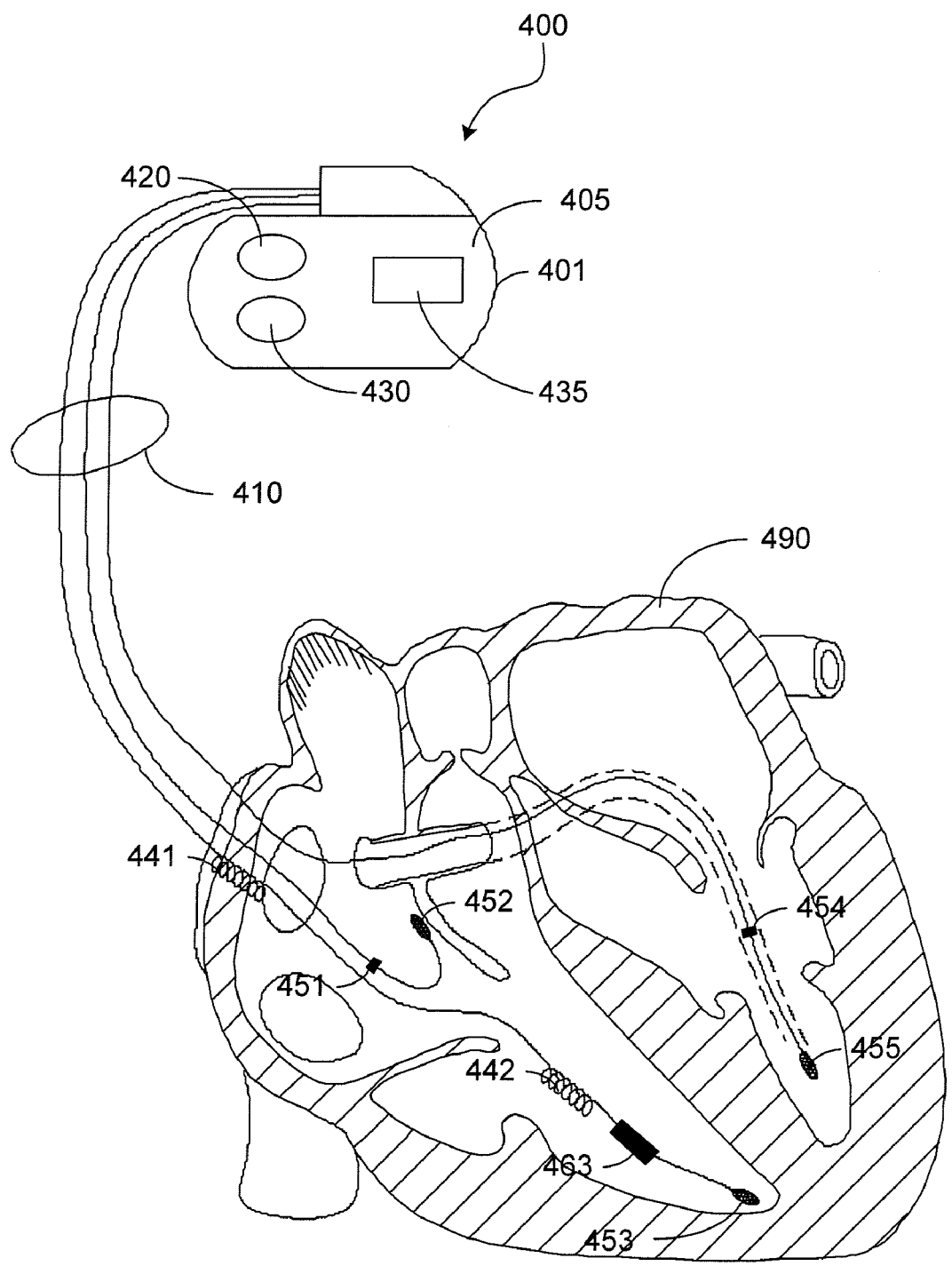
FIGS. 4A and 4B are partial views of an implantable device that may include circuitry for sensing and monitoring one or more patient conditions used for providing therapy coordination information for sleep disordered breathing in accordance with embodiments of the invention.

FIG. 4A is a partial view of an implantable device that may include circuitry for coordinating various therapies for sleep disordered breathing in accordance with embodiments of the invention. In this example, the coordination processor 435 is configured as a component of an implantable pulse generator 405 of a cardiac rhythm management (CRM) device 400. The implantable pulse generator 405 is electrically and physically coupled to an intracardiac lead system 410. The coordination processor 435 may alternatively be implemented in a variety of implantable monitoring, diagnostic, and/or therapeutic devices, such as an implantable cardiac monitoring device, an implantable drug delivery device, or an implantable neurostimulation device, for example.

Portions of the intracardiac lead system 410 are inserted into the patient's heart 490. The intracardiac lead system 410 includes one or more electrodes configured to sense electrical cardiac activity of the heart, deliver electrical stimulation to the heart, sense the patient's transthoracic impedance, and/or sense other physiological parameters, e.g., cardiac chamber pressure or temperature. Portions of the housing 401 of the pulse generator 405 may optionally serve as a can electrode.

Communications circuitry is disposed within the housing 401, facilitating communication between the pulse generator 405 including the coordination processor 435 and an external device, such as a sleep disordered breathing therapy device and/or APM system. The communications circuitry can also facilitate unidirectional or bidirectional communication with one or more implanted, external, cutaneous, or subcutaneous physiologic or non-physiologic sensors, patient-input devices and/or information systems.

The pulse generator 405 may optionally incorporate a motion sensor 420. The motion sensor may be configured, for example, to sense patient activity. Patient activity may be used in connection with sleep detection as described in more detail herein. The motion sensor 420 may be implemented as an accelerometer positioned in or on the housing 401 of the pulse generator 405. If the motion sensor 420 is implemented as an accelerometer, the motion sensor 420 may also provide acoustic information, e.g. rales, coughing, S1-S4 heart sounds, cardiac murmurs, and other acoustic information.

The lead system 410 of the CRM device 400 may incorporate a transthoracic impedance sensor that may be used to acquire the patient's respiration waveform, or other respiration-related information. The transthoracic impedance sensor may include, for example, one or more intracardiac electrodes 441, 442, 451-455, 463 positioned in one or more chambers of the heart 490. The intracardiac electrodes 441, 442, 451-455, 463 may be coupled to impedance drive/sense circuitry 430 positioned within the housing of the pulse generator 405.

In one implementation, impedance drive/sense circuitry 430 generates a current that flows through the tissue between an impedance drive electrode 451 and a can electrode on the housing 401 of the pulse generator 405. The voltage at an impedance sense electrode 452 relative to the can electrode changes as the patient's transthoracic impedance changes. The voltage signal developed between the impedance sense electrode 452 and the can electrode is detected by the impedance sense circuitry 430. Other locations and/or combinations of impedance sense and drive electrodes are also possible. The impedance signal may also be used to detect other physiological changes besides respiration that result in a change in impedance, including pulmonary edema, heart size, cardiac pump function, etc. The respiratory and/or pacemaker therapy may be altered on the basis of the patient's heart condition as sensed by impedance.

Figure 7:
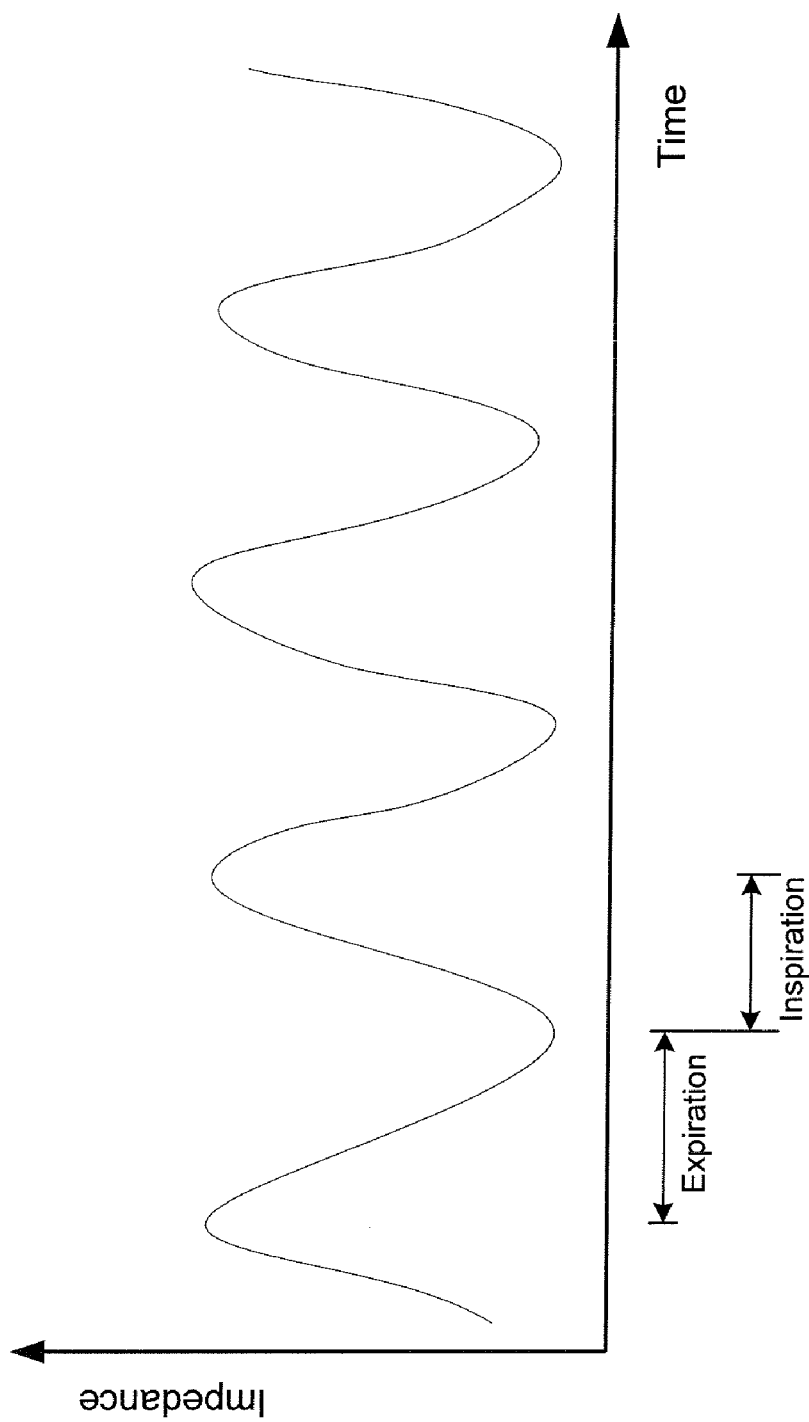
FIG. 7 is a graph of a respiration signal measured by a transthoracic impedance sensor that may be utilized for monitoring parameters of breathing therapy in accordance with embodiments of the invention.

The voltage signal developed at the impedance sense electrode 452, illustrated in FIG. 7, is proportional to the patient's transthoracic impedance and represents the patient's respiration waveform. The transthoracic impedance increases during respiratory inspiration and decreases during respiratory expiration. The transthoracic impedance may be used to determine the amount of air moved in one breath, denoted the tidal volume and/or the amount of air moved per minute, denoted the minute ventilation. A normal "at rest" respiration pattern, e.g., during non-REM sleep, includes regular, rhythmic inspiration-expiration cycles without substantial interruptions, as indicated in FIG. 7.

Returning to FIG. 4A, the lead system 410 may include one or more cardiac pace/sense electrodes 451-455 positioned in, on, or about one or more heart chambers for sensing electrical signals from the patient's heart 490 and/or delivering pacing pulses to the heart 490. The intracardiac sense/pace electrodes 451-455, such as those illustrated in FIG. 4A, may be used to sense and/or pace one or more chambers of the heart, including the left ventricle, the right ventricle, the left atrium and/or the right atrium. The lead system 410 may include one or more defibrillation electrodes 441, 442 for delivering defibrillation/cardioversion shocks to the heart.

The pulse generator 405 may include circuitry for detecting cardiac arrhythmias and/or for controlling pacing or defibrillation therapy in the form of electrical stimulation pulses or shocks delivered to the heart through the lead system 410. The coordination processor 435, including sensor interface circuitry, event detectors, processor circuitry, and/or memory circuitry, as described in connection with the FIG. 6, may be disposed within the housing 401 of the pulse generator 405. The coordination processor 435 may be coupled to various sensors, including the transthoracic impedance sensor 430 and motion sensor 420, patient input devices, and/or information systems through leads or through wireless communication links.

The coordination processor 435 may use the information generated by the various sensors in order to develop information for coordination of sleep disordered breathing therapy. In one embodiment, the therapy coordination processor may be positioned outside the pulse generator housing 401 and communicatively coupled to the pulse generator 405 within generator housing 401, e.g., through a wireless communications link.

Figure 4B:
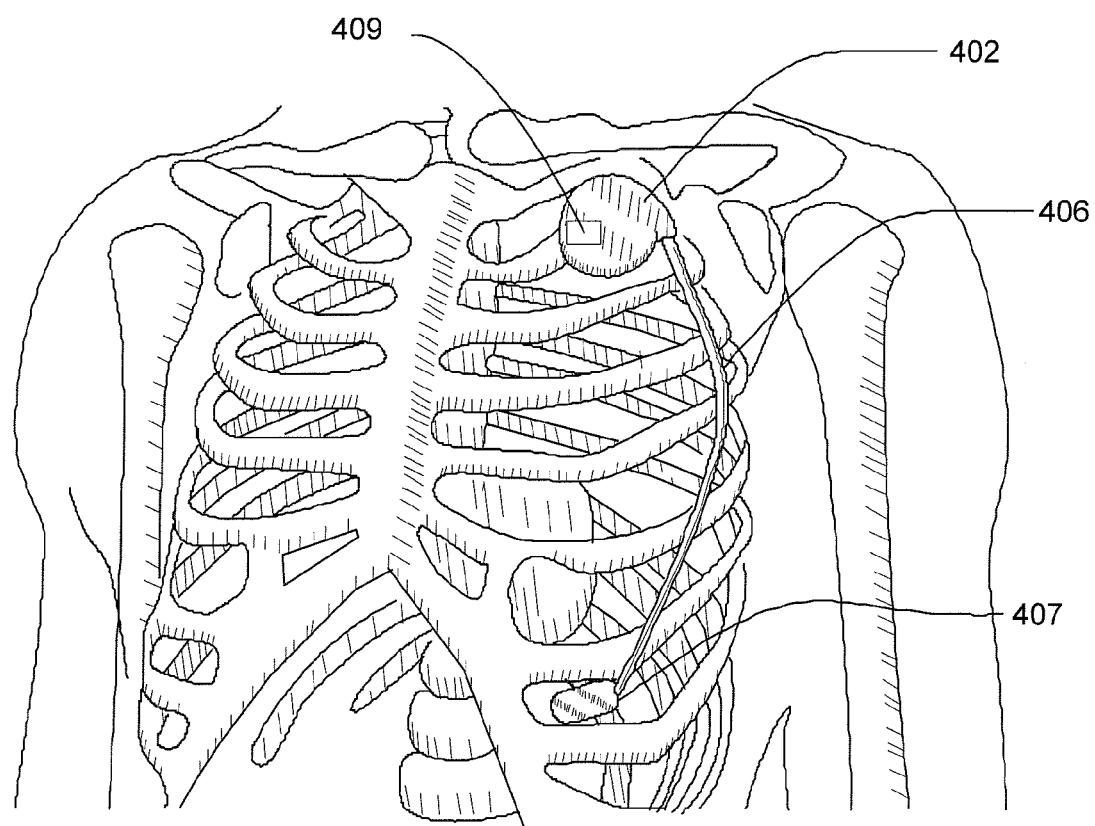

FIG. 4B is a diagram illustrating an implantable transthoracic cardiac device that may be used in connection with developing coordinated therapies for sleep disordered breathing in accordance with embodiments of the invention. The implantable device illustrated in FIG. 4B is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

Circuitry for implementing a disordered breathing therapy coordination processor may be positioned within the primary housing of the ITCS device. The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature.

In another implementation, one or more electrodes may be located in direct contact with the heart, great vessel or coronary vasculature, such as via one or more leads implanted by use of conventional transvenous delivery approaches. In another implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart.

In the configuration shown in FIG. 4B, a subcutaneous electrode assembly 407 can be positioned under the skin in the chest region and situated distal from the housing 402. The subcutaneous and, if applicable, housing electrode(s) can be positioned about the heart at various locations and orientations, such as at various anterior and/or posterior locations relative to the heart. The subcutaneous electrode assembly 407 is coupled to circuitry within the housing 402 via a lead assembly 406. One or more conductors (e.g., coils or cables) are provided within the lead assembly 406 and electrically couple the subcutaneous electrode assembly 407 with circuitry in the housing 402. One or more sense, sense/pace or defibrillation electrodes can be situated on the elongated structure of the electrode support, the housing 402, and/or the distal electrode assembly (shown as subcutaneous electrode assembly 407 in FIG. 4B).

It is noted that the electrode and the lead assemblies 407, 406 can be configured to assume a variety of shapes. For example, the lead assembly 406 can have a wedge, chevron, flattened oval, or a ribbon shape, and the subcutaneous electrode assembly 407 can comprise a number of spaced electrodes, such as an array or band of electrodes. Moreover, two or more subcutaneous electrode assemblies 407 can be mounted to multiple electrode support assemblies 406 to achieve a desired spaced relationship amongst subcutaneous electrode assemblies 407.

In particular configurations, the ITCS device may perform functions traditionally performed by cardiac rhythm management devices, such as providing various cardiac monitoring, pacing and/or cardioversion/defibrillation functions. Exemplary pacemaker circuitry, structures and functionality, aspects of which can be incorporated in an ITCS device of a type that may benefit from multi-parameter sensing configurations, are disclosed in commonly owned U.S. Pat. Nos. 4,562,841; 5,284,136; 5,376,476; 5,036,849; 5,540,727; 5,836,987; 6,044,298; and 6,055,454, which are hereby incorporated herein by reference in their respective entireties. It is understood that ITCS device configurations can provide for non-physiologic pacing support in addition to, or to the exclusion of, bradycardia and/or anti-tachycardia pacing therapies. Exemplary cardiac monitoring circuitry, structures and functionality, aspects of which can be incorporated in an ITCS of the present invention, are disclosed in commonly owned U.S. Pat. Nos. 5,313,953; 5,388,578; and 5,411,031, which are hereby incorporated herein by reference in their respective entireties.

An ITCS device can incorporate circuitry, structures and functionality of the subcutaneous implantable medical devices disclosed in commonly owned U.S. Pat. Nos. 5,203,348; 5,230,337; 5,360,442; 5,366,496; 5,397,342; 5,391,200; 5,545,202; 5,603,732; 5,916,243; 7,570,997; and commonly owned U.S. Patent Application No. 60/462,272 and U.S. Publication Nos. 2004/0230229, 2004/0230230, and 2004/0215240, which are incorporated herein by reference.

The housing of the ITCS device may incorporate components of a coordination processor 409. The coordination processor 409 may be coupled to one or more sensors, patient input devices, and/or information systems as described in connection with FIG. 2.

In one implementation, the ITCS device may include an impedance sensor configured to sense the patient's transthoracic impedance. The impedance sensor may include the impedance drive/sense circuitry incorporated with the housing 402 of the ITCS device and coupled to impedance electrodes positioned on the can or at other locations of the ITCS device, such as on the subcutaneous electrode assembly 407 and/or lead assembly 406. In one configuration, the impedance drive circuitry generates a current that flows between a subcutaneous impedance drive electrode and a can electrode on the primary housing of the ITCS device. The voltage at a subcutaneous impedance sense electrode relative to the can electrode changes as the patient's transthoracic impedance changes. The voltage signal developed between the impedance sense electrode and the can electrode is sensed by the impedance drive/sense circuitry.

Communications circuitry is disposed within the housing 402 for facilitating communication between the ITCS device, including the coordination processor 409, and an external therapy device, e.g., external respiratory therapy device, or other device such as a portable or bed-side communication station, patient-carried/worn communication station, or external programmer, for example. The communications circuitry can also facilitate unidirectional or bidirectional communication with one or more external, cutaneous, or subcutaneous physiologic or non-physiologic sensors.

Figure 5:
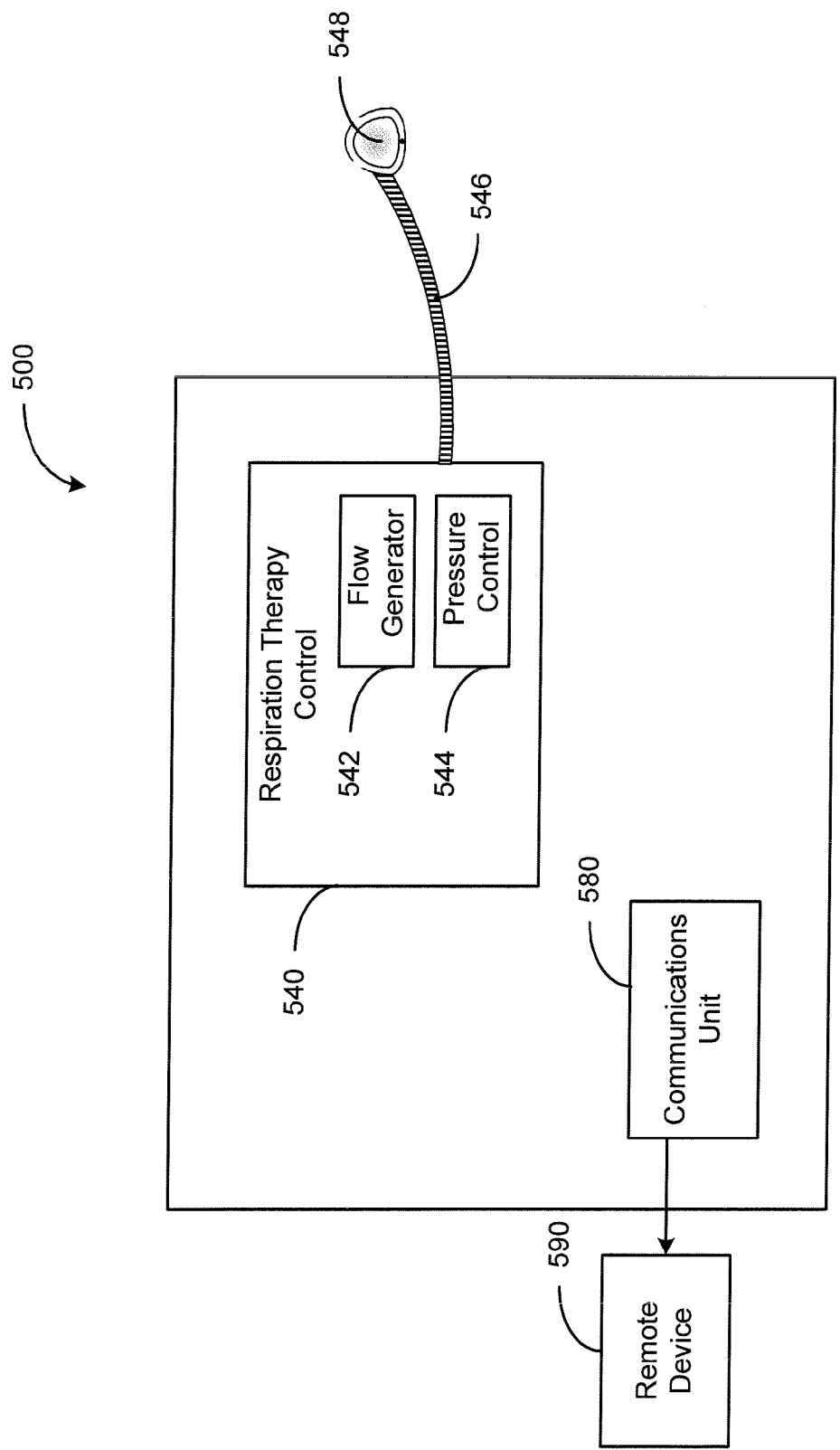
FIG. 5 is a block diagram of a patient-external respiratory therapy device that may be utilized in a system providing coordinated sleep disordered breathing therapy in accordance with embodiments of the invention.

FIG. 5 illustrates a block diagram of a sleep disordered breathing therapy device 500, e.g., xPAP device that may be used to provide therapy in accordance with embodiments of the invention. An implantable therapy coordination device, implemented as a component of the CRM or ITCS systems described in connection with FIGS. 4A and 4B, respectively, may collect information used for coordinating sleep disordered breathing therapy. Other types of sleep disordered breathing therapy devices may alternatively or additionally be employed within the context of the present invention. For example, sleep disordered breathing therapy may be provided by a muscle stimulation device, a nerve stimulation device, a drug delivery device, and/or other devices that can be used in coordination to treat sleep disordered breathing.

As previously discussed, the xPAP device 500 may include any of the positive airway pressure devices, including CPAP, bi-level positive airway pressure (bi-PAP), proportional positive airway pressure (PPAP), and/or autotitration positive airway pressure devices, for example. Continuous positive airway pressure (CPAP) devices deliver a set air pressure to the patient. The pressure level for the individual patient may be determined during a titration study. Such a study may take place in a sleep lab, and involves determination of the optimum airway pressure by a sleep physician or other professional. The CPAP device pressure control is set to the determined level. When the patient uses the CPAP device, a substantially constant airway pressure level is maintained by the device.

Autotitration PAP devices are similar to CPAP devices, however, the pressure controller for autotitration devices automatically determines the air pressure for the patient. Instead of maintaining a constant pressure, the autotitration PAP device evaluates sensor signals and the changing needs of the patient to deliver a variable positive airway pressure. Autotitration PAP and CPAP are often used to treat sleep disordered breathing, for example.

Bi-level positive airway pressure (bi-PAP) devices provide two levels of positive airway pressure. A higher pressure is maintained while the patient inhales. The device switches to a lower pressure during expiration. Bi-PAP devices are used to treat a variety of respiratory dysfunctions, including chronic obstructive pulmonary disease (COPD), respiratory insufficiency, and ALS or Lou Gehrig's disease, among others.

Sleep disordered breathing therapy may be provided by a servo ventilation device. Servo ventilation devices provide airway pressure dependent on the respiration cycle stage. A servo ventilation device provides positive pressure on inhalation and negative pressure on exhalation.

The breathing therapy control unit 540 includes a flow generator 542 that pulls in air through a filter. The flow generator 542 is controlled by the pressure control circuitry 544 to deliver an appropriate air pressure to the patient. Air flows through tubing 546 coupled to the xPAP device 500 and is delivered to the patient's airway through a mask 548. In one example, the mask 548 may be a nasal mask covering only the patient's nose. In another example, the mask 548 covers the patient's nose and mouth.

The xPAP device 500 may include a communications unit 580 for communicating with one or more separate devices, including patient-external and/or patient-internal monitoring, diagnostic and/or therapeutic devices 590. In one example, the xPAP device 500 may receive therapy coordination information from a coordination processor disposed within an implantable monitoring and/or therapy device. In another example, the xPAP device 500 may receive therapy coordination information from a patient management server or other computing device coupled to the medical device.

Figure 6:
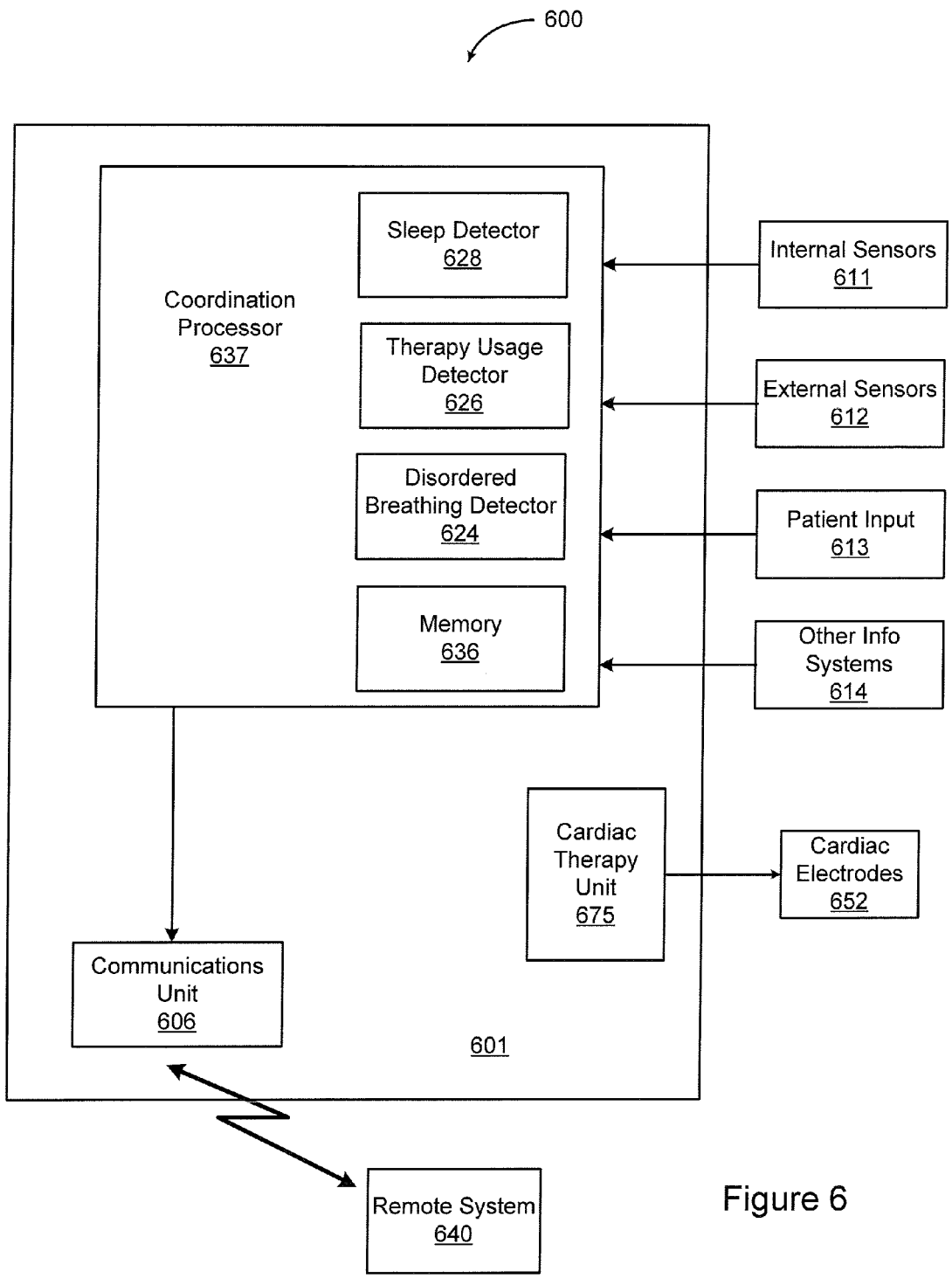
FIG. 6 is a block diagram of an implantable medical device including a cardiac therapy pulse generator that may be utilized in a system delivering coordinated disordered breathing therapy in accordance with embodiments of the invention.

The block diagram of FIG. 6 illustrates an example of system 600 including a fully or partially implantable device 601 that may be used to monitor patient conditions and to coordinate sleep disordered breathing therapy in accordance with embodiments of the invention. The medical device 601 may be coupled to an array of data acquisition devices, including patient-internal sensors 611, patient-external sensors 612, patient input devices 613, and/or other information systems 614 as described in more detail above.

Patient conditions monitored by the implantable device 601 may include both physiological and non-physiological contextual conditions affecting the patient. Physiological conditions may include a broad category of conditions associated with the internal functioning of the patient's physiological systems, including the cardiovascular, respiratory, nervous, muscle and other systems. Examples of physiological conditions include blood chemistry, patient posture, patient activity, respiration quality, sleep quality, among others.

Contextual conditions are non-physiological conditions representing patient-external or background conditions. Contextual conditions may be broadly defined to include, for example, present environmental conditions, such as patient location, ambient temperature, humidity, air pollution index. Contextual conditions may also include historical/background conditions relating to the patient, including the patient's normal sleep time and the patient's medical history, for example. Methods and systems for detecting some contextual conditions, including, for example, proximity to bed detection, are described in commonly owned U.S. Pat. No. 7,400,928, which is incorporated herein by reference.

Table 1 provides a representative set of patient conditions that may be monitored by the device 601 in accordance with embodiments of the invention. Table 1 also provides illustrative sensing methods that may be employed to sense the conditions. It will be appreciated that patient conditions and detection methods other than those listed in Table 1 may be used and are considered to be within the scope of the invention.

TABLE 1

| Condition Type | | Condition | Sensor type or Detection method |
|---|---|---|---|
| Physiological | Cardiovascular System | Heart rate<br>Heart rate variability<br>QT interval | EGM, ECG |
| | | Ventricular filling pressure | Intracardiac pressure sensor |
| | | Blood pressure | Blood pressure sensor |
| | Respiratory System | Snoring | Accelerometer Microphone |
| | | Respiration pattern (Tidal volume Minute ventilation Respiratory rate) | Transthoracic impedance sensor (AC) |
| | | Patency of upper airway | Intrathoracic impedance sensor |
| | | Pulmonary congestion | Transthoracic impedance sensor (DC) |
| | Nervous System | Sympathetic nerve activity | Muscle sympathetic nerve Activity sensor |
| | | Brain activity | EEG |
| | Blood Chemistry | CO2 saturation<br>O2 saturation<br>Blood alcohol content<br>Adrenalin<br>Brain Natriuretic Peptide (BNP)<br>C-Reactive Protein<br>Drug/Medication/<br>Tobacco use | Blood analysis |
| | Muscle System | Muscle atonia | EMG |
| | | Eye movement | EOG |
| | | Patient activity | Accelerometer, MV, etc |
| | | Limb movements | Accelerometer, EMG |
| | | Jaw movements | Accelerometer, EMG |
| | | Posture | Multi-axis accelerometer |
| Contextual | Environmental | Ambient temperature | Thermometer |
| | | Humidity | Hygrometer |
| | | Pollution | Air quality website |
| | | Time | Clock |
| | | Barometric pressure | Barometer |
| | | Ambient noise | Microphone |
| | | Ambient light | Photodetector |
| | | Altitude | Altimeter |
| | | Location | GPS, proximity sensor |
| | | Proximity to bed | Proximity to bed sensor |
| | Historical/ Background | Historical sleep time | Patient input, previously detected sleep onset times |
| | | Medical history<br>Age<br>Recent exercise<br>Weight<br>Gender<br>Body mass index | Patient input |

TABLE 1-continued

| Condition Type | Condition | Sensor type or Detection method |
|---|---|---|
| | Neck size<br>Emotional state<br>Psychological history<br>Daytime sleepiness<br>Patient perception of sleep quality<br>Drug, alcohol, nicotine use | |

The implantable device 601 of FIG. 6 includes a coordination processor 637 for processing signals received from the sensors, 611, 612, patient input devices 613, and/or other information system 614. The coordination processor 637 may include one or more a detection units 624, 626, 628 that detect the occurrence of various physiological events. For example, the coordination processor 637 may include one or more of a disordered breathing detector 624, a sleep detector 628, and/or a therapy usage detector 626. Other event detection components may also be included. The coordination processor 637 may be used to calculate various indices, e.g., AHI, % PB, and/or arousals per unit time, used for evaluating therapy efficacy, and/or therapy impact. The coordination processor 637 may compare the patient's therapy usage to a prescribed therapy to determine therapy compliance. The coordination processor 637 can develop control signals for implementing a coordinated therapy based on the monitored conditions, the detected events, and/or the calculated indices.

In one exemplary implementation, the disordered breathing detector 624 may be coupled to a respiration sensor. The disordered breathing detector 624 may use the respiration signal developed by the respiration sensor to detect disordered breathing events based on the inspiratory and expiratory phases of the patient's respiration cycles, for example. The sleep detector 628 may analyze various inputs from the patient-internal sensors 611, patient-external sensors 612, patient input devices 613, other information systems 614 to detect sleep-related events, including, for example, sleep onset, sleep offset, sleep stages, and arousals from sleep.

The coordination processor 637 may include a memory 636 for storing information derived from signals produced by the patient-internal sensors 611, patient-external sensors 612, patient input devices 613, and/or other information systems 614. The memory 636 may also store information about detected events, e.g., sleep and disordered breathing events, and/or information related to calculated indices characterizing various events such as sleep and/or disordered breathing events. The stored data may be used by coordination processor 637 to develop a coordinated disordered breathing therapy. The stored data may be retrieved by another component of the medical device 601 for later use, or may be transmitted to a separate device 640 for storage, further processing, trending, analysis and/or display, for example. In one scenario, the stored data can be downloaded to a separate device periodically or on command. The stored data may be presented to the patient's health care professional on a real-time basis, or as a long-term, e.g., month long or year long, trend of daily measurements.

In the particular embodiment illustrated in FIG. 6, the medical device 601 includes a cardiac therapy unit 675. This example, the medical device 601 comprises a cardiac therapy device 675 configured as a cardiac pulse generator to deliver cardiac electrical stimulation therapy via electrical stimulation electrodes 652.

The medical device 601 may further include a communications unit 606 that controls communications between the medical device 601 and other devices or systems. For example, the communications unit 606 may be used to provide wireless or wired communications links between the medical device 601 and one or more of the patient-internal sensors 611, patient-external sensors 612, patient input devices 613, and information systems 614.

The communications unit 606 may also facilitate communications between the medical device 601 and a remote device 640 such as another sleep disordered breathing therapy device, a programmer, and/or an APM system. The wireless connections coupling the medical device 601 to various other devices and systems may utilize a variety of wireless protocols, including, for example, Bluetooth, IEEE 802.11, and/or a proprietary wireless protocol.

Detecting the onset, termination, duration, stages, and quality of sleep experienced by a patient may be employed in connection with constructing a coordinated disordered breathing therapy. Patients suffering from sleep apnea, or other types of sleep disordered breathing, may be treated for sleep disordered breathing only during periods of sleep. Coordinating disordered breathing therapy may involve determining if the patient is asleep and/or detecting various sleep-related processes, such as arousals from sleep and/or REM or non-REM sleep stages.

In addition, information associated with patient sleep may be used to assess an impact of breathing therapy on the patient. Therapy impact data may be used to develop information to coordinate and adjust the therapy. The implantable monitoring device 601 may include a sleep detector 628 for detecting when the patient is asleep and various stages and/or processes of sleep. Various methods of sleep detection implementable in an implanted device involve sensing one or more conditions indicative of sleep. The sleep-related conditions may be compared to one or more thresholds to determine if the patient is asleep.

The sleep-related conditions may be sensed or derived using patient-external or implantable sensors and analyzed by a sleep detector coupled to or incorporated in the implantable therapy coordination device. For example, sleep detection may be implemented in an implantable cardiac rhythm management system configured as a pacemaker/defibrillator and incorporating a coordination processor as illustrated in FIG. 4A or the ITCS device illustrated in FIG. 4B.

Sleep detection may involve sensing one or more conditions indicative of sleep. A representative set of sleep-related conditions include body movement, heart rate, QT interval, eye movement, respiration rate, transthoracic impedance, tidal volume, minute ventilation, body posture, brain activity, cardiac activity, muscle tone, body temperature, time of day, historical sleep times, blood pressure, and blood gas concentration, proximity to bed, for example.

Sleep may be detected by comparing levels of the one or more sleep-related conditions to one or more sleep thresholds. For example, sleep may be detected by monitoring the patient's heart rate. When the patient's heart rate decreases below a sleep threshold, the patient may be determined to be asleep. Sleep may also be detected by monitoring the patient's activity. If the patient's activity decreases below a sleep threshold, then the patient may be determined to be asleep. Another method of detecting sleep involves monitoring the patient's minute ventilation. If the patient's minute ventilation falls below a sleep threshold, then the patient may be determined to be asleep.

Sleep may be detected by comparing multiple sleep-related conditions to multiple thresholds. For example, the patient may be determined to be asleep if the patient's activity, sensed by an accelerometer, falls below an activity sleep threshold and the patient's heart rate, sensed by cardiac electrodes, falls below a heart rate sleep threshold.

Sleep may also be detected using one sleep-related condition to modify the sleep threshold of another sleep-related condition. A first sleep-related condition may be sensed. The level of the sleep-related condition may be compared to a sleep threshold to determine the onset and termination of sleep. A second sleep-related condition may be used to adjust the sleep threshold. Additional sleep-related conditions may optionally be sensed to confirm the onset or termination of the sleep condition.

A sleep detector 628 (FIG. 6) may be configured to compare the levels of one or more sleep-related conditions to one or more thresholds. In one implementation, the one sleep related condition may be compared to a sleep threshold or other index to detect sleep. In another implementation, multiple sleep-related conditions may be compared to multiple thresholds or indices. In a further implementation, one or more of the sleep-related conditions may be used to adjust the sleep thresholds or indices. Furthermore, the onset or termination of sleep may be confirmed using an additional number of sleep-related conditions.

The sleep-related conditions may be sensed using implantable sensors and/or patient-external sensors, for example. In one embodiment, patient activity may be compared to a sleep threshold to determine when the patient is asleep. A low level of activity is indicative that the patient is sleeping. Patient activity may be sensed, for example, using an accelerometer positioned on or in the housing of an implantable cardiac device, or in another convenient location. The accelerometer signal may be correlated with activity level or workload.

A second sleep-related condition may be used to adjust the sleep threshold. In one embodiment, the patient's minute ventilation is used to adjust the sleep threshold. The patient's respiration may be sensed using a transthoracic impedance sensor. Transthoracic impedance may be used to derive various parameters associated with respiration, including, for example, tidal volume and/or minute ventilation. A transthoracic impedance sensor may be integrated into an implantable cardiac device with intracardiac electrodes, for example. Impedance driver circuitry generates a current that flows through the blood between the impedance drive electrode and a can electrode on the housing of the cardiac device. The voltage at an impedance sense electrode relative to the can electrode changes as the transthoracic impedance changes.

The voltage signal developed at the impedance sense electrode, illustrated in FIG. 7, is proportional to the transthoracic impedance, with the impedance increasing during respiratory inspiration and decreasing during respiratory expiration. The peak-to-peak transition of the impedance, illustrated in FIG. 7, is proportional to the amount of air inhaled in one breath, denoted the tidal volume. The variations in impedance during respiration may be used to determine the respiration tidal volume, corresponding to the volume of air moved in a breath, or minute ventilation corresponding to the amount of air moved per minute.

Figure 8:
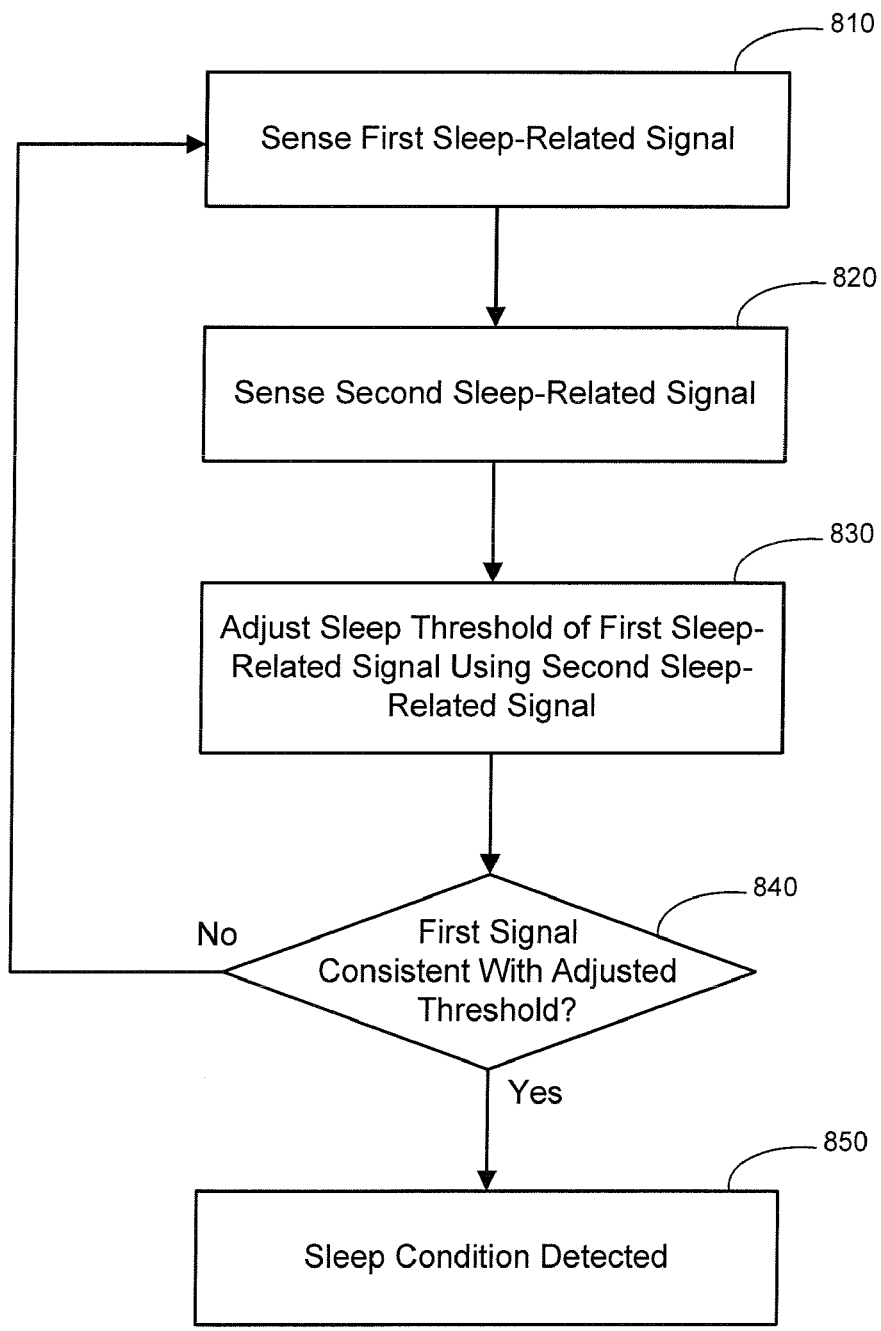
FIG. 8 is a flowchart illustrating a method of detecting sleep according to embodiments of the invention.

FIG. 8 is a flowchart illustrating a method of detecting sleep according to an embodiment of the invention. A sleep threshold associated with a first sleep-related condition is established. The sleep threshold may be determined from clinical data of a sleep threshold associated with sleep acquired using a group of subjects, for example. The sleep threshold may also be determined using historical data taken from the particular patient for whom onset and offset of sleep is to be determined. For example, a history of a particular patient's sleep times can be stored, and a sleep threshold can be developed using data associated with the patient's sleep time history.

First and second signals associated with sleep-related conditions are sensed 810, 820. The first and the second signals may be any signal associated with the condition of sleep, such as the representative sleep-related conditions associated with sleep listed above.

The sleep threshold established for the first signal is adjusted 830 using the second signal. For example, if the second signal indicates condition, e.g., high level of patient activity that is incompatible with a sleep state, the sleep threshold of the first signal may be adjusted downward to require sensing a decreased level of the first signal before a sleep condition is detected.

If the first signal is consistent with sleep according to the adjusted sleep threshold 840, a sleep condition is detected 850. If the first signal is not consistent with sleep using the adjusted sleep threshold, the first and the second signals continue to be sensed 810, 820 and the threshold adjusted 830 until a condition of sleep is detected 850.

Figure 9:
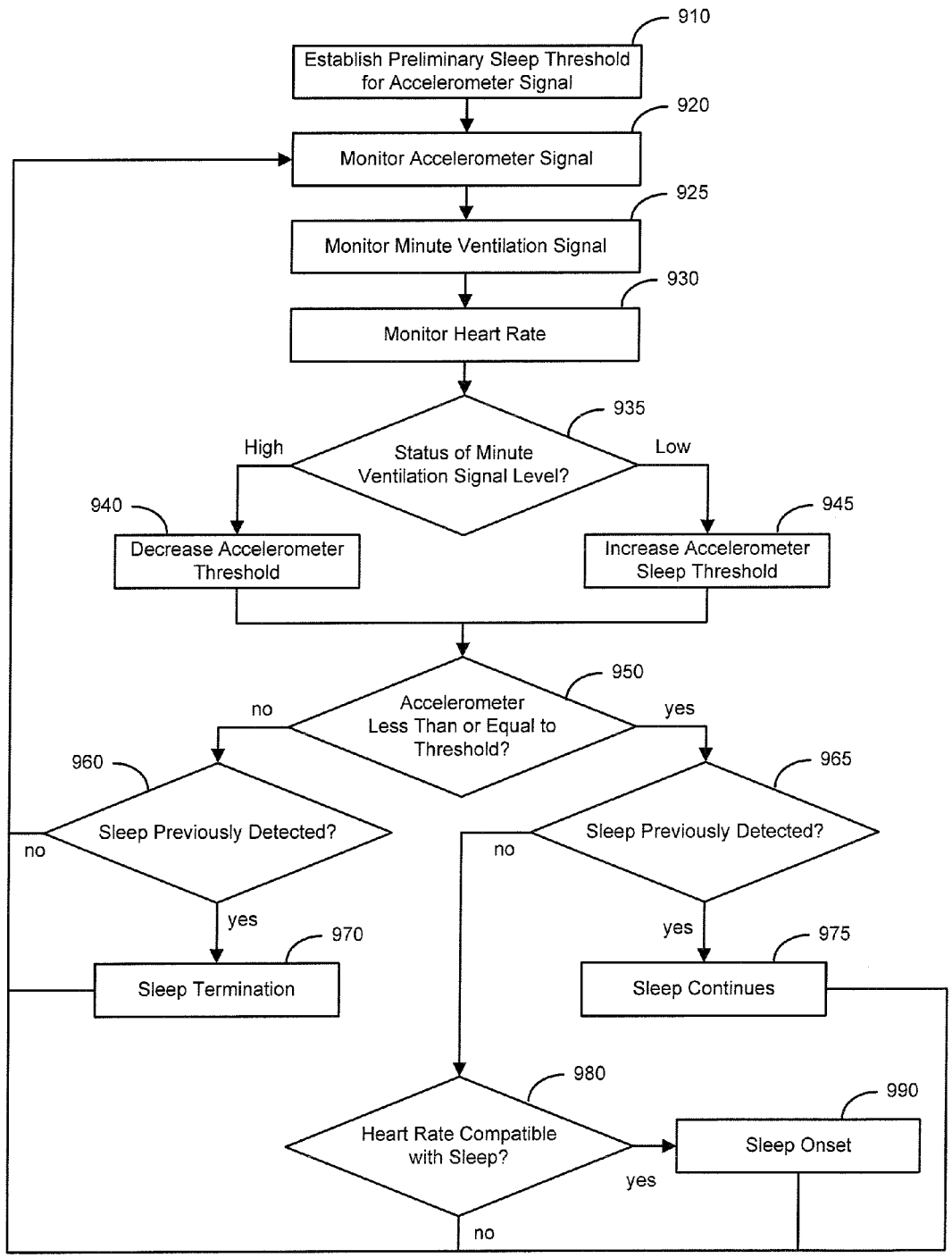
FIG. 9 is a flowchart illustrating a sleep detection method based on signals from an accelerometer and a minute ventilation sensor in accordance with embodiments of the invention.

In another embodiment of the invention, illustrated in the flowchart of FIG. 9, an accelerometer and a minute ventilation sensor are used to develop the first and second signals associated with sleep. A preliminary accelerometer signal sleep threshold is determined 910. For example, the preliminary sleep threshold may be determined from clinical data taken from a group of subjects or historical data taken from the patient over a period of time.

The activity level of the patient is monitored using an accelerometer 920 that may be incorporated into an implantable cardiac pacemaker as described above. Alternatively, the accelerometer may be attached externally to the patient. The patient's minute ventilation (MV) signal is monitored 925. The MV signal may be acquired, for example, based on the transthoracic impedance signal as described above using an implantable cardiac device. Other methods of determining the MV signal are also possible and are considered to be within the scope of this invention.

In this example, the accelerometer signal represents the sleep detection signal that is compared to the sleep threshold. The MV signal is the threshold adjustment signal used to adjust the sleep threshold. Heart rate is monitored 930 in this example to provide a sleep confirmation signal.

Threshold adjustment may be accomplished by using the patient's MV signal to moderate the accelerometer sleep threshold. If the patient's MV signal is low relative to an expected MV level associated with sleep, the accelerometer sleep threshold is increased. Similarly, if the patient's MV signal level is high relative to an expected MV level associated with sleep, the accelerometer sleep threshold is decreased. Thus, when the patient's MV level is high, less activity is required to make the determination that the patient is sleeping. Conversely when the patient's MV level is relatively low, a higher activity level may result in detection of sleep. The use of two sleep-related signals to determine a sleep condition enhances the accuracy of sleep detection over previous methods using only one sleep-related signal to determine that a patient is sleeping.

Various signal processing techniques may be employed to process the raw sensor signals. For example, a moving average of a plurality of samples of each sleep-related signal may be calculated and used as the sleep-related signal. Furthermore, the sleep-related signals may be filtered and/or digitized. If the MV signal is high 935 relative to an expected MV level associated with sleep, the accelerometer sleep threshold is decreased 940. If the MV signal is low 935 relative to an expected MV level associated with sleep, the accelerometer sleep threshold is increased 945.

If the sensed accelerometer signal is less than or equal to the adjusted sleep threshold 950, and if the patient is not currently in a sleep state 965, then the patient's heart rate is checked 980 to confirm the sleep condition. If the patient's heart rate is compatible with sleep 980, then sleep onset is determined 990. If the patient's heart rate is incompatible with sleep, then the patient's sleep-related signals continue to be monitored.

If the accelerometer signal is less than or equal to the adjusted sleep threshold 950 and if the patient is currently in a sleep state 965, then a continuing sleep state is determined 975 and the patient's sleep-related signals continue to be monitored for sleep termination to occur.

If the accelerometer signal is greater than the adjusted sleep threshold 950 and the patient is not currently in a sleep state 960, then the patient's sleep-related signals continue to be monitored until sleep onset is detected 990. If the accelerometer signal is greater than the adjusted sleep threshold 950 and the patient is currently in a sleep state 960, then sleep termination is detected 970.

Figure 10A:
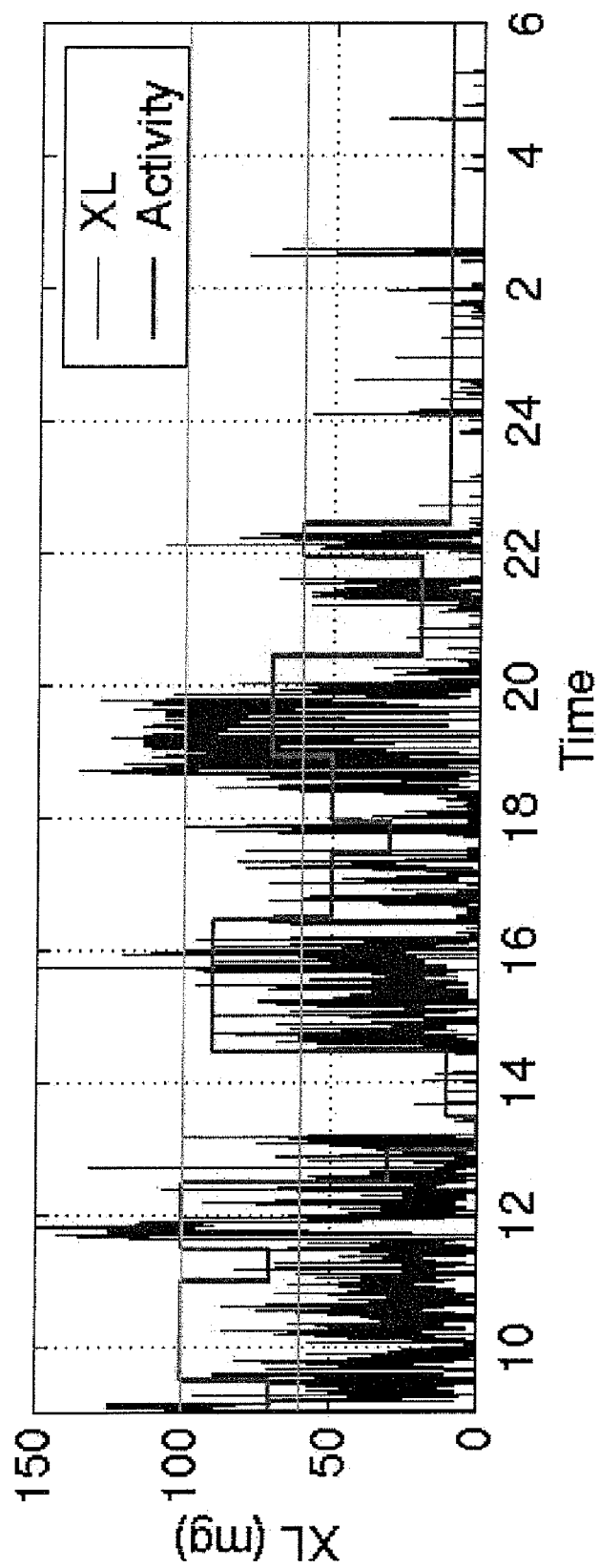
FIG. 10A is a graph of an accelerometer signal indicating patient activity level that may be used for sleep detection in accordance with embodiments of the invention.
Figure 10B:
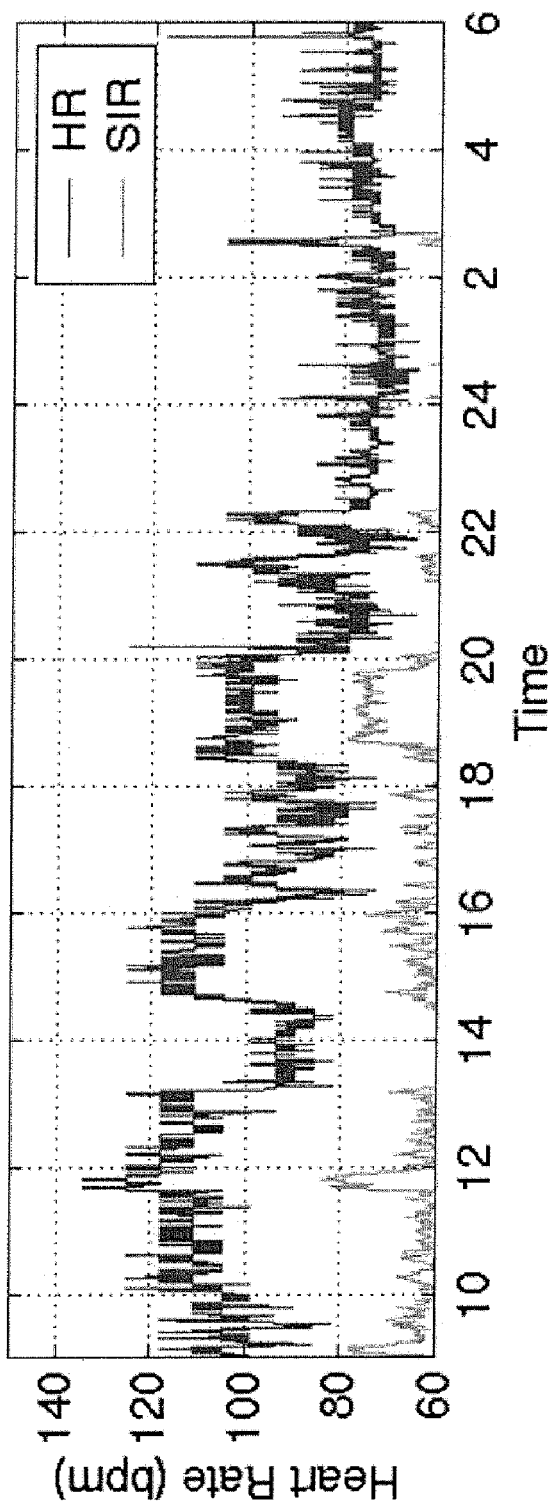
FIG. 10B is a graph of a patient's heart rate and sensor indicated rate that may be used for sleep detection in accordance with an embodiment of the invention.
Figure 11:
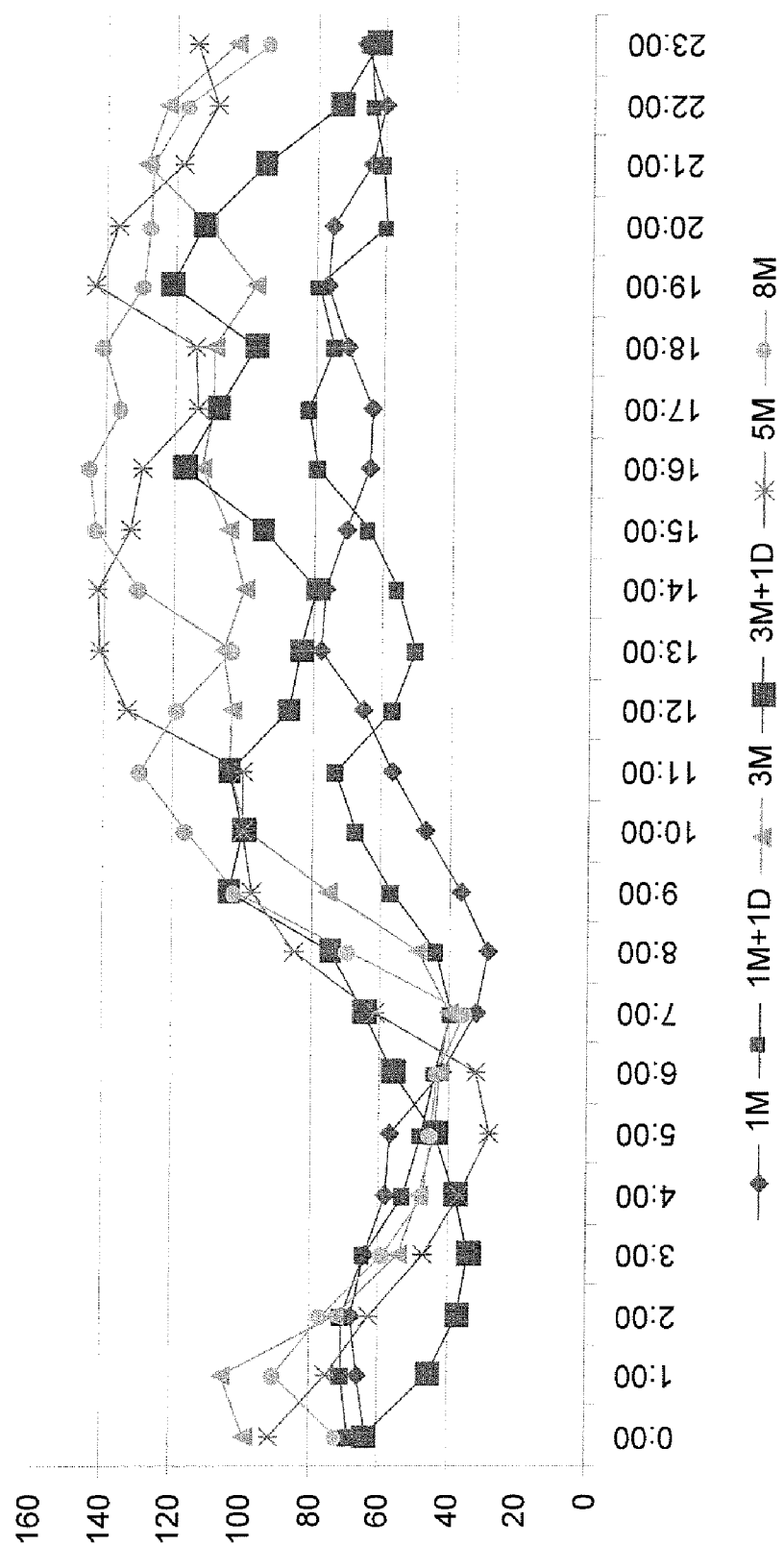
FIG. 11 is a graph of baseline trending for a minute ventilation signal used for sleep detection in accordance with embodiments of the invention.
Figure 12:
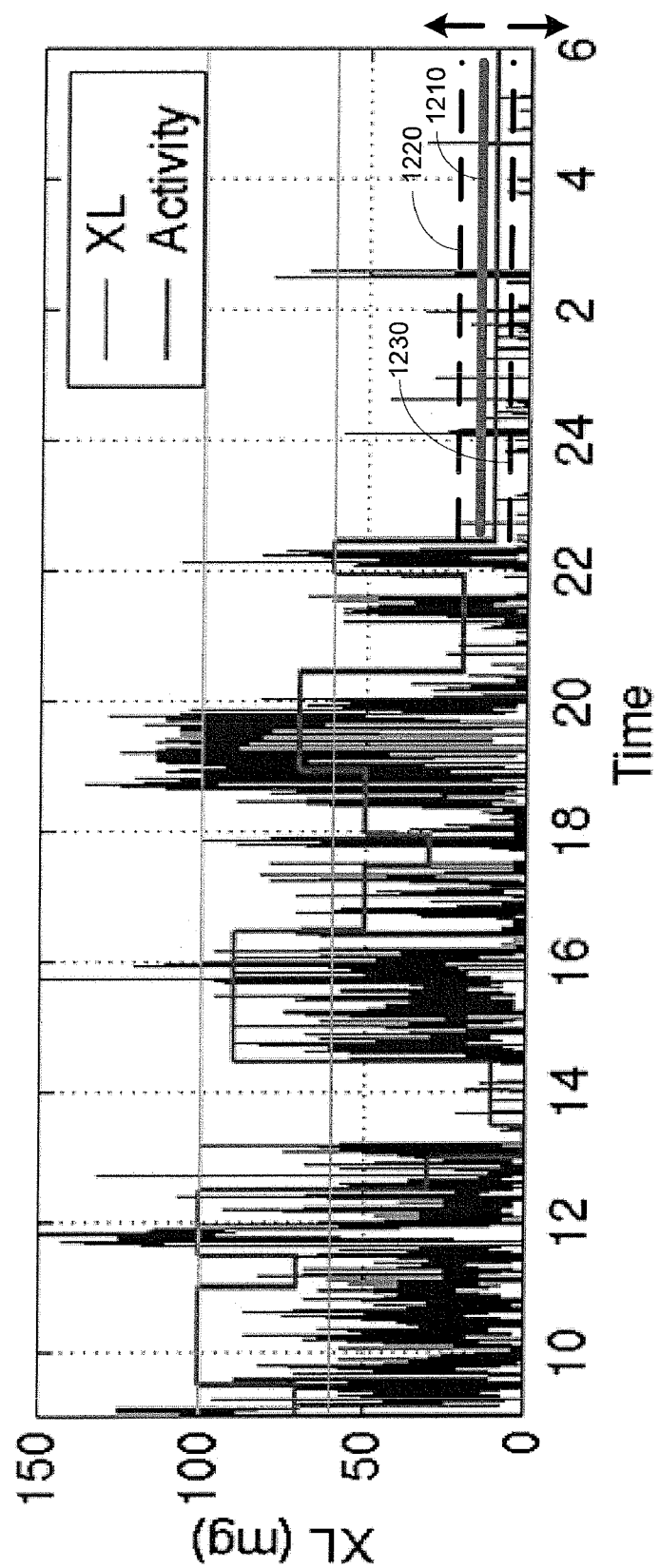
FIG. 12 illustrates adjustment of an accelerometer sleep threshold using an MV signal in accordance with embodiments of the invention

The graphs of FIGS. 10-12 illustrate the adjustment of the accelerometer sleep threshold using the MV signal. The relationship between patient activity and the accelerometer and MV signals is trended over a period of time to determine relative signal levels associated with a sleep condition. FIG. 10A illustrates activity as indicated by the accelerometer signal. The patient's heart rate for the same period is graphed in FIG. 10B. The accelerometer signal indicates a period of sleep associated with a relatively low level of activity beginning at slightly before 23:00 and continuing through 6:00. Heart rate appropriately tracks the activity level indicated by the accelerometer indicating a similar period of low heart rate corresponding to sleep. The accelerometer trends are used to establish a threshold for sleep detection.

FIG. 11 is a graph of baseline trending for an MV signal. Historical data of minute ventilation of a patient is graphed over an 8 month period. The MV signal trending data is used to determine the MV signal level associated with sleep. In this example, a composite MV signal using the historical data indicates a roughly sinusoidal shape with the relatively low MV levels occurring approximately during the period from hours 21:00 through 8:00. The low MV levels are associated with periods of sleep. The MV signal level associated with sleep is used to implement sleep threshold adjustment.

FIG. 12 illustrates adjustment of the accelerometer sleep threshold using the MV signal. The initial sleep threshold 1210 is established using the baseline accelerometer signal data acquired as discussed above. If the patient's MV signal is low relative to an expected MV level associated with sleep, the accelerometer sleep threshold is increased 1220. If the patient's MV signal level is high relative to an expected MV level associated with sleep, the accelerometer sleep threshold is decreased 1230. When the patient's MV level is high, less activity detected by the accelerometer is required to make the determination that the patient is sleeping. However, if the patient's MV level is relatively low a higher activity level may result in detection of sleep. The use of two sleep-related signals to adjust a sleep threshold for determining a sleep condition enhances the accuracy of sleep detection over previous methods.

Additional sleep-related signals may be sensed and used to improve the sleep detection mechanism described above. For example, a posture sensor may be used to detect the posture of the patient and used to confirm sleep. If the posture sensor indicates a vertical posture, then the posture sensor signal may be used to override a determination of sleep using the sleep detection and threshold adjustment signals. Other signals may also be used in connection with sleep determination or confirmation, including the representative set of sleep-related signals associated with sleep indicated above. Methods and systems related to sleep detection, aspects of which may be utilized in connection with the methodologies of the present invention, are described in commonly owned U.S. Pat. No. 7,189,204 and incorporated herein by reference.

The above described sleep-detection methods may be used for discriminating between periods of sleep and periods of wakefulness. Knowledge of sleep onset, offset, arousal episodes, and/or length of uninterrupted sleep may provide useful information for coordinating sleep disordered breathing therapy and/or be used to monitor patient conditions.

Sleep stage discrimination, including REM and non-REM sleep stages may additionally be used in connection with disordered breathing therapy. For example, some patients may experience sleep disordered breathing primarily during particular sleep stages. The implantable device may monitor sleep stages and disordered breathing episodes. The disordered breathing information may be analyzed in view of the sleep stage information. The analysis may be helpful in adapting a breathing therapy for a patient, e.g. delivering breathing therapy during sleep stages that predispose the patient to disordered breathing episodes. In one implementation, sleep information associated with sleep stages and/or arousals from sleep may be determined using information from an EEG sensor.

In another implementation, sleep stage information may be obtained using one or more muscle atonia sensors. Methods and systems for implementing of sleep stage detection using muscle atonia sensors are described in commonly owned U.S. Publication No. 2005/0043652, which is incorporated herein by reference.

Various aspects of sleep quality, including number and severity of arousals, sleep disordered breathing episodes, limb movements during sleep, and cardiac, respiratory, muscle, and nervous system functioning during sleep may provide important information relevant to the delivery of coordinated breathing therapy. Methods and systems for collecting and assessing sleep quality data are described in commonly owned U.S. Publication No. 2005/0042589, which is incorporated herein by reference.

Determining the effectiveness and/or impact of coordinated sleep disordered breathing therapy may involve detecting the sleep disordered breathing episodes. Sleep disordered breathing is a serious respiratory condition involving disruption of the normal respiratory cycle. The respiratory disruptions caused by disordered breathing can be particularly serious for patients concurrently suffering from cardiovascular deficiencies, such as congestive heart failure. Unfortunately, disordered breathing is often undiagnosed. If left untreated, the effects of disordered breathing may result in serious health consequences for the patient.

Episodes of disordered breathing are associated with acute and chronic physiological effects. Acute responses to disordered breathing may include, for example, negative intrathoracic pressure, hypoxia, arousal from sleep, and increases in blood pressure and heart rate. During obstructive apnea episodes, negative intrathoracic pressure may arise from an increased effort to generate airflow. Attempted inspiration in the presence of an occluded airway results in an abrupt reduction in intrathoracic pressure. The repeated futile inspiratory efforts associated with obstructive sleep apnea may trigger a series of secondary responses, including mechanical, hemodynamic, chemical, neural, and inflammatory responses.

Obstructive sleep apneas may be terminated by arousal from sleep several seconds after the apneic peak, allowing the resumption of airflow. Coincident with arousal from sleep, surges in sympathetic nerve activity, blood pressure, and heart rate may occur. The adverse effects of obstructive apnea are not confined to sleep. Daytime sympathetic nerve activity and systemic blood pressure are increased. There may also be a sustained reduction in vagal tone, causing reduction in total heart rate variability during periods of wakefulness.

Central sleep apnea is generally caused by a failure of respiratory control signals from the brain. Central sleep apnea is a component of Cheyne-Stokes respiration (CSR), a respiration pattern primarily observed in patients suffering from chronic heart failure (CHF). Cheyne-Stokes respiration is a form of periodic breathing in which central apneas and hypopneas alternate with periods of hyperventilation causing a waxing-waning pattern of tidal volume. In some CHF patients, obstructive sleep apnea and central sleep apnea may coexist. In these patients, there may be a gradual shift from predominantly obstructive apneas at the beginning of the night to predominantly central apneas at the end of the night.

Disordered breathing may be detected by sensing and analyzing various conditions associated with disordered breathing. Table 2 provides examples of how a representative subset of the physiological and contextual conditions listed in Table 1 may be used in connection with disordered breathing detection.

Detection of disordered breathing may involve comparing one condition or multiple conditions to one or more thresholds or other indices indicative of disordered breathing. A threshold or other index indicative of disordered breathing may comprise a predetermined level of a particular condition, e.g., blood oxygen level less than a predetermined amount. A threshold or other index indicative of disordered breathing may comprises a change in a level of a particular condition, e.g., heart rate decreasing from a sleep rate to lower rate within a predetermined time interval.

In one approach, the relationships between the conditions may be indicative of disordered breathing. In this embodiment, disordered breathing detection may be based on the existence and relative values associated with two or more conditions. For example, if condition A is present at a level of x, then condition B must also be present at a level of f(x) before a disordered breathing detection is made.

The thresholds and/or relationships indicative of disordered breathing may be highly patient specific. The thresholds and/or relationships indicative of disordered breathing may be determined on a case-by-case basis by monitoring conditions affecting the patient and monitoring disordered breathing episodes. The analysis may involve determining levels of the monitored conditions and/or relationships between the monitored conditions associated, e.g., statistically correlated, with disordered breathing episodes. The thresholds and/or relationships used in disordered breathing detection may be updated periodically to track changes in the patient's response to disordered breathing.

TABLE 2

| Condition Type | Condition | Examples of how condition may be used in disordered breathing detection |
| --- | --- | --- |
| Physiological | Heart rate | Decrease in heart rate may indicate disordered breathing episode. Increase in heart rate may indicate autonomic arousal from a disordered breathing episode. Decrease in heart rate may indicate the patient is asleep. |

TABLE 2-continued

| Condition Type | Condition | Examples of how condition may be used in disordered breathing detection |
|---|---|---|
| | Heart rate variability | Disordered breathing causes heart rate variability to decrease. Changes in HRV associated with sleep disordered breathing may be observed while the patient is awake or asleep |
| | Ventricular filling pressure | May be used to identify/predict pulmonary congestion associated with respiratory disturbance. |
| | Blood pressure | Swings in on-line blood pressure measures are associated with apnea. Disordered breathing generally increases blood pressure variability - these changes may be observed while the patient is awake or asleep. |
| | Snoring | Snoring is associated with a higher incidence of obstructive sleep apnea and may be used to detect disordered breathing. |
| | Respiration pattern/rate | Respiration patterns including, e.g., respiration rate, may be used to detect disordered breathing episodes. Respiration patterns may be used to determine the type of disordered breathing. Respiration patterns may be used to detect that the patient is asleep. |
| | Patency of upper airway | Patency of upper airway is related to obstructive sleep apnea and may be used to detect episodes of obstructive sleep apnea. |
| | Pulmonary congestion | Pulmonary congestion is associated with respiratory disturbances. |
| | Sympathetic nerve activity | End of apnea associated with a spike in SNA. Changes in SNA observed while the patient is awake or asleep may be associated with sleep disordered breathing |
| | CO2 | Low CO2 levels initiate central apnea. |
| | O2 | O2 desaturation occurs during severe apnea/hypopnea episodes. |
| | Blood alcohol content | Alcohol tends to increase incidence of snoring & obstructive apnea. |
| | Adrenalin | End of apnea associated with a spike in blood adrenaline. |
| | BNP | A marker of heart failure status, which is associated with Cheyne-Stokes Respiration |
| | C-Reactive Protein | A measure of inflammation that may be related to apnea. |
| | Drug/ Medication/ Tobacco use | These substances may affect the incidence of both central & obstructive apnea. |
| | Muscle atonia | Muscle atonia may be used to detect REM and non-REM sleep. |
| | Eye movement | Eye movement may be used to detect REM and non-REM sleep. |
| Contextual | Temperature | Ambient temperature may be a condition predisposing the patient to episodes of disordered breathing and may be useful in disordered breathing detection. |
| | Humidity | Humidity may be a condition predisposing the patient to episodes of disordered breathing and may be useful in disordered breathing detection. |
| | Pollution | Pollution may be a condition predisposing the patient to episodes of disordered breathing and may be useful in disordered breathing detection. |
| | Posture | Posture may be used to confirm or determine the patient is asleep. |
| | Activity | Patient activity may be used in relation to sleep detection. |
| | Location | Patient location may used to determine if the patient is in bed as a part of sleep detection. |
| | Altitude | Lower oxygen concentrations at higher altitudes tends to cause more central apnea |

In various implementations, episodes of disordered breathing may be detected and classified by analyzing the patient's respiration patterns. Methods and systems of disordered breathing detection based on respiration patterns are further described in commonly owned U.S. Pat. No. 7,252,640, which is incorporated herein by reference.

Once disordered breathing is identified based on the sensed conditions indicative of disordered breathing, delivery of therapy can be coordinated based on the detected disordered breathing.

Similar to detecting disordered breathing, predicting disordered breathing based on sensed conditions is patient specific. Each of the conditions listed in Table 1 may serve a variety of purposes in predicting disordered breathing. Various subsets of the conditions listed in Table 1 may be detected as predisposing conditions, precursor conditions, and/or verification conditions useful in the prediction of disordered breathing. In one example, information regarding sleep onset may be employed in prediction of sleep disordered breathing. A subset of the conditions listed in Table 1 may be used to detect whether the patient is asleep and to track the various stages of sleep. Another subset of the conditions may be employed to detect and classify disordered breathing episodes. Table 3 below provides further examples of how the physiological and contextual conditions of the patient may be used in disordered breathing prediction.

TABLE 3

| Condition | Examples of how condition is used in disordered breathing prediction |
|---|---|
| Heart rate | Decrease in heart rate may indicate disordered breathing episode. Decrease in heart rate may indicate the patient is asleep. Increase in heart rate may indicate autonomic arousal from disordered breathing. |
| Heart rate variability | May be used to determine sleep state |
| Ventricular filling pressure | May be used to identify/predict pulmonary congestion associated with respiratory disturbance. |
| Blood pressure | Swings in on-line blood pressure measures are associated with apnea. |
| Snoring | Snoring is associated with a higher incidence of obstructive sleep apnea and may be used to detect disordered breathing. |
| Respiration signals/respiration patterns | Respiration patterns may be used to detect disordered breathing episodes. Respiration patterns may be used to determine the type of disordered breathing. Respiration patterns may be used to detect that the patient is asleep. Hyperventilation may be used to predict disordered breathing. Previous episodes of disordered breathing may be used to predict further episodes. One form of disordered breathing may be used to predict another form of disordered breathing |
| Patency of upper airway | Patency of upper airway is related to obstructive sleep apnea and may be used to detect episodes of obstructive sleep apnea. |
| Pulmonary congestion | Pulmonary congestion is associated with respiratory disturbances. |
| Sympathetic nerve activity | End of apnea associated with a spike in SNA |
| CO2 saturation | Low CO2 levels initiate central apnea. |
| O2 saturation | O2 desaturation occurs during severe apnea/hypopnea episodes. |
| Blood alcohol content | Alcohol tends to increase incidence of snoring & obstructive apnea. |
| Adrenalin | End of apnea associated with a spike in blood adrenaline. |
| BNP | A marker of heart failure status, which is associated with Cheyne-Stokes Respiration |
| C-Reactive Protein | A measure of inflammation that may be related to apnea. |
| Drug/Medication/ Tobacco use | These substances may affect incidence of both central & obstructive apnea. |
| Muscle atonia | Muscle atonia may be used to detect REM and non-REM sleep. |

TABLE 3-continued

| Condition | Examples of how condition is used in disordered breathing prediction |
|---|---|
| Eye movement | Eye movement may be used to detect REM and non-REM sleep. |
| Temperature | Ambient temperature may be a condition predisposing the patient to episodes of disordered breathing. |
| Humidity | Humidity may be a condition predisposing the patient to episodes of disordered breathing. |
| Pollution | Pollution may be a condition predisposing the patient to episodes of disordered breathing. |
| Posture | Posture may be used to determine if the patient is asleep. |
| | Posture may be a condition predisposing the patient to episodes of disordered breathing. |
| Activity | Patient activity may be used in relation to sleep detection. |
| Sleep stage | NREM sleep is associated with a higher incidence of DB episodes |
| Location | Patient location may used to determine if the patient is in bed as a part of sleep detection. |
| Altitude | Lower oxygen concentration associated with high altitudes predisposes patients to more central apnea |

In accordance with embodiments of the present invention, once disordered breathing is predicted, delivery of coordinated disordered breathing therapies can be performed. Methods and systems for predicting disordered breathing and for delivering therapy based on the prediction of disordered breathing are described in commonly owned U.S. Pat. Nos. 7,396,333 and 7,680,537, both of which are incorporated herein by reference.

FIG. 7 illustrates normal respiration as represented by a signal produced by a transthoracic impedance sensor. The transthoracic impedance increases during respiratory inspiration and decreases during respiratory expiration. During non-REM sleep, a normal respiration pattern includes regular, rhythmic inspiration-expiration cycles without substantial interruptions.

In one embodiment, episodes of disordered breathing may be detected by monitoring the respiratory waveform output of the transthoracic impedance sensor. When the tidal volume (TV) of the patient's respiration, as indicated by the transthoracic impedance signal, falls below a hypopnea threshold, then a hypopnea event is declared. For example, a hypopnea event may be declared if the patient's tidal volume falls below about 50% of a recent average tidal volume or other baseline tidal volume value. If the patient's tidal volume falls further to an apnea threshold, e.g., about 10% of the recent average tidal volume or other baseline value, an apnea event is declared.

Figure 13:
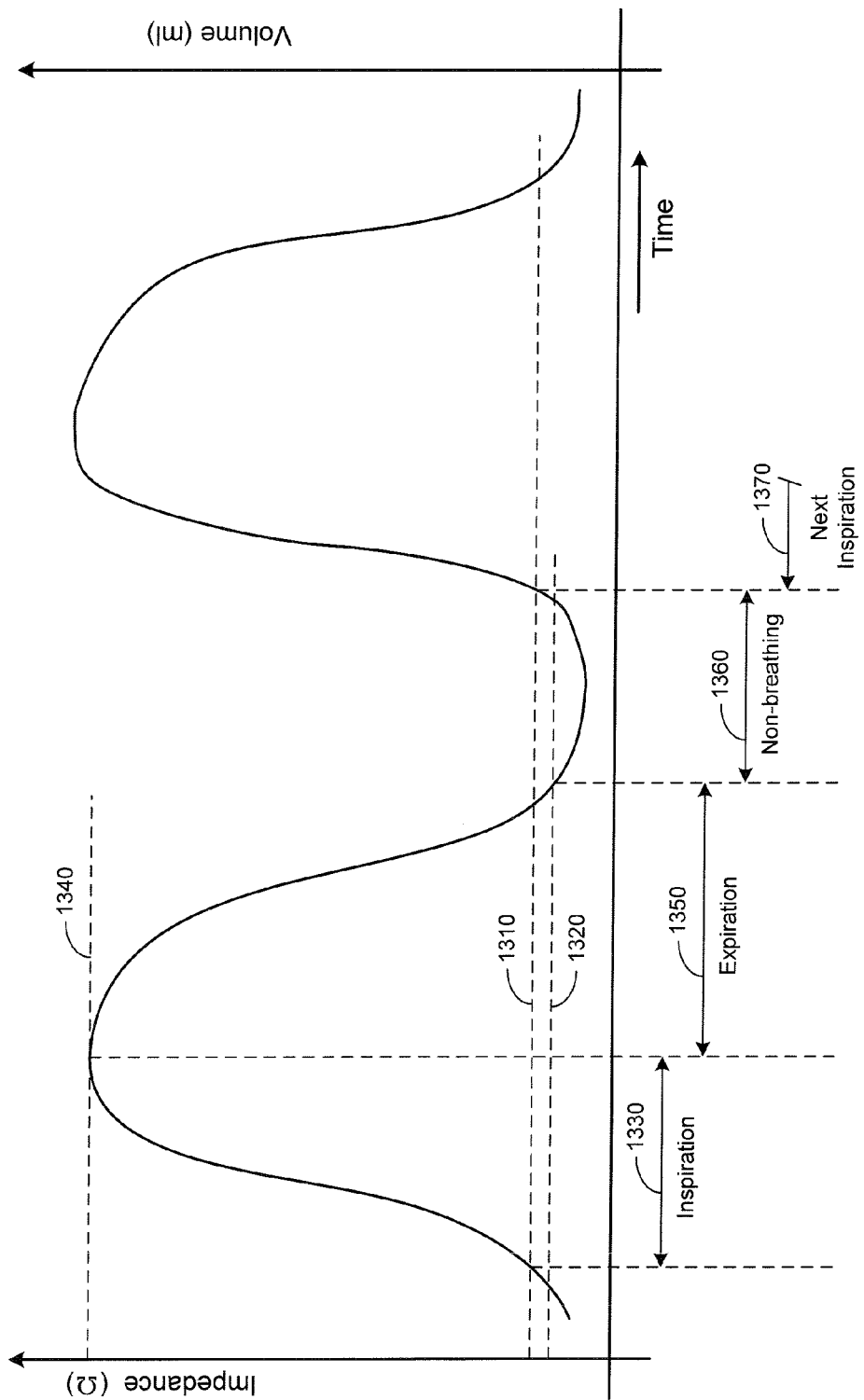
FIG. 13 is a respiration signal graph illustrating respiration intervals used for disordered breathing detection according to embodiments of the invention.

In another embodiment, detection of disordered breathing involves defining and examining a number of respiratory cycle intervals. FIG. 13 illustrates respiration intervals used for disordered breathing detection according to embodiments of the invention. A respiration cycle is divided into an inspiration period corresponding to the patient inhaling, an expiration period, corresponding to the patient exhaling, and a non-breathing period occurring between inhaling and exhaling. Respiration intervals are established using inspiration 1310 and expiration 1320 thresholds. The inspiration threshold 1310 marks the beginning of an inspiration period 1330 and is determined by the transthoracic impedance signal rising above the inspiration threshold 1310. The inspiration period 1330 ends when the transthoracic impedance signal is maximum 1340. A maximum transthoracic impedance signal 1340 corresponds to both the end of the inspiration interval 1330 and the beginning of the expiration interval 1350. The expiration interval 1350 continues until the transthoracic impedance falls below an expiration threshold 1320. A non-breathing interval 1360 starts from the end of the expiration period 1350 and continues until the beginning of the next inspiration period 1370.

Figure 14:
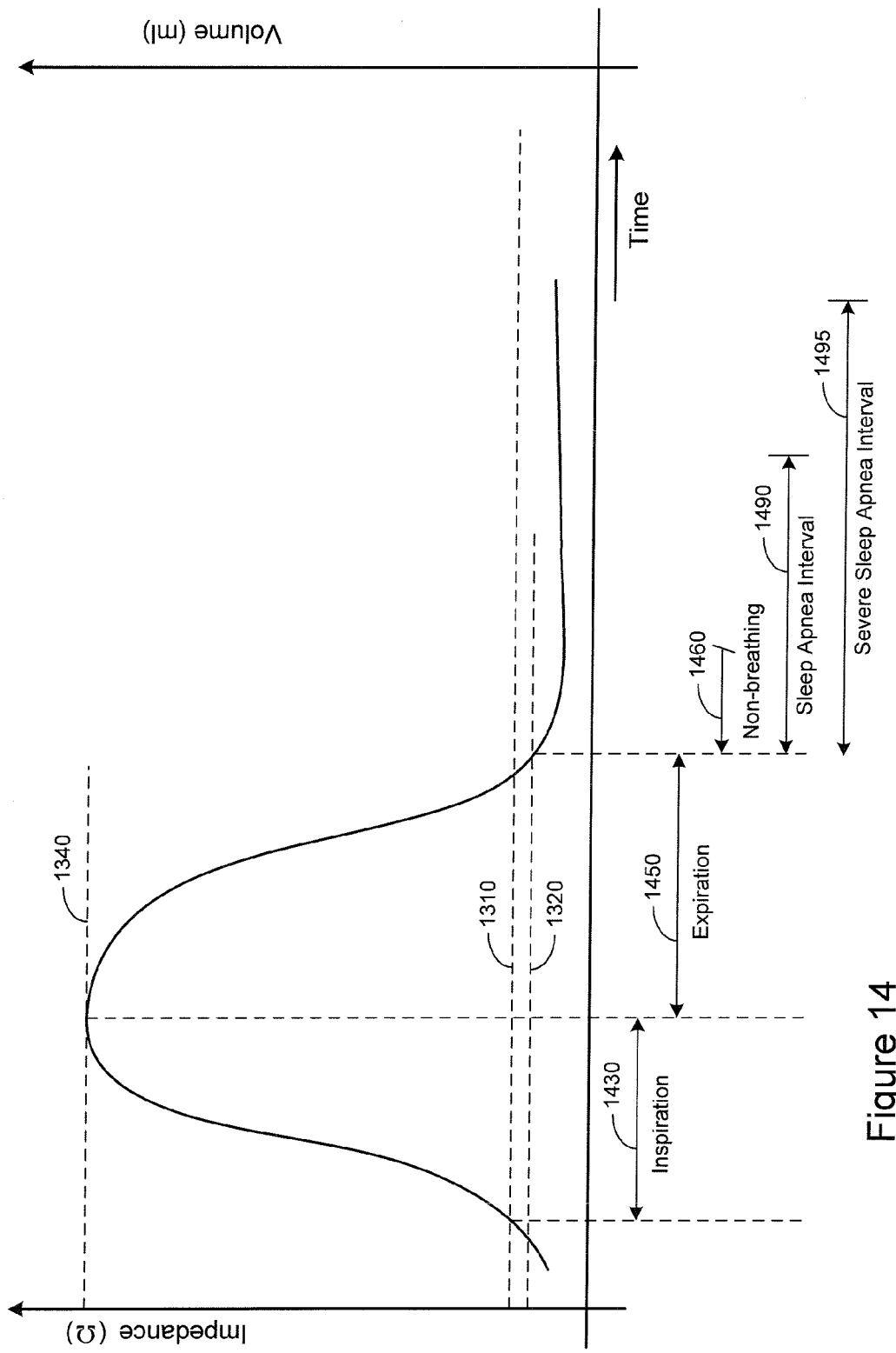
FIG. 14 is a graph of a respiration signal illustrating various intervals that may be used for detection of apnea in accordance with embodiments of the invention.

Detection of sleep apnea and severe sleep apnea according to embodiments of the invention is illustrated in FIG. 14. The patient's respiration signals are monitored and the respiration cycles are defined according to inspiration 1430, expiration 1450, and non-breathing 1460 intervals as described in connection with FIG. 13. A condition of sleep apnea is detected when a non-breathing period 1460 exceeds a first predetermined interval 1490, denoted the sleep apnea interval. A condition of severe sleep apnea is detected when the non-breathing period 1460 exceeds a second predetermined interval 1495, denoted the severe sleep apnea interval. For example, sleep apnea may be detected when the non-breathing interval exceeds about 10 seconds, and severe sleep apnea may be detected when the non-breathing interval exceeds about 20 seconds.

Figure 15A:
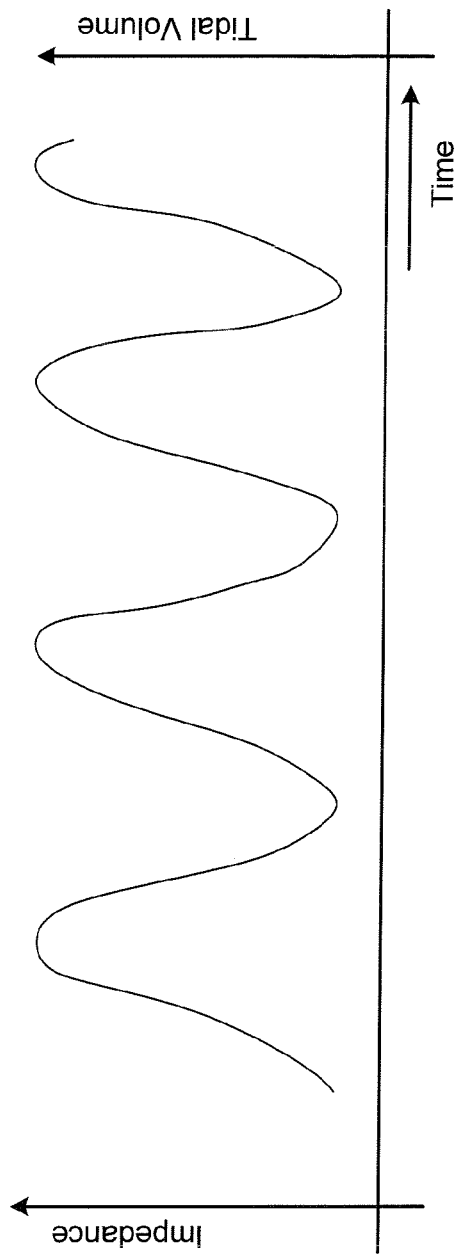
FIGS. 15A and 15B are respiration graphs illustrating normal respiration and abnormally shallow respiration utilized in detection of disordered breathing in accordance with embodiments of the invention.
Figure 15B:
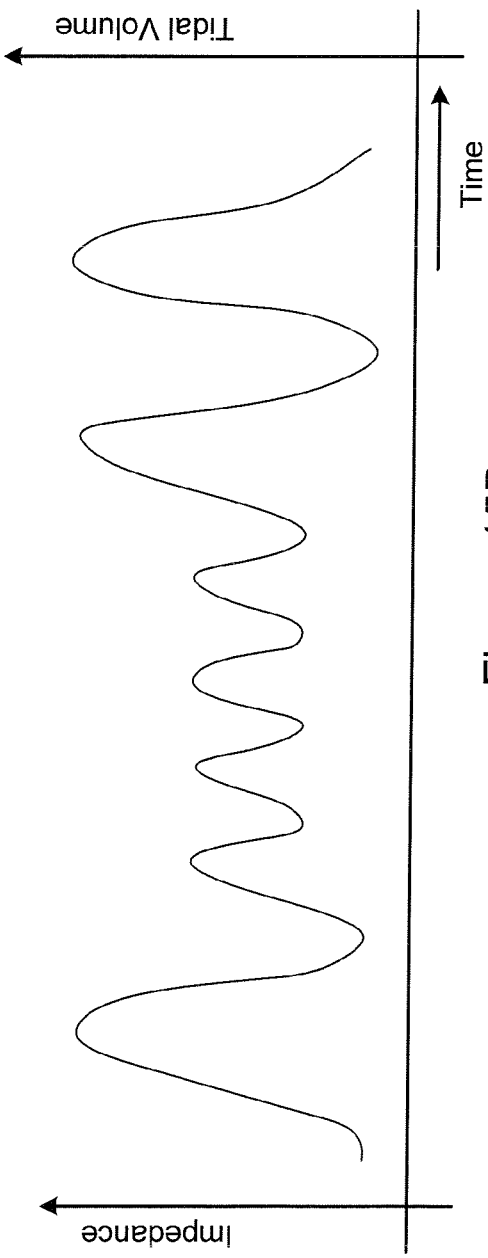

Hypopnea is a condition of disordered breathing characterized by abnormally shallow breathing. FIGS. 15A-15B are graphs of tidal volume derived from transthoracic impedance measurements. The graphs compare the tidal volume of a normal breathing cycle to the tidal volume of a hypopnea episode. FIG. 15A illustrates normal respiration tidal volume and rate. As shown in FIG. 15B, hypopnea involves a period of abnormally shallow respiration.

According to an embodiment of the invention, hypopnea is detected by comparing a patient's respiratory tidal volume to a hypopnea tidal volume threshold. The tidal volume for each respiration cycle is derived from transthoracic impedance measurements acquired in the manner described above. The hypopnea tidal volume threshold may be established using clinical results providing a representative tidal volume and duration of hypopnea events. In one configuration, hypopnea is detected when an average of the patient's respiratory tidal volume taken over a selected time interval falls below the hypopnea tidal volume threshold. Furthermore, various combinations of hypopnea cycles, breath intervals, and non-breathing intervals may be used to detect hypopnea, where the non-breathing intervals are determined as described above.

Figure 16:
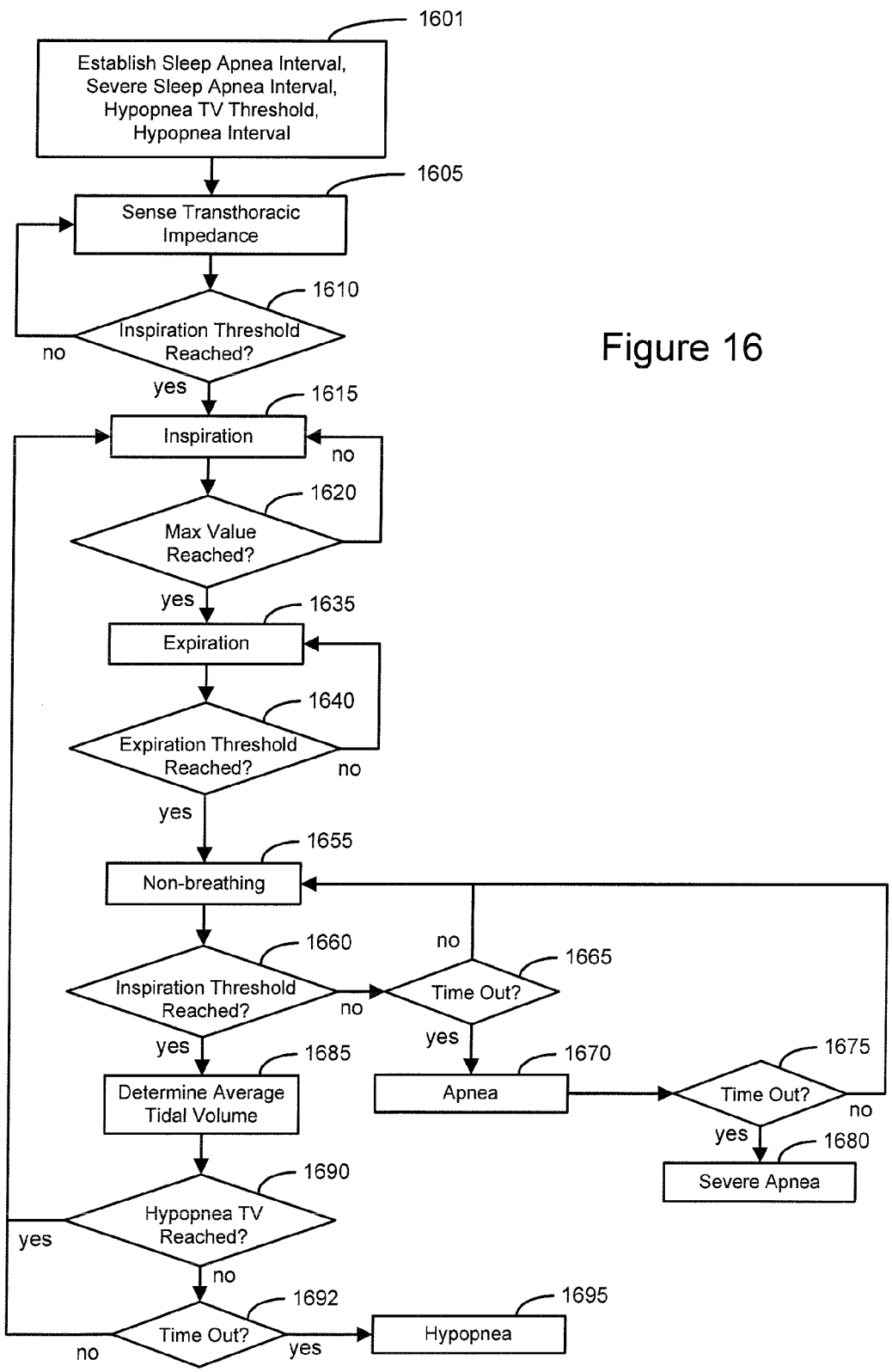
FIG. 16 is a flowchart illustrating a method of apnea and/or hypopnea detection according to embodiments of the invention.

FIG. 16 is a flowchart illustrating a method of apnea and/or hypopnea detection according to embodiments of the invention. Various parameters are established 1601 before analyzing the patient's respiration for disordered breathing episodes, including, for example, inspiration and expiration thresholds, sleep apnea interval, severe sleep apnea interval, and hypopnea tidal volume threshold.

The patient's transthoracic impedance is measured 1605 as described in more detail above. If the transthoracic impedance exceeds 1610 the inspiration threshold, the beginning of an inspiration interval is detected 1615. If the transthoracic impedance remains below 1610 the inspiration threshold, then the impedance signal is checked 1605 periodically until inspiration 1615 occurs.

During the inspiration interval, the patient's transthoracic impedance is monitored until a maximum value of the transthoracic impedance is detected 1620. Detection of the maximum value signals an end of the inspiration period and a beginning of an expiration period 1635.

The expiration interval is characterized by decreasing transthoracic impedance. When the transthoracic impedance falls 1640 below the expiration threshold, a non-breathing interval is detected 1655.

If the transthoracic impedance does not exceed 1660 the inspiration threshold within a first predetermined interval 1665, denoted the sleep apnea interval, then a condition of sleep apnea is detected 1670. Severe sleep apnea is detected 1680 if the non-breathing period extends beyond a second predetermined interval 1675, denoted the severe sleep apnea interval.

When the transthoracic impedance exceeds 1660 the inspiration threshold, the tidal volume from the peak-to-peak transthoracic impedance is calculated, along with a moving average of past tidal volumes 1685. The peak-to-peak transthoracic impedance provides a value proportional to the tidal volume of the respiration cycle. This value is compared to a hypopnea tidal volume threshold 1690. If the peak-to-peak transthoracic impedance is consistent with the hypopnea tidal volume threshold 1690 for a predetermined time 1692, then a hypopnea cycle is detected 1695.

Additional sensors, such as motion sensors, oximetry sensors, and/or posture sensors, may be used to confirm or verify the detection of a sleep apnea or hypopnea episode. The additional sensors may be employed to prevent false or missed detections of sleep apnea/hypopnea due to posture and/or motion related artifacts.

Another embodiment of the invention involves classifying respiration patterns as disordered breathing episodes based on the breath intervals and/or tidal volumes of one or more respiration cycles within the respiration patterns. According to this embodiment, the duration and tidal volumes associated with a respiration pattern are compared to duration and tidal volume thresholds. The respiration pattern is detected as a disordered breathing episode based on the comparison.

Figure 17:
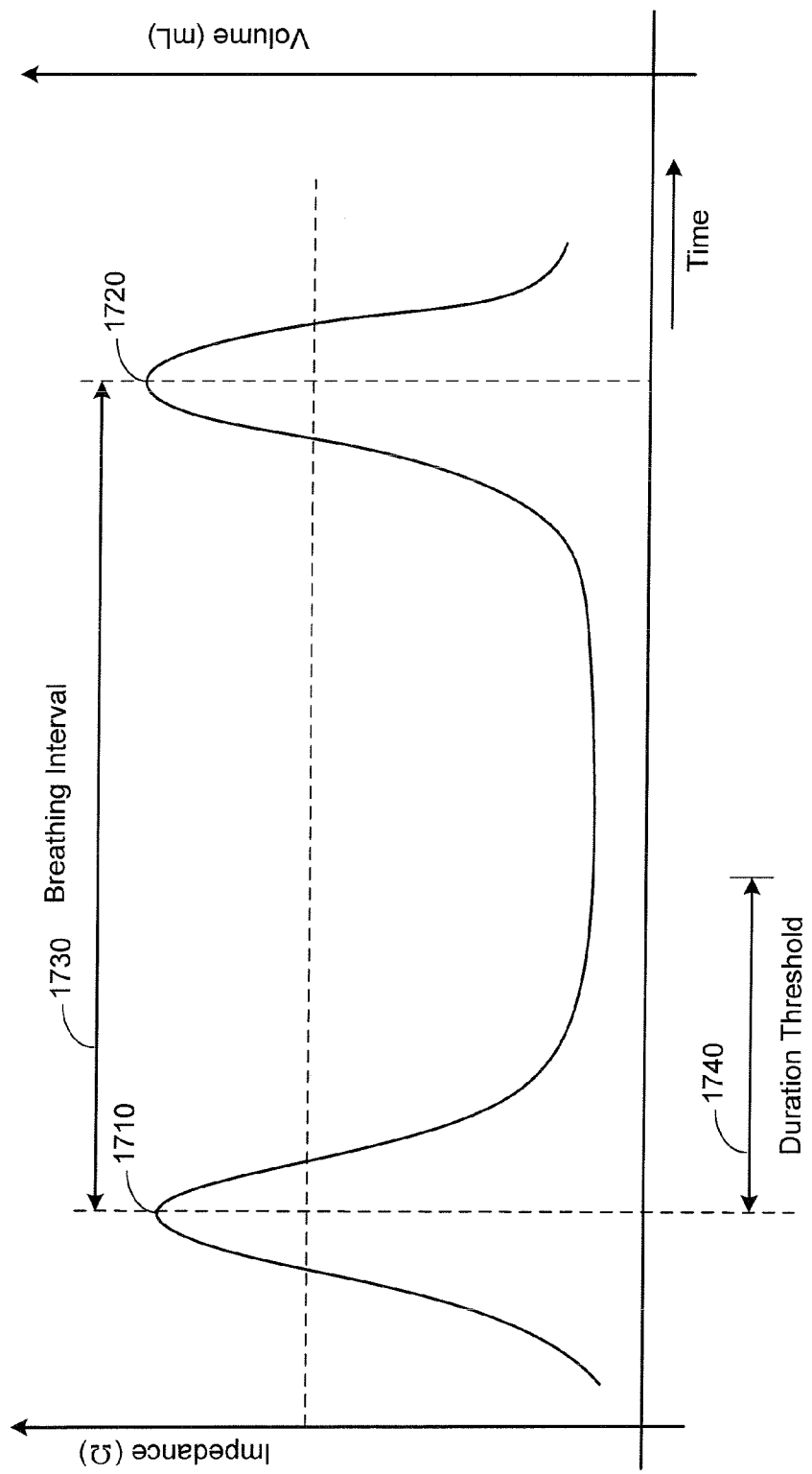
FIG. 17 is a respiration graph illustrating a breath interval utilized in connection with disordered breathing detection in accordance with embodiments of the invention.

According to principles of the invention, a breath interval is established for each respiration cycle. A breath interval represents the interval of time between successive breaths, as illustrated in FIG. 17. A breath interval 1730 may be defined in a variety of ways, for example, as the interval of time between successive maxima 1710, 1720 of the impedance signal waveform.

Detection of disordered breathing, in accordance with embodiments of the invention, involves the establishment of a duration threshold and a tidal volume threshold. If a breath interval exceeds the duration threshold, an apnea event is detected. Detection of sleep apnea, in accordance with this embodiment, is illustrated in the graph of FIG. 17. Apnea represents a period of non-breathing. A breath interval 1730 exceeding a duration threshold 1740 comprises an apnea episode.

Hypopnea may be detected using the duration threshold and tidal volume threshold. A hypopnea event represents a period of shallow breathing. Each respiration cycle in a hypopnea event is characterized by a tidal volume less than the tidal volume threshold. Further, the hypopnea event involves a period of shallow breathing greater than the duration threshold.

Figure 18:
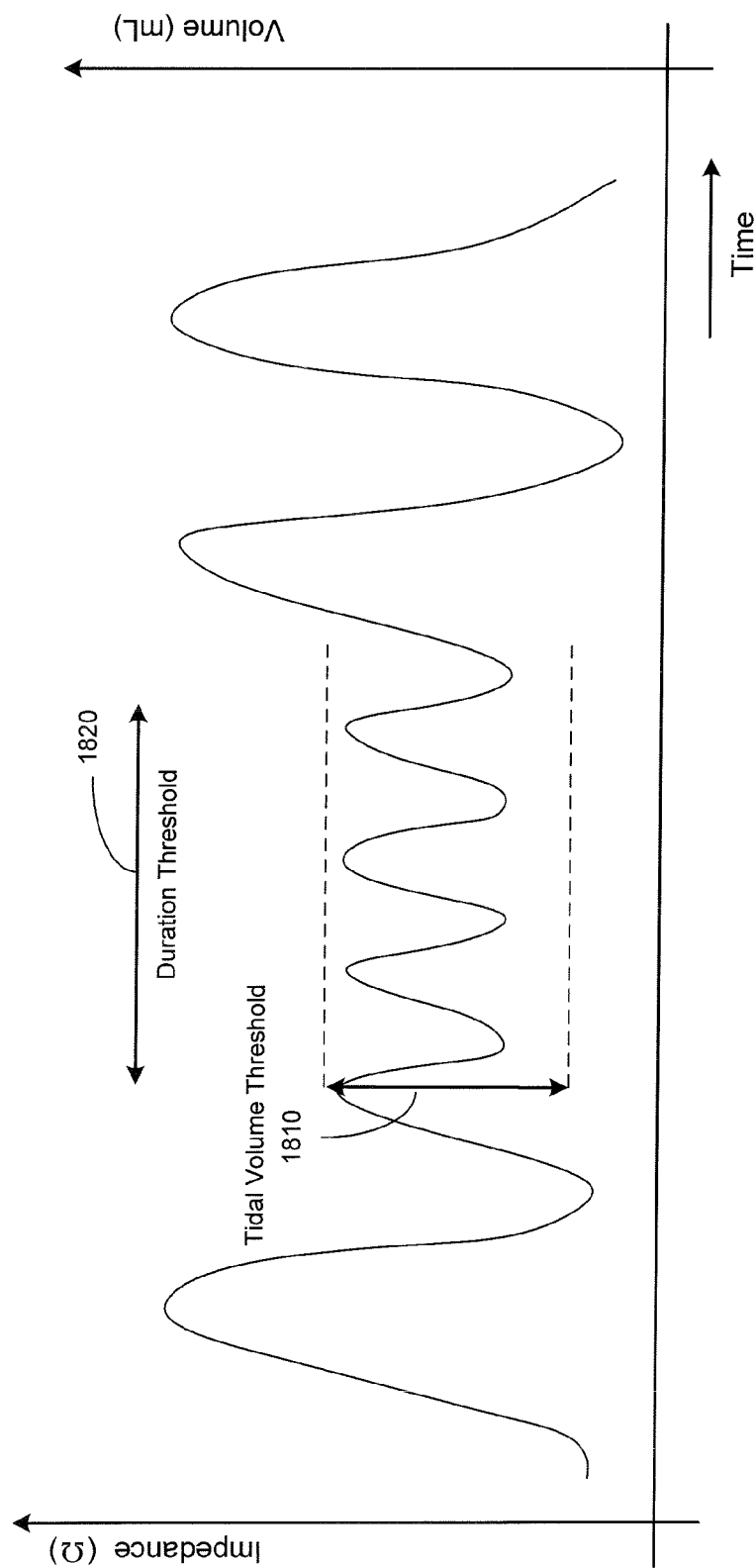
FIG. 18 is a respiration graph illustrating a hypopnea detection approach in accordance with embodiments of the invention.

A hypopnea detection approach, in accordance with embodiments of the invention, is illustrated in FIG. 18. Shallow breathing is detected when the tidal volume of one or more breaths is below a tidal volume threshold 1810. If the shallow breathing continues for an interval greater than a duration threshold 1820, then the breathing pattern represented by the sequence of shallow respiration cycles, is classified as a hypopnea event.

Figure 19:
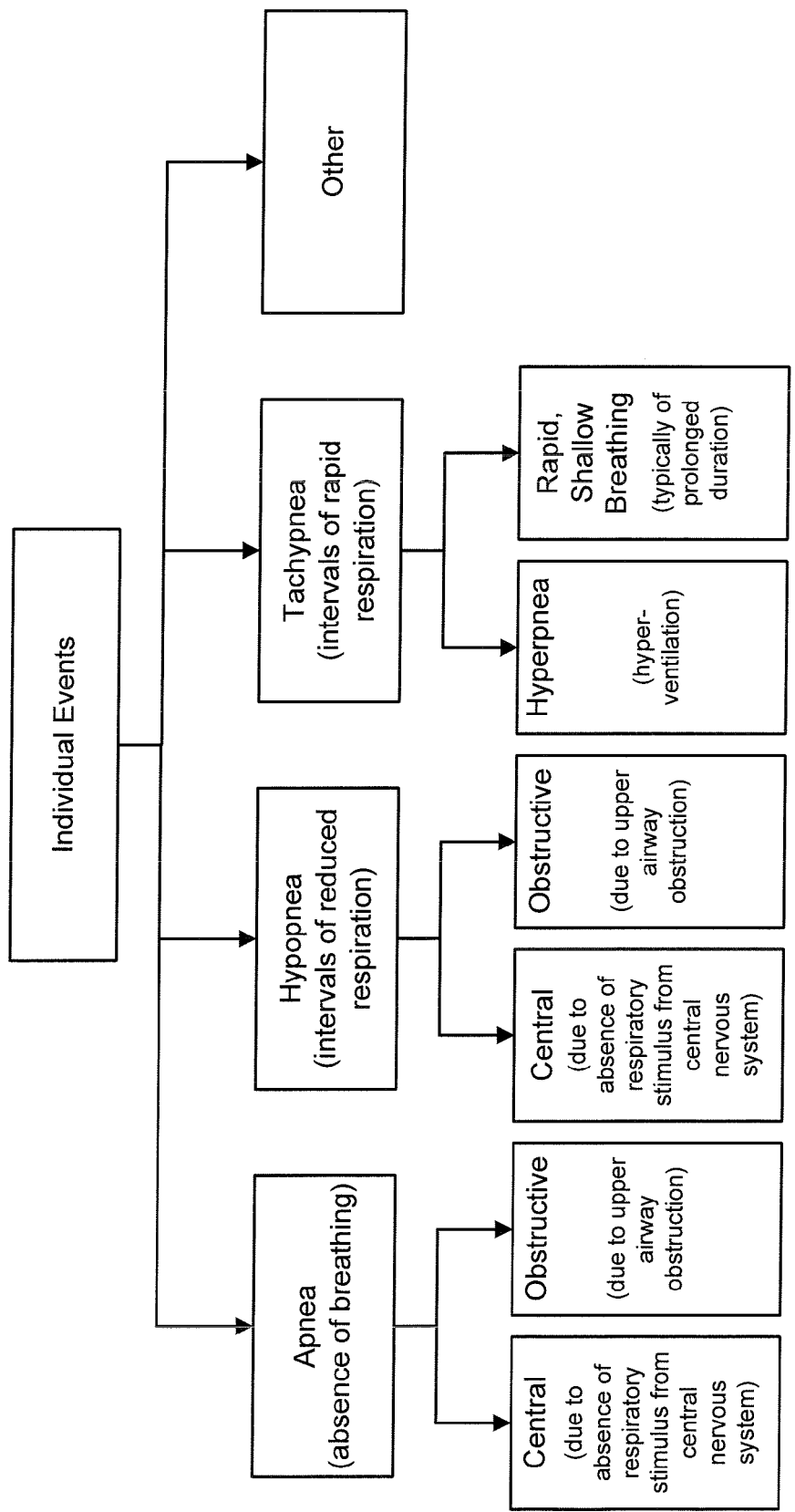
FIGS. 19 and 20 provide charts illustrating classification of individual disordered breathing events and series of periodically recurring disordered breathing events, respectively, in accordance with embodiments of the invention.
Figure 20:
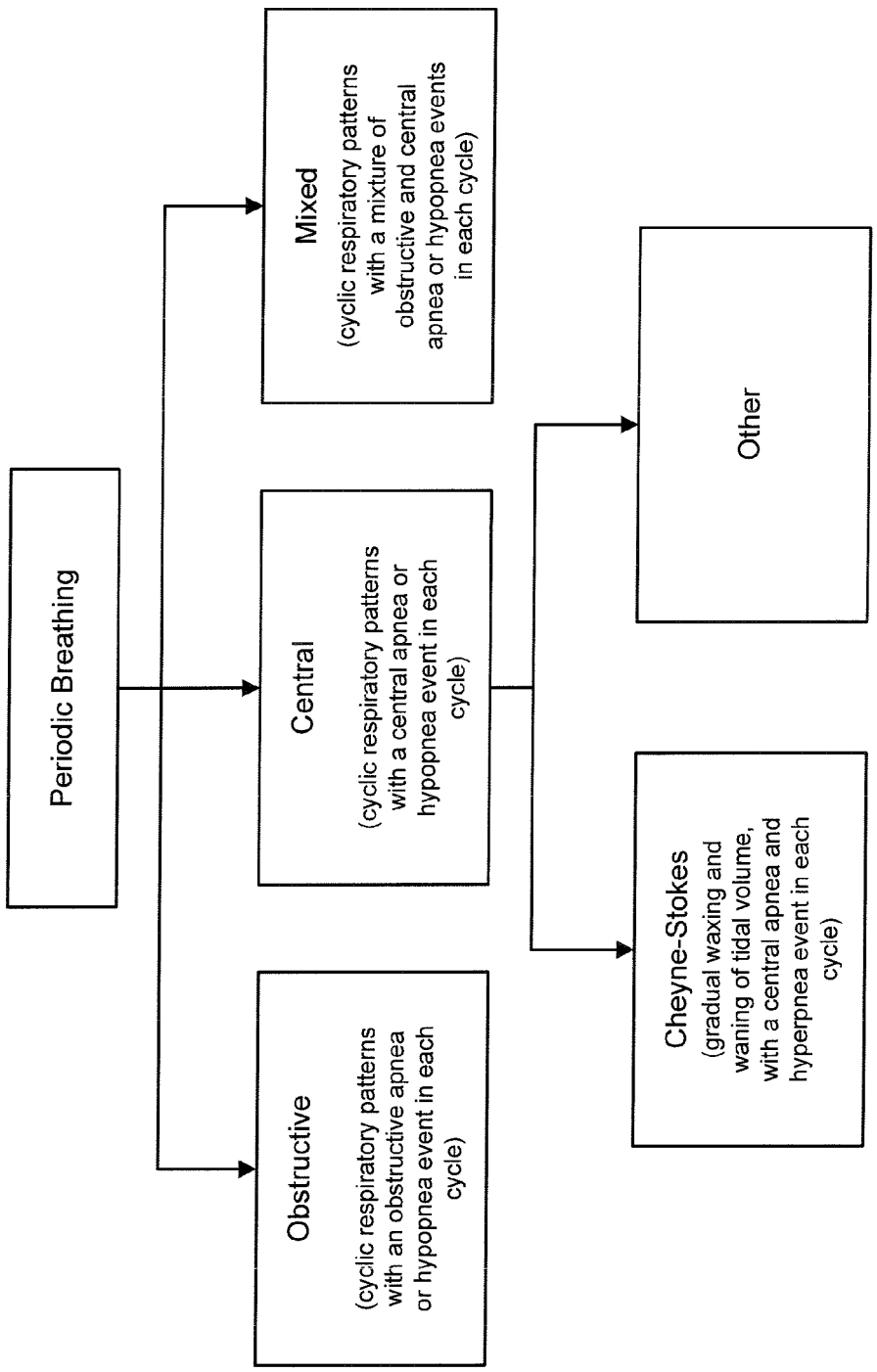

FIGS. 19 and 20 provide charts illustrating classification of individual disordered breathing events and series of periodically recurring disordered breathing events, respectively. As illustrated in FIG. 19, individual disordered breathing events may be grouped into apnea, hypopnea, tachypnea and other disordered breathing events. Apnea events are characterized by an absence of breathing. Intervals of reduced respiration are classified as hypopnea events. Tachypnea events include intervals of rapid respiration characterized by an elevated respiration rate.

As illustrated in FIG. 19, apnea and hypopnea events may be further subdivided as either central events, related to central nervous system dysfunction, or obstructive events, caused by upper airway obstruction. A tachypnea event may be further classified as a hyperpnea event, represented by hyperventilation, i.e., rapid deep breathing. A tachypnea event may alternatively be classified as rapid breathing, typically of prolonged duration.

FIG. 20 illustrates classification of combinations of periodically recurring disordered breathing events. Periodic breathing may be classified as obstructive, central or mixed. Obstructive periodic breathing is characterized by cyclic respiratory patterns with an obstructive apnea or hypopnea event in each cycle. Central periodic breathing involves cyclic respiratory patterns including a central apnea or hypopnea event in each cycle. Periodic breathing may also be of mixed origin. Mixed origin periodic breathing is characterized by cyclic respiratory patterns having a mixture of obstructive and central apnea events in each cycle. Cheyne-Stokes is a particular type of periodic breathing involving a gradual waxing and waning of tidal volume and having a central apnea and hyperpnea event in each cycle. Other manifestations of periodic breathing are also possible. Disordered breathing episodes may be classified based on the characteristic respiration patterns associated with particular types of disordered breathing.

Figure 21A:
FIGS. 21A-E are graphs illustrating respiration patterns that may be detected as disordered breathing episodes in accordance with embodiments of the invention.
Figure 21B:
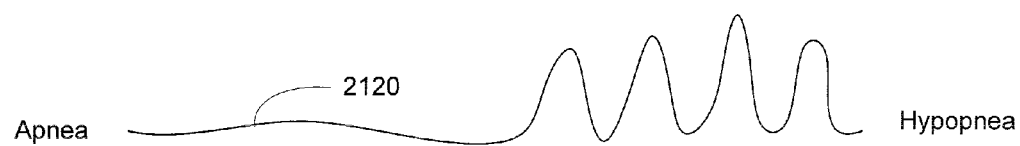
Figure 21C:
Figure 21D:
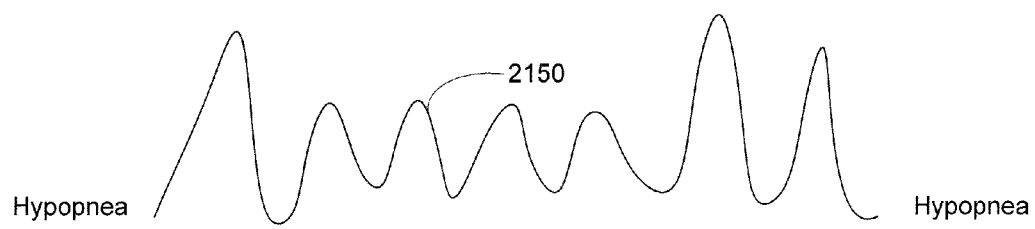
Figure 21E:
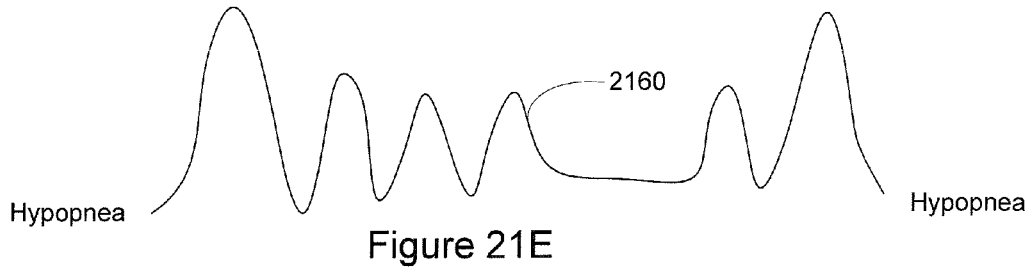

As illustrated in FIGS. 21A-E, a respiration pattern detected as a disordered breathing episode may include only an apnea respiration cycle 2110 (FIG. 21A), only hypopnea respiration cycles 2150 (FIG. 21D), or a mixture of hypopnea and apnea respiration cycles 2120 (FIG. 21B), 2130 (FIG. 21C), 2160 (FIG. 21E). A disordered breathing event 2120 may begin with an apnea respiration cycle and end with one or more hypopnea cycles. In another pattern, the disordered breathing event 2130 may begin with hypopnea cycles and end with an apnea cycle. In yet another pattern, a disordered breathing event 2160 may begin and end with hypopnea cycles with an apnea cycle in between the hypopnea cycles.

Figure 22:
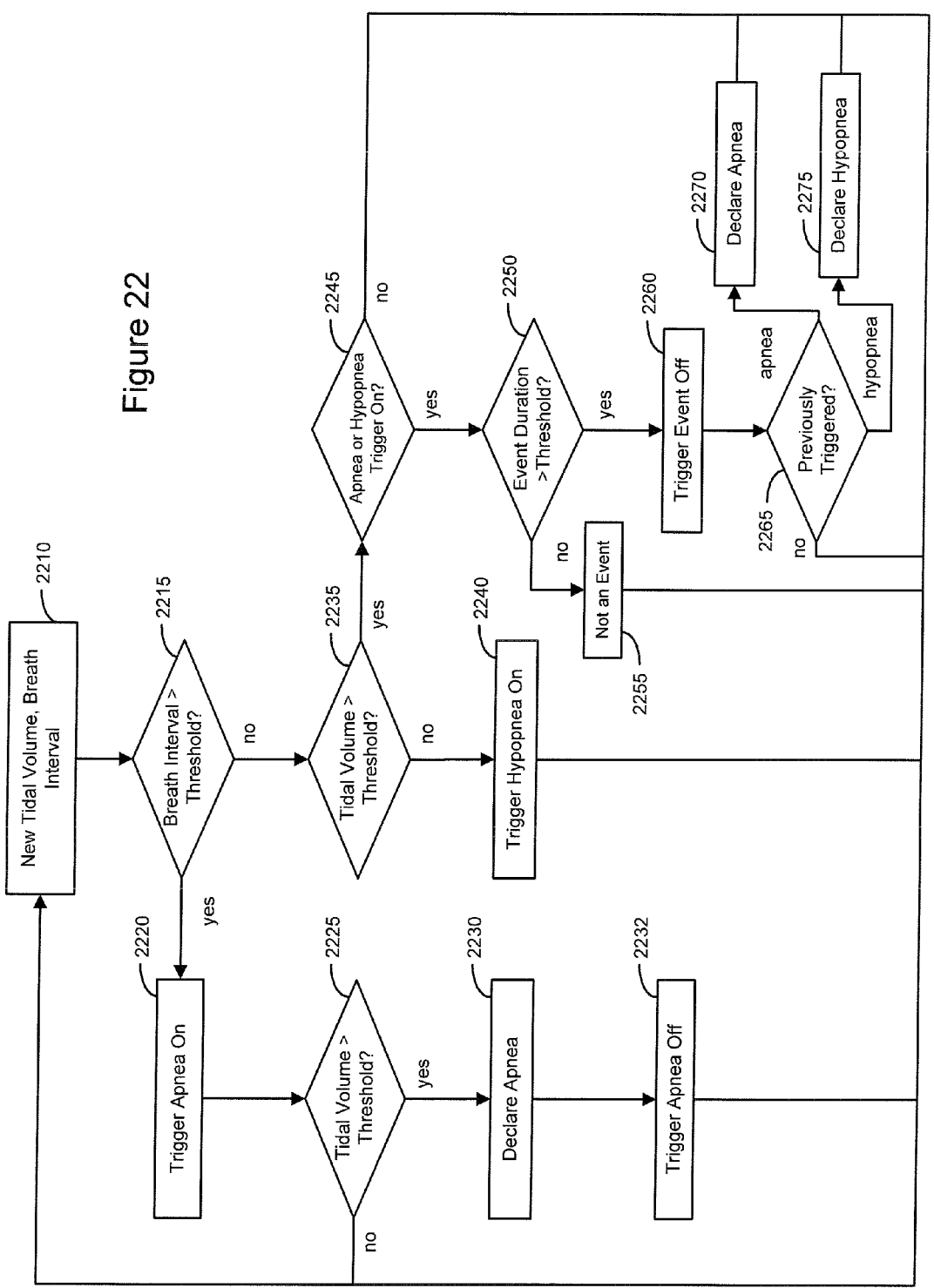
FIG. 22 is a flowchart of a method for detecting disordered breathing in accordance with embodiments of the invention.

FIG. 22 is a flowchart of a method for detecting disordered breathing in accordance with embodiments of the invention. The method illustrated in FIG. 22 operates by classifying breathing patterns using breath intervals in conjunction with tidal volume and duration thresholds as previously described above. In this example, a duration threshold and a tidal volume threshold are established for determining both apnea and hypopnea breath intervals. An apnea episode is detected if the breath interval exceeds the duration threshold. A hypopnea episode is detected if the tidal volume of successive breaths remains less than the tidal volume threshold for a period in excess of the duration threshold. Mixed apnea/hypopnea episodes may also occur. In these cases, the period of disordered breathing is characterized by shallow breaths or non-breathing intervals. During the mixed apnea/hypopnea episodes, the tidal volume of each breath remains less than the tidal volume threshold for a period exceeding the duration threshold.

Transthoracic impedance is sensed and used to determine the patient's respiration cycles. Each breath 2210 may be characterized by a breath interval, the interval of time between two impedance signal maxima, and a tidal volume (TV).

If a breath interval exceeds 2215 the duration threshold, then the respiration pattern is consistent with an apnea event, and an apnea event trigger is turned on 2220. If the tidal volume of the breath interval exceeds 2225 the tidal volume threshold, then the breathing pattern is characterized by two respiration cycles of normal volume separated by a non-breathing interval. This pattern represents a purely apneic disordered breathing event, and apnea is detected 2230. Because the final breath of the breath interval was normal, the apnea event trigger is turned off 2232, signaling the end of the disordered breathing episode. However, if the tidal volume of the breath interval does not exceed 2225 the tidal volume threshold, the disordered breathing period is continuing and the next breath is checked 2210.

If the breath interval does not exceed 2215 the duration threshold, then the tidal volume of the breath is checked 2235. If the tidal volume does not exceed 2235 the tidal volume threshold, the breathing pattern is consistent with a hypopnea cycle and a hypopnea event trigger is set on 2240. If the tidal volume exceeds the tidal volume threshold, then the breath is normal.

If a period of disordered breathing is in progress, detection of a normal breath signals the end of the disordered breathing. If disordered breathing was previously detected 2245, and if the disordered breathing event duration has not exceeded 2250 the duration threshold, and the current breath is normal, then no disordered breathing event is detected 2255. If disordered breathing was previously detected 2245, and if the disordered breathing event duration has extended for a period of time exceeding 2250 the duration threshold, and the current breath is normal, then the disordered breathing trigger is turned off 2260. In this situation, the duration of the disordered breathing episode was of sufficient duration to be classified as a disordered breathing episode. If an apnea event was previously triggered 2265, then an apnea event is declared 2270. If a hypopnea was previously triggered 2265, then a hypopnea event is declared 2275.

As previously discussed in connection with the flowcharts of FIG. 1B above, the sleep disordered breathing therapy may be modified based on information developed using one or more monitored patient conditions. The information may indicate that coordinated sleep disordered breathing therapy should be initiated, terminated or modified. The information may be developed based on the severity of the sleep disordered breathing, interactions between the sleep disordered breathing therapy and other therapies delivered to the patient, the effectiveness of the sleep disordered breathing therapy, the impact of the sleep disordered breathing therapy on the patient, and/or other parameters of the breathing therapy. Once initiated, the system may continue to monitor patient conditions to develop feedback information, and the coordinated breathing therapy may be modified based on periodically updated assessments of sleep disordered breathing severity, therapy efficacy, patient comfort during therapy, sleep quality during therapy, interactions between therapies, or other factors, for example.

A subset of patient conditions, for example, one or more of the representative conditions listed in Table 1, may be used in connection with detecting sleep disordered breathing. Another subset of patient conditions, which may overlap the conditions used sleep disordered breathing assessment, may be used in connection with the determining a severity of disordered breathing. Another subset of patient conditions may be used to determine coordinated therapy efficacy. In some scenarios, the severity of disordered breathing may be inversely related to coordinated therapy efficacy. Thus it may be possible to use a common subset of patient conditions to assess severity of disordered breathing and coordinated therapy efficacy. Other subsets may be used to assess impact to the patient and/or therapy interactions, for example.

Acute responses to disordered breathing may be used to detect disordered breathing and both acute and chronic responses may be used to assess the severity of the disordered breathing, the efficacy of the therapy and/or impact of coordinated disordered breathing therapy, for example. Conditions used to assess therapy effectiveness may be different from, or the same as, conditions used to assess an impact of the therapy on the patient. Table 4 provides a representative set of conditions that may be used for therapy assessment with respect to therapy efficacy/disordered breathing severity and therapy impact.

TABLE 4

| Condition | Therapy Impact | Therapy Efficacy/Severity |
|---|---|---|
| Arousal-Based Sleep Fragmentation Measures | May be used to assess therapy impact during sleep. | |
| Restful sleep (Patient reported) | May be used to assess therapy impact during sleep. | |
| Discomfort (Patient reported) | May be used to assess therapy impact. | |
| Pacing algorithm interaction | May be used to assess therapy impact. | |
| Heart Failure (HF)Severity | May be used to assess therapy impact. | May be used to analyze the efficacy of therapy to improve heart pumping function. HF severity may be indicated by the apnea hypopnea index. Improving apnea via therapy may improve HF condition. |
| Remaining useful life of therapy device | May be used to assess therapy impact. | |
| Disturbed Breathing-Based Measures | | May be used to analyze/assess efficacy of therapy to mitigate disordered breathing episodes. |
| Respiration quality (Patient reported) | | May be used to analyze/assess efficacy of therapy to mitigate disordered breathing episodes. |
| Heart rate variability (HRV) | | Disordered breathing causes heart rate variability to decrease. Therapy may be modified based on changes in HRV |
| Blood pressure | | Disordered breathing causes blood pressure increase |
| Sympathetic nerve activity (SNA) | | Changes in sympathetic nerve activity are caused by disordered breathing. Therapy may be adjusted based on the level of SNA |
| Blood chemistry | | A number of disordered breathing related changes may occur in a patient's blood chemistry, including, e.g., higher norepinephrine levels, and lower $PaCO_2$ |

It is understood that the patient conditions that may be used in connection the medical systems described herein are not limited to the representative sets listed in Tables 1-4 or those described herein. Further, although illustrative sensing methods for detecting the patient conditions listed above are provided, it is understood that the patient conditions may be detected using a wide variety of technologies. The embodiments and features described in herein are not limited to the particular patient conditions or the particular sensing technologies provided.

In accordance with various embodiments of the invention, conditions related to sleep quality, e.g., sleep fragmentation and/or other arousal-based measures, patient-reported restful sleep, and patient-reported discomfort during therapy, may be used to assess the impact of the therapy on the patient. For example, if a patient is receiving effective coordinated disordered breathing therapy and has low sleep fragmentation, reports restful sleep, and reports no discomfort, the adverse effects of the therapy on the patient may be relatively low. If sleep fragmentation is relatively high, or if the patient reports discomfort or feeling tired after sleeping, these conditions may indicate that coordinated therapy is causing sleep disturbances and/or other undesirable effects.

It is undesirable to provide coordinated therapy that eliminates the disordered breathing but increases sleep fragmentation. In such a situation, the disordered breathing therapy may exacerbate the adverse effects produced by the respiratory disturbances. Thus, it may be preferable to assess the impact of the therapy on the patient and adjust the therapy to improve sleep quality.

Sleep fragmentation and sleep disruptions may also occur if coordinated disordered breathing therapy is ineffective and disordered breathing occurs during sleep. Therefore, a therapy impact assessment based on detected sleep quality and/or patient-reported restful sleep may preferably take into account an assessment of therapy effectiveness.

Evaluation of the impact of coordinated disordered breathing therapy on the patient preferably takes into consideration the impact of disordered breathing therapy on the overall therapeutic goals for the patient, including goals associated with other therapies delivered to the patient as well as coordinated sleep disordered breathing therapy goals. The coordinated disordered breathing therapy may involve a variety of therapy regimens implemented to achieve predetermined therapeutic goals. In some embodiments, the effectiveness of the therapy, or the degree to which the therapy meets one or more therapeutic goals, may be assessed by detecting and analyzing episodes of disordered breathing that occur during therapy delivery.

For example, a therapeutic goal may involve terminating a disordered breathing episode and the coordinated disordered breathing therapy may be adapted to achieve this goal. Additionally, or alternatively, a therapeutic goal may involve terminating a disordered breathing episode and preventing further disordered breathing. In this example situation, the therapy a coordinated therapy regimen may be adapted to provide a first therapy to terminate the disordered breathing episode using a first therapy device and provide a second preventative therapy to reduce or eliminate further disordered breathing episodes using a second therapy device. The second preventative therapy may be adapted to reduce episodes of disordered breathing below a predetermined disordered breathing episode threshold. A disordered breathing episode threshold may be expressed, for example, in terms of an apnea/hypopnea index (AHI) or percent time in periodic breathing (% PB).

Figure 23:
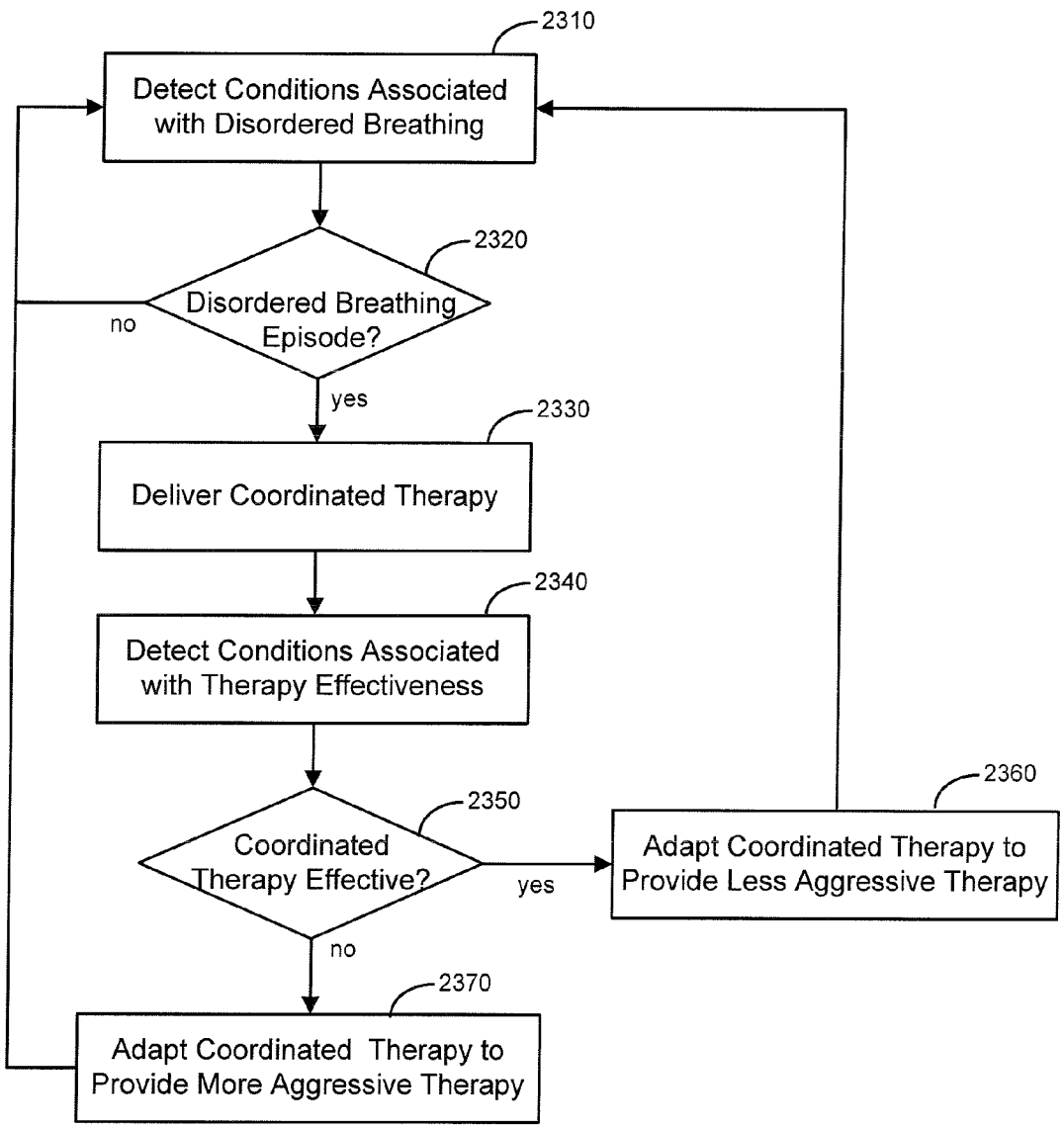
FIGS. 23 and 24 are flowcharts illustrating methods of adjusting coordinated sleep disordered breathing therapy according to embodiments of the invention.
Figure 24:
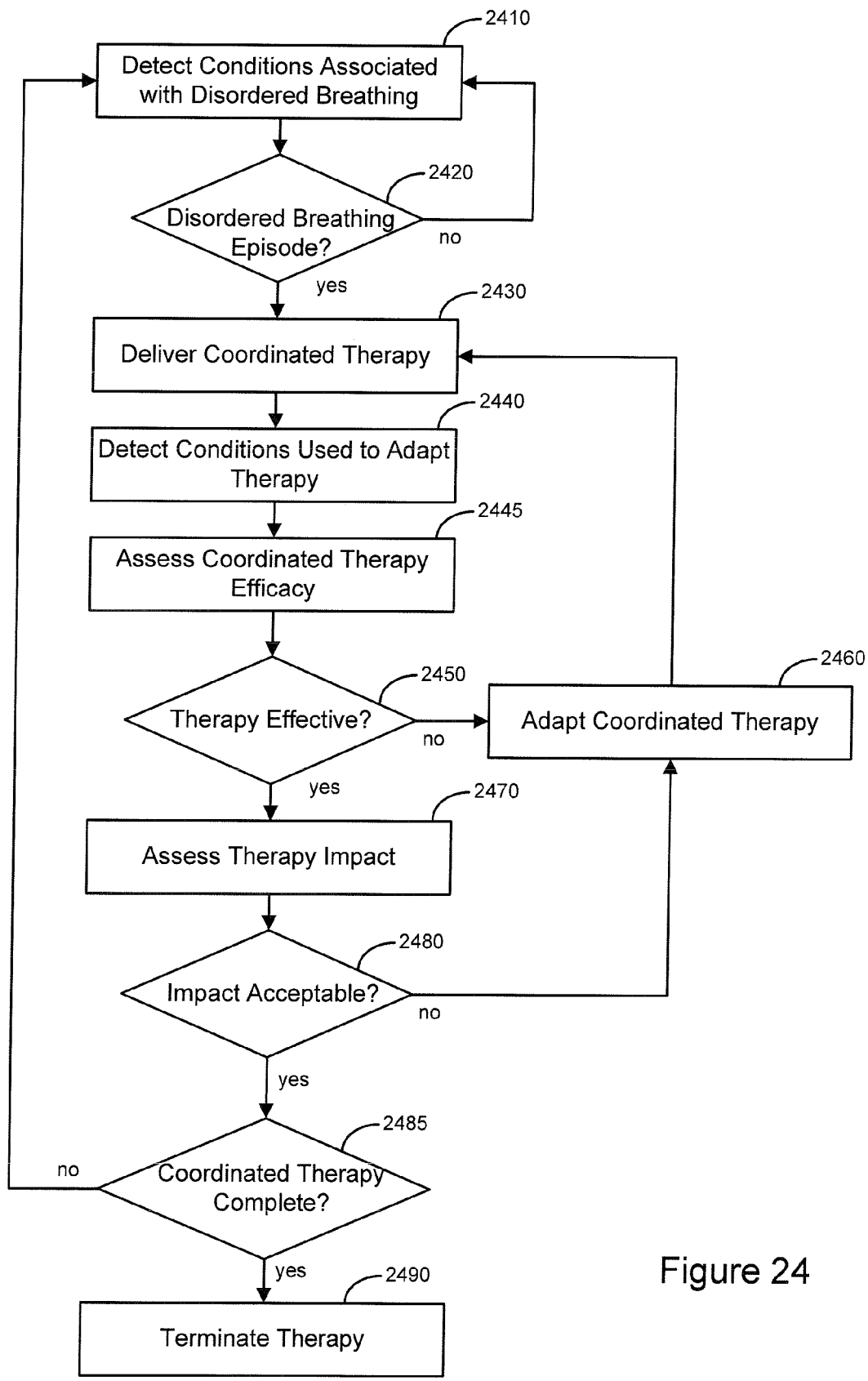

FIGS. 23 and 24 are flowcharts illustrating methods of adapting a coordinated sleep disordered breathing therapy according to embodiments of the invention. As previously discussed, the coordinated sleep disordered breathing therapy may involve one or more of a number of therapy types. The coordinated sleep disordered breathing therapy may involve, for example, one or more of cardiac pacing therapy, patient-external breathing therapy, nerve stimulation therapy, muscle stimulation therapy, and/or drug therapy. Processes for adapting a cardiac therapy based on feedback information, are described in commonly owned U.S. Pat. No. 7,720,541, which is incorporated herein by reference. Similar techniques may be applied to adjust therapy of different types.

The flowchart of FIG. 23 illustrates a method of providing coordinated disordered breathing therapy to achieve a desired level of therapy efficacy. In this embodiment, a first set of conditions associated with disordered breathing is detected 2310 and used to determine if a disordered breathing episode is occurring. If disordered breathing is detected 2320, coordinated disordered breathing therapy is delivered 2330 to the patient to mitigate the disordered breathing. In one embodiment, the therapy delivered to the patient may involve external respiratory therapy. The therapy may initially involve air delivered at a first predetermined pressure.

A second set of conditions associated with therapy effectiveness is sensed 2340 and used to assess the effectiveness of the therapy. The detected conditions used to assess the efficacy of the therapy and adapt the therapy to mitigate disordered breathing may represent one or more of the acute conditions associated with disordered breathing, e.g., detected episodes of interrupted breathing, hypoxia, arousals, negative intrathoracic pressure, blood pressure, and heart rate or blood pressure surges.

Additionally, or alternatively, the conditions used to assess therapy efficacy and adapt the coordinated sleep disordered breathing therapy may include one or more chronic conditions associated with disordered breathing, including, for example, decreased heart rate variability, increased blood pressure, chronic changes in sympathetic nerve activity, and changes in blood chemistry, such as increased levels of $PaCO_2$ and norepinephrine levels, among others.

In general, a therapeutic goal in the treatment of disordered breathing is to provide the least aggressive therapy that effectively mitigates, terminates or prevents the patient's disordered breathing or achieves a particular therapeutic goal associated with coordinated disordered breathing therapy. In order to achieve the least aggressive therapy an assessment of the efficacy of therapy or assessment of the impact of the therapy on the patient is performed. According to various embodiments, therapy efficacy may be determined by evaluating one or more patient conditions sensed or acquired using sensors positioned on internal or external medical devices and/or remote devices. The therapy regimen may be adapted based on the determined therapy efficacy to provide the least aggressive therapy.

For example, in adapting a therapy regimen the system may take into account various conditions for evaluating the impact of the therapy on the patient such as patient comfort, as indicated by patient feedback, stress on physiological systems involved in the disordered breathing therapy, interaction with cardiac pacing algorithms, e.g., bradycardia pacing, cardiac resynchronization pacing an/or anti-tachycardia pacing, as determined by interactive effects of the disordered breathing therapy with cardiac pacing, and/or sleep quality, as measured by one or more sleep quality indices, to devise a coordinated disordered breathing therapy regimen that reduces an impact of the therapy on the patient.

In addition, impact to the patient may involve reduction of the useful service life of an implantable therapeutic device used to deliver disordered breathing therapy and/or pacing therapy for cardiac dysfunction. For example, a level of disordered breathing therapy may be unacceptably high if the energy requirements of the therapy result in an excessively reduced device service life. In this situation, early device removal and replacement produces a negative impact to the patient. Therefore, therapy to mitigate disordered breathing may be adapted based on a projected reduction in device useful service life.

In one example, the therapy delivered to mitigate disordered breathing may be adapted to reduce or adjust interactions between the disordered breathing therapy and other therapies delivered to the patient. For example, some patients may receive neural stimulation therapy to treat disordered breathing and cardiac stimulation therapy to treat cardiac disorders such as bradycardia or congestive heart failure. Interactions may occur between the neural stimulation therapy and the patient's cardiac pacing regimen, e.g., pacing for bradycardia or cardiac resynchronization. Such interactions may be factored into the assessment of the impact disordered breathing therapy on the overall therapy delivered to the patient.

In another example, if the severity of the disordered breathing is determined to be severe, and therapy efficacy is lacking, then a more intense level of coordinated therapy may be initially delivered to the patient. The coordinated disordered breathing therapy regimen may be enhanced by increasing the intensity or level of one type of therapy while decreasing the intensity of another type of therapy to more effectively mitigate the disordered breathing. Alternatively, where two therapy types are delivered to the patient, the coordinated disordered breathing therapy regimen may be enhanced by increasing or decreasing the overall intensity or level of therapy in order to decrease the severity or frequency of disordered breathing episodes, thus reducing undesirable side effects from the therapy and extending the device lifetime.

If the coordinated therapy effectiveness is acceptable 2350, e.g., terminates or reduces the patient's disordered breathing or meets some other desired goal, then the coordinated therapy may be adapted 2360 to provide a less aggressive therapy, e.g., air delivered at a decreased pressure, cardiac pacing delivered at a higher rate, nerve stimulation delivered at a lower amplitude. If the coordinated therapy is not effective 2350, then the coordinated therapy may be adapted 2370 to enhance therapy efficacy by providing a more aggressive therapy regimen, e.g., delivering air at an increased pressure, cardiac pacing delivered at a lower rate, nerve stimulation delivered at a lower amplitude.

In one embodiment, coordinated therapy may be determined to be ineffective if disordered breathing continues unmitigated following therapy delivery. In this situation, the therapy may be adapted to provide a more aggressive therapy. In another embodiment, if the disordered breathing decreases sufficiently in severity, or is otherwise sufficiently mitigated, the therapy may be enhanced by adapting the therapy to provide a less aggressive therapy, e.g., decreased air pressure. As previously discussed, a less aggressive therapy is preferable to reduce the risk of arousal and to provide a more comfortable therapy to the patient, for example.

The flowchart of FIG. 24 illustrates a method of providing a coordinated disordered breathing therapy in accordance with embodiments of the invention. In this example, a first set of conditions associated with disordered breathing is detected 2410 and used to determine if a disordered breathing episode is occurring. If disordered breathing is detected 2420, coordinated therapy is delivered 2430 to the patient to mitigate the disordered breathing. The level of therapy initially delivered to the patient may be based on a severity of the disordered breathing.

A second set of conditions is detected 2440 and used to adapt the therapy. Based on the second set of sensed conditions, the therapy efficacy is assessed 2445. If the therapy efficacy is not acceptable 2450, then the coordinated therapy may be adapted 2460 to enhance therapy efficacy. If the therapy efficacy is acceptable 2450, then the impact of the therapy on the patient may be assessed 2470.

If the therapy impact on the patient is acceptable 2480, the system continues to deliver the therapy. When the coordinated therapy regimen is complete 2485, then therapy is terminated 2490. If the therapy impact on the patient exceeds acceptable limits, the therapy impact is not acceptable 2480, and the coordinated therapy may be adapted 2460 to reduce the therapy impact.

The methods illustrated in the flowcharts of FIGS. 23 and 24 contemplate real-time monitoring of patient conditions allowing the coordinated therapy system to coordinate a therapy regimen to accommodate the changing needs of the patient. In one configuration, the coordinated therapy may be adjusted during the period that therapy is delivered to the patient. In another configuration, the therapy may be adapted between sleep disordered breathing episodes or from night-to-night based on assessment of therapy delivered in connection with one or more previously detected disordered breathing episodes.

Methods, devices, and systems implementing a coordinated approach to disordered breathing treatment and/or monitoring disordered breathing may incorporate one or more of the features, structures, methods, or combinations thereof described herein. For example, a medical system may be implemented to include one or more of the features and/or processes described below. It is intended that such a method, device, or system need not include all of the features and functions described herein, but may be implemented to include one or more selected features and functions that provide unique structures and/or functionality.

A number of the examples presented herein involve block diagrams illustrating functional blocks used for coordinated monitoring, diagnosis and/or therapy functions in accordance with embodiments of the present invention. It will be understood by those skilled in the art that there exist many possible configurations in which these functional blocks can be arranged and implemented. The examples depicted herein provide examples of possible functional arrangements used to implement the approaches of the invention.

It is understood that the components and functionality depicted in the figures and described herein can be implemented in hardware, software, or a combination of hardware and software. It is further understood that the components and functionality depicted as separate or discrete blocks/elements in the figures in general can be implemented in combination with other components and functionality, and that the depiction of such components and functionality in individual or integral form is for purposes of clarity of explanation, and not of limitation.

What is claimed is:

1. An automated method for treating disordered breathing, comprising:
    delivering an external therapy to a patient to treat a respiratory condition;
    delivering an internal therapy to the patient using an implantable device to treat the respiratory condition;
    sensing one or more parameters; and
    coordinating delivery of the external therapy and the internal therapy by shifting therapy burden from the external therapy or the internal therapy to the other of the external therapy or the internal therapy based on the one or more sensed parameters.

2. The method of claim 1, wherein the respiratory condition comprises sleep disordered breathing.

3. The method of claim 1, wherein the one or more parameters comprises prediction of disordered breathing.

4. The method of claim 1, wherein the one or more parameters comprises therapy interaction between the external therapy and the internal therapy.

5. The method of claim 1, wherein the one or more parameters comprises patient usage of an external therapy device that delivers the external therapy.

6. The method of claim 1, wherein the external therapy comprises a positive airway pressure therapy.

7. The method of claim 1, wherein the internal therapy comprises electrical energy delivered internally to the patient.

8. The method of claim 1, wherein:
sensing the one or more parameters comprises sensing one or more side effect conditions affecting the patient and associated with an impact of one or more of the external therapy and the internal therapy on the patient; and
coordinating delivery comprises shifting therapy burden from the external therapy or the internal therapy associated with the side effect condition to the other of the external therapy or the internal therapy.

9. The method of claim 1, wherein:
sensing the one or more parameters comprises sensing an impact of one or more of the external therapy and the internal therapy on the patient; and
coordinating delivery comprises shifting therapy burden from the external therapy or the internal therapy to the other of the external therapy or the internal therapy based on the sensed impact.

10. The method of claim 1, wherein:
sensing the one or more parameters comprises sensing excessive battery life consumption by the implantable device in delivering the internal therapy; and
coordinating delivery comprises shifting therapy burden from the internal therapy to the external therapy.

11. The method of claim 1, wherein:
sensing the one or more parameters comprises sensing an indication of patient discomfort associated with delivery of one or more of the external therapy and the internal therapy on the patient; and
coordinating delivery comprises shifting therapy burden from the external therapy or the internal therapy associated with the indication of patient discomfort to the other of the external therapy or the internal therapy.

12. A medical system for controlling therapy to treat a respiratory condition comprising:
a patient external therapy device configured to deliver an external therapy to a patient to treat a respiratory condition;
an implantable device configured to implantably deliver an internal therapy to the patient to treat the respiratory condition;
a sensor system for sensing one or more parameters; and
circuitry in communication with the external therapy device, the implantable device, and the sensor system, the circuitry configured to coordinate delivery of the external therapy and the internal therapy by shifting therapy burden from the external therapy or the internal therapy to the other of the external therapy or the internal therapy based on the one or more sensed parameters.

13. The medical system of claim 12, wherein the respiratory condition comprises sleep disordered breathing.

14. The medical system of claim 12, wherein the circuitry is further configured to predict sleep disordered breathing based on the one or more parameters and shift therapy burden from the external therapy or the internal therapy to the other of the external therapy or the internal therapy based on the sleep disordered breathing prediction.

15. The medical system of claim 12, wherein the one or more parameters comprises usage of the patient external therapy device.

16. The medical system of claim 12, wherein:
the sensor system is configured to sense at least one or more side effect conditions associated with an impact of one or both of the external therapy and the internal therapy on the patient as the one or more parameters; and
the circuitry is configured to shift therapy burden from the external therapy or the internal therapy associated with the side effect condition to the other of the external therapy or the internal therapy.

17. The medical system of claim 12, wherein:
the sensor system is configured to sense impact of one or both of the external therapy and the internal therapy on the patient as the one or more parameters; and
the circuitry is configured to shift therapy burden from the external therapy or the internal therapy to the other of the external therapy or the internal therapy based on the sensed impact.

18. The medical system of claim 12, wherein:
the sensor system is configured to sense excessive battery life consumption by the implantable device in delivery of the internal therapy as the one or more parameters; and
the circuitry is configured to shift therapy burden from the internal therapy to the external therapy based on the sensed excessive battery life consumption.

19. The medical system of claim 12, wherein:
the sensor system is configured to sense patient discomfort associated with one of the external therapy and the internal therapy on the patient as the one or more parameters; and
the circuitry is configured to shift therapy burden from the external therapy or the internal therapy associated with the patient discomfort to the other of the external therapy or the internal therapy.

20. A medical system for treating a respiratory condition, comprising:
means for delivering an external therapy to a patient to treat a respiratory condition;
means for delivering an internal therapy to the patient to treat the respiratory condition;
means for sensing one or more parameters; and
means for coordinating delivery of the external therapy and the internal therapy to address the respiratory condition by shifting therapy burden from the external therapy or the internal therapy to the other of the external therapy or the internal therapy based on the one or more sensed parameters.

* * * * *